(12) United States Patent
Mirkin et al.

(10) Patent No.: US 11,364,304 B2
(45) Date of Patent: Jun. 21, 2022

(54) CROSSLINKED MICELLAR SPHERICAL NUCLEIC ACIDS

(71) Applicant: NORTHWESTERN UNIVERSITY, Evanston, IL (US)

(72) Inventors: Chad A. Mirkin, Wilmette, IL (US); SonBinh T. Nguyen, Evanston, IL (US); Resham J. Banga, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/328,025

(22) PCT Filed: Aug. 25, 2017

(86) PCT No.: PCT/US2017/048726
§ 371 (c)(1),
(2) Date: Feb. 25, 2019

(87) PCT Pub. No.: WO2018/039629
PCT Pub. Date: Mar. 1, 2018

(65) Prior Publication Data
US 2019/0275166 A1  Sep. 12, 2019

Related U.S. Application Data

(60) Provisional application No. 62/379,352, filed on Aug. 25, 2016.

(51) Int. Cl.
| | | |
|---|---|---|
| *C12N 15/11* | (2006.01) | |
| *A61K 47/69* | (2017.01) | |
| *A61K 31/7105* | (2006.01) | |
| *A61K 31/711* | (2006.01) | |
| *C12N 15/113* | (2010.01) | |
| *C12N 15/88* | (2006.01) | |
| *C07H 21/02* | (2006.01) | |
| *C07H 21/04* | (2006.01) | |

(52) U.S. Cl.
CPC ........ *A61K 47/6917* (2017.08); *A61K 31/711* (2013.01); *A61K 31/7105* (2013.01); *C07H 21/02* (2013.01); *C07H 21/04* (2013.01); *C12N 15/113* (2013.01); *C12N 15/88* (2013.01); *C12N 2310/11* (2013.01); *C12N 2310/141* (2013.01)

(58) Field of Classification Search
CPC ............... A61K 49/0093; A61K 9/127; A61K 31/7105; A61K 47/6911; A61K 47/6931; A61K 31/655; A61K 31/711; A61K 47/60
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,489,055 A | 12/1984 | Couvreur et al. |
| 4,845,205 A | 7/1989 | Huynh Dinh et al. |
| 4,904,582 A | 2/1990 | Tullis |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |

(Continued)

FOREIGN PATENT DOCUMENTS

| | | |
|---|---|---|
| AR | 070368 A2 | 3/2010 |
| AU | 2004218696 A1 | 11/2004 |

(Continued)

OTHER PUBLICATIONS

Jain et al., Synthesis of protein-loaded hydrogel particles in an aqueous two-phase system for coincident antigen and CpG oligonucleotide dllivery to antigen-presenting cells, Biomacromolecules, vol. 6, pp. 2590-2600. (Year: 2005).*

Chandaroy et al., Temperature-controlled content release from liposomes encapsulating Pluronic F127, Journal of Controlled Release, vol. 76, pp. 27-37. (Year: 2001).*

Kaczmarek et al., 2'-linking of lipids and other functions to uridine through 1,2,3-triazoles and membrane anchoring of the amphiphilic products, European Journal of Organic Chemistry, vol. 2010, pp. 1579-1586. (Year: 2010).*

(Continued)

*Primary Examiner* — Dana H Shin

(74) *Attorney, Agent, or Firm* — Wolf, Greenfield & Sacks, P.C.

(57) ABSTRACT

Methods of preparing crosslinked spherical nucleic acids (SNAs) using thermoresponsive traceless templates, such as PEO-PPO-PEO block copolymers. The crosslinks can be added between oligonucleotides within the same SNA or oligonucleotides between multiple different SNAs.

14 Claims, 4 Drawing Sheets

Specification includes a Sequence Listing.

(56) References Cited

U.S. PATENT DOCUMENTS

| | | |
|---|---|---|
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,512,439 A | 4/1996 | Hornes et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,780,448 A | 7/1998 | Davis |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,051,698 A | 4/2000 | Janjic et al. |
| 6,194,388 B1 | 2/2001 | Krieg et al. |
| 6,207,646 B1 | 3/2001 | Krieg et al. |
| 6,239,116 B1 | 5/2001 | Krieg et al. |
| 6,271,209 B1 | 8/2001 | Smith et al. |
| 6,361,944 B1 | 3/2002 | Mirkin et al. |
| 6,406,705 B1 | 6/2002 | Davis et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,534,062 B2 | 3/2003 | Raz et al. |
| 6,582,921 B2 | 6/2003 | Mirkin et al. |
| 6,602,669 B2 | 8/2003 | Letsinger et al. |
| 6,610,308 B1 | 8/2003 | Haensler |
| 6,610,491 B2 | 8/2003 | Mirkin et al. |
| 6,677,122 B2 | 1/2004 | Mirkin et al. |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,812,334 B1 | 11/2004 | Mirkin et al. |
| 6,818,753 B2 | 11/2004 | Mirkin et al. |
| 6,828,432 B2 | 12/2004 | Mirkin et al. |
| 6,849,725 B2 | 2/2005 | Junghans et al. |
| 6,861,221 B2 | 3/2005 | Mirkin et al. |
| 6,878,814 B2 | 4/2005 | Mirkin et al. |
| 7,038,029 B2 | 5/2006 | Lopez |
| 7,098,320 B1 | 8/2006 | Mirkin et al. |
| 7,129,222 B2 | 10/2006 | Van Nest et al. |
| 7,176,296 B2 | 2/2007 | Agrawal et al. |
| 7,208,587 B2 | 4/2007 | Mirkin et al. |
| 7,223,741 B2 | 5/2007 | Krieg |
| 7,238,472 B2 | 7/2007 | Mirkin et al. |
| 7,250,403 B2 | 7/2007 | Van Nest et al. |
| 7,255,868 B2 | 8/2007 | Fearon et al. |
| 7,262,286 B2 | 8/2007 | Kandimalla et al. |
| 7,276,489 B2 | 10/2007 | Agrawal et al. |
| 7,291,284 B2 | 11/2007 | Mirkin et al. |
| 7,332,586 B2 | 2/2008 | Franzen et al. |
| 7,354,907 B2 | 4/2008 | Agrawal et al. |
| 7,387,271 B2 | 6/2008 | Noelle et al. |
| 7,404,969 B2 | 7/2008 | Chen et al. |
| 7,427,405 B2 | 9/2008 | Agrawal et al. |
| 7,470,674 B2 | 12/2008 | Agrawal et al. |
| 7,514,099 B2 | 4/2009 | Chen et al. |
| 7,563,618 B2 | 7/2009 | Gryaznov et al. |
| 7,569,553 B2 | 8/2009 | Krieg |
| 7,569,554 B2 | 8/2009 | Kandimalla et al. |
| 7,615,539 B2 | 11/2009 | Uhlmann et al. |
| 7,628,990 B2 | 12/2009 | Tuck et al. |
| 7,666,674 B2 | 2/2010 | Klinman et al. |
| 7,709,617 B2 | 5/2010 | Kandimalla et al. |
| 7,713,535 B2 | 5/2010 | Agrawal et al. |
| 7,718,622 B2 | 5/2010 | Tuck et al. |
| 7,727,969 B2 | 6/2010 | Farokhzad et al. |
| 7,745,606 B2 | 6/2010 | Dina et al. |
| 7,776,834 B2 | 8/2010 | Agrawal et al. |
| 7,786,089 B2 | 8/2010 | Kandimalla et al. |
| 7,833,992 B2 | 11/2010 | Vargeese et al. |
| 7,850,990 B2 | 12/2010 | Tardi et al. |
| 7,851,453 B2 | 12/2010 | Agrawal et al. |
| 7,875,594 B2 | 1/2011 | Kandimalla et al. |
| 7,884,083 B2 | 2/2011 | Van Nest et al. |
| 7,884,197 B2 | 2/2011 | Kandimalla et al. |
| 7,956,176 B2 | 6/2011 | McSwiggen et al. |
| 7,960,362 B2 | 6/2011 | Kandimalla et al. |
| 7,964,578 B2 | 6/2011 | Vargeese et al. |
| 7,993,659 B2 | 8/2011 | Noelle et al. |
| 8,008,266 B2 | 8/2011 | Krieg et al. |
| 8,008,267 B2 | 8/2011 | Kandimalla et al. |
| 8,017,591 B2 | 9/2011 | Brzezicha et al. |
| 8,058,249 B2 | 11/2011 | Krieg et al. |
| 8,088,388 B2 | 1/2012 | Sokoll |

(56) References Cited

U.S. PATENT DOCUMENTS

| | | |
|---|---|---|
| 8,124,590 B2 | 2/2012 | Van Nest et al. |
| 8,128,944 B2 | 3/2012 | Jurk et al. |
| 8,158,768 B2 | 4/2012 | Dina et al. |
| 8,188,261 B2 | 5/2012 | Kandimalla et al. |
| 8,202,979 B2 | 6/2012 | McSwiggen et al. |
| 8,273,866 B2 | 9/2012 | McSwiggen et al. |
| 8,283,328 B2 | 10/2012 | Krieg et al. |
| 8,304,396 B2 | 11/2012 | Krieg et al. |
| 8,309,527 B2 | 11/2012 | Krieg et al. |
| 8,323,686 B2 | 12/2012 | Mirkin et al. |
| 8,333,980 B2 | 12/2012 | Van Nest et al. |
| 8,431,544 B1 | 4/2013 | Agrawal et al. |
| 8,507,200 B2 | 8/2013 | Mirkin et al. |
| 8,846,080 B2 | 9/2014 | Biemans et al. |
| 8,853,375 B2 | 10/2014 | Kandimalla et al. |
| 8,871,732 B2 | 10/2014 | Dina et al. |
| 8,889,181 B2 | 11/2014 | Kwon |
| 8,940,310 B2 | 1/2015 | Barrat et al. |
| 8,945,590 B2 | 2/2015 | Fairman et al. |
| 8,968,746 B2 | 3/2015 | Baumhof et al. |
| 8,987,221 B2 | 3/2015 | Zhu et al. |
| 9,061,001 B2 | 6/2015 | van Drunen Littel-van den Hurk et al. |
| 9,066,978 B2 | 6/2015 | Ilyinskii et al. |
| 9,139,827 B2 | 9/2015 | Mirkin et al. |
| 9,192,667 B2 | 11/2015 | Hoves et al. |
| 9,200,287 B2 | 12/2015 | Uhlmann et al. |
| 9,212,366 B2 | 12/2015 | Wittig et al. |
| 9,265,729 B2 | 2/2016 | Nakamura |
| 9,308,253 B2 | 4/2016 | Kim et al. |
| 9,364,443 B2 | 6/2016 | Beduneau et al. |
| 9,421,254 B2 | 8/2016 | Berzofsky et al. |
| 9,499,815 B1 | 11/2016 | Schroff et al. |
| 9,506,056 B2 | 11/2016 | Mirkin et al. |
| 9,522,958 B2 | 12/2016 | Epstein et al. |
| 9,532,948 B2 | 1/2017 | Mirkin et al. |
| 9,549,901 B2 | 1/2017 | Shi et al. |
| 9,617,541 B2 | 4/2017 | Mirkin et al. |
| 9,617,547 B2 | 4/2017 | Gemba |
| 9,764,031 B2 | 9/2017 | Ilyinskii et al. |
| 9,844,562 B2 | 12/2017 | Mirkin et al. |
| 9,868,955 B2 | 1/2018 | Guiducci et al. |
| 9,889,209 B2 | 2/2018 | Mirkin et al. |
| 9,901,616 B2 | 2/2018 | Dhar et al. |
| 9,907,845 B2 | 3/2018 | Reed et al. |
| 9,907,862 B2 | 3/2018 | Baumhof et al. |
| 9,919,058 B2 | 3/2018 | Klinman et al. |
| 9,950,063 B2 | 4/2018 | Reed et al. |
| 9,950,064 B2 | 4/2018 | Ott et al. |
| 9,968,673 B2 | 5/2018 | Navarro y Garcia et al. |
| 9,976,147 B2 | 5/2018 | Kortylewski et al. |
| 9,987,355 B2 | 6/2018 | Reed et al. |
| 9,993,495 B2 | 6/2018 | Guiducci et al. |
| 9,999,673 B2 | 6/2018 | Rajeev et al. |
| 10,006,032 B2 | 6/2018 | Schroff et al. |
| 10,029,016 B2 | 7/2018 | Irvine et al. |
| 10,098,958 B2 | 10/2018 | Mirkin et al. |
| 10,111,899 B2 | 10/2018 | Guiducci et al. |
| 10,144,933 B2 | 12/2018 | Gemba et al. |
| 10,149,905 B2 | 12/2018 | Gemba et al. |
| 10,155,950 B2 | 12/2018 | Munnes et al. |
| 10,182,988 B2 | 1/2019 | Mirkin et al. |
| 10,196,643 B2 | 2/2019 | Dina et al. |
| 10,208,310 B2 | 2/2019 | Mader et al. |
| 10,280,424 B2 | 5/2019 | Kleuss et al. |
| 10,314,854 B2 | 6/2019 | Salem et al. |
| 10,322,173 B2 | 6/2019 | Gemba et al. |
| 10,369,220 B2 | 8/2019 | Kaplan |
| 10,370,656 B2 | 8/2019 | Mirkin et al. |
| 10,391,116 B2 | 8/2019 | Mirkin et al. |
| 10,398,784 B2 | 9/2019 | Mirkin et al. |
| 10,435,469 B2 | 10/2019 | Goldberg et al. |
| 10,449,212 B2 | 10/2019 | Hanagata et al. |
| 10,456,463 B2 | 10/2019 | Davis et al. |
| 10,463,686 B2 | 11/2019 | Agrawal et al. |
| 10,487,333 B2 | 11/2019 | Schroff et al. |
| 10,792,251 B2 | 10/2020 | Mirkin et al. |
| 2002/0156033 A1 | 10/2002 | Bratzler et al. |
| 2002/0172953 A1 | 11/2002 | Mirkin et al. |
| 2002/0197269 A1 | 12/2002 | Lingnau et al. |
| 2003/0026782 A1 | 2/2003 | Krieg |
| 2003/0050261 A1 | 3/2003 | Krieg et al. |
| 2003/0091599 A1 | 5/2003 | Davis et al. |
| 2003/0104044 A1 | 6/2003 | Semple et al. |
| 2003/0129251 A1 | 7/2003 | Van Nest et al. |
| 2003/0133988 A1 | 7/2003 | Fearon et al. |
| 2003/0138413 A1 | 7/2003 | Vicari et al. |
| 2003/0147966 A1 | 8/2003 | Franzen et al. |
| 2003/0170162 A1 | 9/2003 | Nayfeh et al. |
| 2003/0181412 A1 | 9/2003 | Erikson |
| 2003/0212026 A1 | 11/2003 | Krieg et al. |
| 2004/0014956 A1 | 1/2004 | Woolf et al. |
| 2004/0023382 A1 | 2/2004 | Dean et al. |
| 2004/0053384 A1 | 3/2004 | Sligar et al. |
| 2004/0087534 A1 | 5/2004 | Krieg et al. |
| 2004/0092468 A1 | 5/2004 | Schwartz |
| 2004/0131628 A1 | 7/2004 | Bratzler et al. |
| 2004/0143112 A1 | 7/2004 | Krieg et al. |
| 2004/0158051 A1 | 8/2004 | Ozkan et al. |
| 2004/0219565 A1 | 11/2004 | Kauppinen et al. |
| 2004/0247680 A1 | 12/2004 | Farokhzad et al. |
| 2004/0266719 A1 | 12/2004 | McCluskie et al. |
| 2005/0009773 A1 | 1/2005 | Kandimalla et al. |
| 2005/0130911 A1 | 6/2005 | Uhlmann et al. |
| 2005/0169888 A1 | 8/2005 | Hartmann et al. |
| 2006/0003962 A1 | 1/2006 | Ahluwalia et al. |
| 2006/0014191 A1 | 1/2006 | Lao et al. |
| 2006/0014713 A1 | 1/2006 | Agrawal et al. |
| 2006/0019916 A1 | 1/2006 | Krieg et al. |
| 2006/0083781 A1 | 4/2006 | Shastri et al. |
| 2006/0147456 A1 | 7/2006 | Lebecque et al. |
| 2006/0159921 A1 | 7/2006 | Murthy et al. |
| 2006/0188560 A1 | 8/2006 | Cheresh et al. |
| 2006/0251623 A1 | 11/2006 | Bachmann et al. |
| 2006/0292174 A1 | 12/2006 | de los Rios et al. |
| 2007/0066554 A1 | 3/2007 | Krieg et al. |
| 2007/0093439 A1 | 4/2007 | Agrawal et al. |
| 2007/0148251 A1 | 6/2007 | Hossainy et al. |
| 2007/0184068 A1 | 8/2007 | Renner et al. |
| 2007/0243196 A1 | 10/2007 | Bruck et al. |
| 2007/0298257 A1 | 12/2007 | Ludwig et al. |
| 2008/0003232 A1 | 1/2008 | Wang et al. |
| 2008/0097092 A1 | 4/2008 | Khvorova et al. |
| 2008/0124366 A1 | 5/2008 | Ohlfest et al. |
| 2008/0181928 A1 | 7/2008 | Hakimi-Mehr et al. |
| 2008/0194463 A1 | 8/2008 | Weller et al. |
| 2008/0206265 A1 | 8/2008 | Kandimalla et al. |
| 2008/0213177 A1 | 9/2008 | Rademacher et al. |
| 2008/0220072 A1 | 9/2008 | Unger et al. |
| 2008/0274454 A1 | 11/2008 | Mirkin et al. |
| 2008/0279785 A1 | 11/2008 | Kandimalla et al. |
| 2008/0306016 A1 | 12/2008 | Mirkin et al. |
| 2008/0311182 A1 | 12/2008 | Ferrari et al. |
| 2009/0018028 A1 | 1/2009 | Lindsay et al. |
| 2009/0035576 A1 | 2/2009 | Prasad et al. |
| 2009/0081157 A1 | 3/2009 | Kornbluth et al. |
| 2009/0148384 A1 | 6/2009 | Fischer et al. |
| 2009/0155173 A1 | 6/2009 | Scherman et al. |
| 2009/0191185 A1 | 7/2009 | Selander |
| 2009/0191188 A1 | 7/2009 | Krieg et al. |
| 2009/0209629 A1 | 8/2009 | Mirkin et al. |
| 2009/0220607 A1* | 9/2009 | Kiser .................. C08G 73/08 514/1.1 |
| 2009/0299045 A1 | 12/2009 | Richards et al. |
| 2009/0317802 A1 | 12/2009 | Bhatia et al. |
| 2009/0322327 A1 | 12/2009 | Gao |
| 2009/0324706 A1 | 12/2009 | Mirkin et al. |
| 2010/0003287 A1 | 1/2010 | Mills et al. |
| 2010/0003317 A1 | 1/2010 | Akinc et al. |
| 2010/0092486 A1 | 4/2010 | Kandimalla et al. |
| 2010/0136682 A1 | 6/2010 | Mirkin et al. |
| 2010/0144848 A1 | 6/2010 | Vogel et al. |
| 2010/0166842 A1 | 7/2010 | Lu et al. |
| 2010/0167051 A1 | 7/2010 | Goia et al. |

(56) References Cited

U.S. PATENT DOCUMENTS

| | | |
|---|---|---|
| 2010/0183634 A1 | 7/2010 | Luo et al. |
| 2010/0184844 A1 | 7/2010 | Mirkin et al. |
| 2010/0203142 A1 | 8/2010 | Zhang et al. |
| 2010/0233270 A1 | 9/2010 | Mirkin et al. |
| 2010/0267814 A1 | 10/2010 | Bennett et al. |
| 2010/0303803 A1 | 12/2010 | Schroff et al. |
| 2011/0009477 A1 | 1/2011 | Yu et al. |
| 2011/0052697 A1 | 3/2011 | Farokhzad et al. |
| 2011/0111974 A1 | 5/2011 | Mirkin et al. |
| 2011/0158937 A1 | 6/2011 | Kandimalla et al. |
| 2011/0172404 A1 | 7/2011 | Luo et al. |
| 2011/0201672 A1 | 8/2011 | Krieg et al. |
| 2011/0223257 A1 | 9/2011 | Zhao et al. |
| 2011/0229529 A1 | 9/2011 | Irvine et al. |
| 2011/0237435 A1 | 9/2011 | Ryan |
| 2011/0256224 A1 | 10/2011 | Sigalov |
| 2011/0262347 A1 | 10/2011 | Ruoslahti et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2011/0305734 A1 | 12/2011 | Edelson et al. |
| 2012/0093804 A1 | 4/2012 | Schroff et al. |
| 2012/0093914 A1 | 4/2012 | Schubert |
| 2012/0107303 A1 | 5/2012 | Kandimalla et al. |
| 2012/0149843 A1 | 6/2012 | Chien et al. |
| 2012/0244230 A1 | 9/2012 | Mirkin et al. |
| 2012/0258126 A1 | 10/2012 | Scholler et al. |
| 2012/0258140 A1 | 10/2012 | Jurk et al. |
| 2012/0282186 A1 | 11/2012 | Mirkin et al. |
| 2012/0288935 A1* | 11/2012 | Mirkin .............. A61K 49/1833 435/375 |
| 2012/0301499 A1 | 11/2012 | Bachmann et al. |
| 2013/0028857 A1 | 1/2013 | Gao et al. |
| 2013/0034599 A1 | 2/2013 | Thaxton et al. |
| 2013/0071403 A1 | 3/2013 | Rolland et al. |
| 2013/0095039 A1 | 4/2013 | Lu et al. |
| 2013/0123333 A1 | 5/2013 | Mirkin et al. |
| 2013/0136714 A1 | 5/2013 | Wang et al. |
| 2013/0178610 A1 | 7/2013 | Mirkin et al. |
| 2013/0252852 A1 | 9/2013 | Pfeiffer et al. |
| 2013/0287814 A1 | 10/2013 | Schroff et al. |
| 2013/0295129 A1 | 11/2013 | Irvine et al. |
| 2013/0315831 A1 | 11/2013 | Shi et al. |
| 2014/0005258 A1 | 1/2014 | Mirkin et al. |
| 2014/0065425 A1 | 3/2014 | Bogdanov |
| 2014/0199379 A1 | 7/2014 | Tartour et al. |
| 2014/0227327 A1 | 8/2014 | Bencherif et al. |
| 2014/0294927 A1 | 10/2014 | Thaxton et al. |
| 2015/0104501 A1 | 4/2015 | Um et al. |
| 2015/0118264 A1 | 4/2015 | Baumhof et al. |
| 2016/0082103 A1 | 3/2016 | Dickey et al. |
| 2016/0101128 A1 | 4/2016 | Wang et al. |
| 2016/0108123 A1 | 4/2016 | Freeman et al. |
| 2016/0159905 A1 | 6/2016 | Abdiche et al. |
| 2016/0194642 A1 | 7/2016 | Gryaznov et al. |
| 2016/0237429 A1 | 8/2016 | Cubillos-Ruiz et al. |
| 2016/0310425 A1 | 10/2016 | Mirkin et al. |
| 2016/0339090 A1 | 11/2016 | Hacohen et al. |
| 2016/0375115 A1 | 12/2016 | Binder et al. |
| 2017/0042920 A1 | 2/2017 | Banti |
| 2017/0044544 A1 | 2/2017 | Mirkin et al. |
| 2017/0130231 A1 | 5/2017 | Chae et al. |
| 2017/0224797 A1 | 8/2017 | Popescu et al. |
| 2017/0232109 A1 | 8/2017 | Mirkin et al. |
| 2017/0239338 A1 | 8/2017 | Szalay et al. |
| 2017/0274004 A1 | 9/2017 | Wang et al. |
| 2017/0306038 A1 | 10/2017 | Brogdon et al. |
| 2017/0326232 A1 | 11/2017 | Guiducci et al. |
| 2018/0000851 A1 | 1/2018 | Krieg |
| 2018/0021253 A1 | 1/2018 | Sandeep et al. |
| 2018/0043023 A1 | 2/2018 | Ilyinskii et al. |
| 2018/0085350 A1 | 3/2018 | Avigan et al. |
| 2018/0085398 A1 | 3/2018 | Avigan et al. |
| 2018/0125877 A1 | 5/2018 | Agrawal et al. |
| 2018/0127717 A1 | 5/2018 | Decker et al. |
| 2018/0140691 A1 | 5/2018 | Takasu et al. |
| 2018/0161427 A1 | 6/2018 | Yu et al. |
| 2018/0169229 A1 | 6/2018 | Yu et al. |
| 2018/0193382 A1 | 7/2018 | Barrat |
| 2018/0200381 A1 | 7/2018 | Kannan et al. |
| 2018/0216196 A1 | 8/2018 | Kadel et al. |
| 2018/0222982 A1 | 8/2018 | Dranoff et al. |
| 2018/0251767 A1 | 9/2018 | Schroff et al. |
| 2018/0264105 A1 | 9/2018 | Kugimiya et al. |
| 2018/0311176 A1 | 11/2018 | Ozsolak et al. |
| 2018/0312536 A1 | 11/2018 | Sakamuri et al. |
| 2018/0312837 A1 | 11/2018 | Kortylewski et al. |
| 2018/0318365 A1 | 11/2018 | Yeung et al. |
| 2018/0344873 A1 | 12/2018 | Mirkin et al. |
| 2019/0030185 A1 | 1/2019 | Mirkin et al. |
| 2019/0046638 A1 | 2/2019 | Krieg |
| 2019/0048342 A1 | 2/2019 | Wang et al. |
| 2019/0077856 A1 | 3/2019 | Scheinberg et al. |
| 2019/0083626 A1 | 3/2019 | Goldberg et al. |
| 2019/0134172 A1 | 5/2019 | Gunn et al. |
| 2019/0153098 A1 | 5/2019 | Goldberg et al. |
| 2019/0201334 A1 | 7/2019 | Hakim et al. |
| 2019/0209604 A1 | 7/2019 | Zhang et al. |
| 2019/0216816 A1 | 7/2019 | Kutok |
| 2019/0233825 A1 | 8/2019 | Ilg et al. |
| 2019/0275166 A1 | 9/2019 | Mirkin et al. |
| 2019/0321613 A1 | 10/2019 | Jones et al. |
| 2019/0351053 A1 | 11/2019 | Lamprecht et al. |
| 2019/0359983 A1 | 11/2019 | O'Neill et al. |
| 2020/0031930 A1 | 1/2020 | Goldberg et al. |
| 2020/0032265 A1 | 1/2020 | Hornung et al. |
| 2020/0101156 A1 | 4/2020 | Mirkin et al. |
| 2020/0230234 A1 | 7/2020 | Schroff et al. |
| 2020/0291394 A1 | 9/2020 | Mirkin et al. |
| 2021/0052497 A1 | 2/2021 | Mirkin et al. |

FOREIGN PATENT DOCUMENTS

| | | |
|---|---|---|
| CN | 102165061 A | 8/2011 |
| CN | 103212089 A | 7/2013 |
| EP | 1 072 679 A2 | 1/2001 |
| EP | 1 221 955 B1 | 9/2005 |
| EP | 1628531 A2 | 3/2006 |
| EP | 1 700 603 A3 | 6/2007 |
| EP | 1802757 A2 | 7/2007 |
| EP | 1 889 911 A2 | 2/2008 |
| EP | 1350262 B1 | 6/2008 |
| EP | 1991678 A2 | 11/2008 |
| EP | 2162117 A2 | 3/2010 |
| EP | 1408110 B1 | 6/2011 |
| EP | 2391718 A2 | 12/2011 |
| EP | 2399608 A1 | 12/2011 |
| EP | 1807094 B1 | 1/2012 |
| EP | 2563384 A2 | 3/2013 |
| EP | 2874651 A1 | 5/2015 |
| EP | 2970369 A2 | 1/2016 |
| EP | 2759306 B1 | 4/2016 |
| EP | 2 360 252 B1 | 2/2017 |
| EP | 3204040 A1 | 8/2017 |
| EP | 3209778 B1 | 4/2019 |
| EP | 3492098 A1 | 6/2019 |
| JP | 2014-503475 A | 2/2014 |
| WO | WO 89/002439 A1 | 3/1989 |
| WO | WO 92/21330 A1 | 12/1992 |
| WO | WO 93/007883 A1 | 4/1993 |
| WO | WO 93/21528 A1 | 10/1993 |
| WO | WO 95/006731 A2 | 3/1995 |
| WO | WO 96/034876 A1 | 11/1996 |
| WO | WO-1997/12896 A1 | 4/1997 |
| WO | WO 97/48715 A1 | 12/1997 |
| WO | WO 1998/04740 A1 | 2/1998 |
| WO | WO-1998/39352 A1 | 9/1998 |
| WO | WO-1999/14226 A2 | 3/1999 |
| WO | WO 99/27086 A1 | 6/1999 |
| WO | WO 00/20645 A1 | 4/2000 |
| WO | WO 2001/000876 A1 | 1/2001 |
| WO | WO 2001/049869 A1 | 7/2001 |
| WO | WO 2002/044321 A2 | 6/2002 |
| WO | WO 2002/096262 A2 | 12/2002 |

(56) References Cited

FOREIGN PATENT DOCUMENTS

| | | |
|---|---|---|
| WO | WO 2003/008539 A2 | 1/2003 |
| WO | WO 03/030941 A1 | 4/2003 |
| WO | WO 2003/051278 A2 | 6/2003 |
| WO | WO 2003/086280 A2 | 10/2003 |
| WO | WO 2004/047870 A2 | 6/2004 |
| WO | WO 2005/063201 A2 | 7/2005 |
| WO | WO 2005/079462 A2 | 9/2005 |
| WO | WO 2005/116226 A2 | 12/2005 |
| WO | WO 2006/015560 A1 | 2/2006 |
| WO | WO 2006/088833 A2 | 8/2006 |
| WO | WO 2006/108405 A2 | 10/2006 |
| WO | WO 2006/138145 A1 | 12/2006 |
| WO | WO 2007/008463 A2 | 1/2007 |
| WO | WO 2007/044851 A2 | 4/2007 |
| WO | WO 2007/047455 A2 | 4/2007 |
| WO | WO 2007/055682 A2 | 5/2007 |
| WO | WO 2007/055704 A2 | 5/2007 |
| WO | WO 2007/064857 A2 | 6/2007 |
| WO | WO 2007/089607 A2 | 8/2007 |
| WO | WO 2007/096134 A1 | 8/2007 |
| WO | WO 2007/122405 A1 | 11/2007 |
| WO | WO 2008/014979 A2 | 2/2008 |
| WO | WO 2008/42156 A1 | 4/2008 |
| WO | WO 2008/097328 A2 | 8/2008 |
| WO | WO 2008/127789 A2 | 10/2008 |
| WO | WO 2009/012786 A2 | 1/2009 |
| WO | WO 2009/026412 A1 | 2/2009 |
| WO | WO 2009/051451 A2 | 4/2009 |
| WO | WO 2009/061515 A1 | 5/2009 |
| WO | WO 2009/105260 A2 | 8/2009 |
| WO | WO 2009/120887 A2 | 10/2009 |
| WO | WO 2010/017152 A2 | 2/2010 |
| WO | WO 2010/017154 A2 | 2/2010 |
| WO | WO 2010/060110 A1 | 5/2010 |
| WO | WO 2010/081049 A1 | 7/2010 |
| WO | WO 2010/081049 A2 | 7/2010 |
| WO | WO 2010/091293 A1 | 8/2010 |
| WO | WO 2010/105209 A1 | 9/2010 |
| WO | WO 2010/120420 A1 | 10/2010 |
| WO | WO 2010/148249 A1 | 12/2010 |
| WO | WO 2011/017456 A2 | 2/2011 |
| WO | WO 2011/017690 A2 | 2/2011 |
| WO | WO 2011/037973 A1 | 3/2011 |
| WO | WO 2010/147387 A3 | 5/2011 |
| WO | WO 2011/053940 A2 | 5/2011 |
| WO | WO 2011/079290 A1 | 6/2011 |
| WO | WO 2011/091065 A2 | 7/2011 |
| WO | WO 2011/113054 A2 | 9/2011 |
| WO | WO 2011/143608 A1 | 11/2011 |
| WO | WO 2012/084991 A1 | 6/2012 |
| WO | WO 2013/012628 A2 | 1/2013 |
| WO | WO 2013/049941 A1 | 4/2013 |
| WO | WO 2013/086207 A1 | 6/2013 |
| WO | WO 2013/151771 A1 | 10/2013 |
| WO | WO 2013/177419 A1 | 11/2013 |
| WO | WO 2014/025795 A1 | 2/2014 |
| WO | WO 2014/123935 A1 | 8/2014 |
| WO | WO 2014/133547 A1 | 9/2014 |
| WO | WO 2014/169264 A2 | 10/2014 |
| WO | WO 2014/172698 A1 | 10/2014 |
| WO | WO 2014/175836 A1 | 10/2014 |
| WO | WO 2014/201245 A1 | 12/2014 |
| WO | WO 2015/153975 A1 | 10/2015 |
| WO | WO 2015/187966 A1 | 12/2015 |
| WO | WO 2015/195628 A2 | 12/2015 |
| WO | WO 2016/057898 A1 | 4/2016 |
| WO | WO 2016/081503 A1 | 5/2016 |
| WO | WO 2016/115320 A1 | 7/2016 |
| WO | WO-2016134104 A1 * | 8/2016 ............ A61P 37/02 |
| WO | WO 2016/179475 A1 | 11/2016 |
| WO | WO 2016/187122 A1 | 11/2016 |
| WO | WO 2017/024296 A1 | 2/2017 |
| WO | WO 2017/035278 A1 | 3/2017 |
| WO | WO 2017/075477 A1 | 5/2017 |
| WO | WO 2017/085248 A1 | 5/2017 |
| WO | WO 2017/160717 A2 | 9/2017 |
| WO | WO 2017/161032 A1 | 9/2017 |
| WO | WO 2017/173334 A1 | 10/2017 |
| WO | WO 2017/181128 A1 | 10/2017 |
| WO | WO 2017/185180 A1 | 11/2017 |
| WO | WO 2017/186815 A1 | 11/2017 |
| WO | WO 2017/223085 A2 | 12/2017 |
| WO | WO 2017/223422 A1 | 12/2017 |
| WO | WO 2018/007475 A1 | 1/2018 |
| WO | WO 2018/053242 A1 | 3/2018 |
| WO | WO 2018/053508 A1 | 3/2018 |
| WO | WO 2018/067302 A2 | 4/2018 |
| WO | WO 2018/078620 A1 | 5/2018 |
| WO | WO 2018/087699 A2 | 5/2018 |
| WO | WO 2018/152327 A1 | 8/2018 |
| WO | WO 2018/156617 A2 | 8/2018 |
| WO | WO 2018/191746 A1 | 10/2018 |
| WO | WO 2018/193137 A1 | 10/2018 |
| WO | WO 2018/198076 A1 | 11/2018 |
| WO | WO 2018/203833 A1 | 11/2018 |
| WO | WO 2018/209270 A1 | 11/2018 |
| WO | WO 2018/211453 A1 | 11/2018 |
| WO | WO 2018/213585 A1 | 11/2018 |
| WO | WO 2018/227116 A1 | 12/2018 |
| WO | WO 2019/006371 A1 | 1/2019 |
| WO | WO 2019/036031 A2 | 2/2019 |
| WO | WO 2019/038671 A1 | 2/2019 |
| WO | WO 2019/118883 A2 | 6/2019 |

OTHER PUBLICATIONS

[No Author Listed] KeraFAST Chemoselective ligation through copper-free click chemistry. Sep. 21, 2021. published online via http://www.kerafast.com/PDF/Chemoselective_Ligation_Sheet.pdf 2 pages.

Agasti et al., Photoregulated release of caged anticancer drugs from gold nanoparticles, J. Am. Chem. Soc. 2009; 131(16):5728-9.

Agbasi-Porter et al., Transcription inhibition using oligonucleotide-modified gold nanoparticles, Bioconjugate Chem., 17(5):1178-83 (2006).

Agrawal et al., Antisence therapeutics: Is it as simple as complementary base recognition? Mol. Med. Today. 2000; 6: 72-81.

Ahmadi et al., Shape-Controlled Synthesis of Colloidal Platinum Nanoparticles. Science. 1996; 272(5270): 1924-1926.

Alemdaroglu et al., DNA Block Copolymer Micelles—A Combinatorial Tool for Cancer Nanotechnology. Advanced Materials. Mar. 2008;20(5)899-902. https://doi.org/10.1002/adma.200700866l.

Ali et al., Vaccines Combined with Immune Checkpoint Antibodies Promote Cytotoxic T-cell Activity and Tumor Eradication. Cancer Immunol Res. Feb. 2016;4(2):95-100. Doi: 10.1158/2326-6066.CIR-14-0126. Epub Dec. 15, 2015.

Alivisatos et al., Organization of 'nanocrystal molecules' using DNA. Nature. 1996; 382: 609-11.

Alivisatos, The use of nanocrystals in biological detection. Nat. Biotechnol. 2004; 22(1):47-52.

Andrews et al., Conjugation of Lipid and CpG-Containing Oligonucleotide Yields an Efficient Method for Liposome Incorporation. Bioconjuqate Chem. 2011;22:1279-1286.

Anton et al., Design and production of nanoparticles formulated from nano-emulsion templates-a review. J. Control Release. 2008; 128(3):185-99.

Asthana et al., Mannosylated chitosan nanoparticles for delivery of antisense oligonucleotides for macrophage targeting. Biomed Res Int. 2014;2014:526391. Doi: 10.1155/2014/526391. Epub Jun. 26, 2014.

Aurasense Therapeutics, NIH grant. Topically-delivered Target Gene Suppression of Immune Activation in Psoriasis. David Giljohann. Accessed on Aug. 2, 2017 from http://grantome.com/grant/NIH/R41-AR066438-01. Accessible online on Feb. 21, 2016 as verified through Wayback Machine.

Auyeung et al., DNA-mediated nanoparticle crystallization into Wulff polyhedral. Nature 505(7481): 73-77 (2014).

Auyeung et al., Synthetically programmable nanoparticle superlattices using a hollow three dimensional; spacer approach. Nat Nanotechnol;2012;7(1 ):24-28.

(56) References Cited

OTHER PUBLICATIONS

Auyeung et al., Transitioning DNA-Engineered Nanoparticle Superlattices from Solution to the Solid State. Adv Mater 24(38):5181-5186 (2012).
Aynie et al., Spongelike alginate nanoparticles as a new potential system for the delivery of antisense oligonucleotides. Antisense Nucl. Acid Drug Dev. 1999; 9: 301-12.
Bae et al., Targeted drug delivery to tumors: myths, reality and possibility. J Control Release. Aug. 10, 2011; 153(3): 198-205. Doi: 10.1016/j.jconrel.2011.06.001. Epub Jun. 6, 2011.
Baker et al., Dendrimer-mediated cell transfection in vitro. Meth. Malec. Biol. 2004;245: 67-81.
Balasubramanian et al., Biodistribution of gold nanoparticles and gene expression changes in the liver and spleen after intravenous administration in rats. Biomaterials. 2010;31(8):2034-42.
Bath et al., DNA nanomachines. Nat. Nanotechnol. 2007;2:275-84.
Berton et al., Highly loaded nanoparticulate carrier using an hydrophobic antisense oligonucleotide complex. Eur. J. Pharma. Sci. 1999;9:163-70.
Bharali et al., Organically modified silica nanoparticles: a nonviral vector for in vivo gene delivery and expression in the brain. Proc. Natl. Acad. Sci. USA. 2005;102(32): 11539-44.
Bhattarai et al., "Enhanced Gene and siRNA Delivery by Polycation-Modified Mesoporous Silica Nanoparticles Loaded with Chloroquine," Pharm. Res., 2010, 27, 2556-2568.
Bielinska et al., DNA complexing with polyamidoamine dendrimers: implications for transfection. Bioconjug Chem. 1999;10(5): 843-50.
Bisht et al., Polymeric nanoparticle-encapsulated curcumin ("nanocurcumin"): a novel strategy for human cancer therapy. J. Nanobiotechnology. 2007;5:3. 18 pages.
Bonoiu et al., Nanotechnology approach for drug addiction therapy: gene ; silencing using delivery of gold nanorod-siRNA nanoplex in dopaminergic neurons. Proc Natl Acad Sci U S A. Apr. 7, 2009;106(14):5546-50. Doi:; 10.1073/pnas.0901715106. Epub Mar. 23, 2009.
Boudreault et al., Nanoscale tools to selectively destroy cancer cells. Chem Commun. May 14, 2008;(18):2118-20. Doi: 10.1039/b800528a. Epub Apr. 7, 2008.
Briley et al., In Nanomaterials for Biomedicine; American Chemical Society. 2012;1119:1-20.
Brown et al., Surface treatment of the hydrophobic drug danazol to improve drug dissolution. Int. J. Pharmaceutics. 1998;165:227-37.
Bunge et al., Lipophilic oligonucleotides spontaneously insert into lipid membranes, bind complementary DNA strands, and sequester into lipid-disordered domains. Langmuir. Apr. 10, 2007;23(8):4455-64. Epub Mar. 17, 2007.
Cao et al., Reversible Cell-Specific Drug Delivery with Aptamer-Functionalized Liposomes, Anqew. Chem. Int. Ed. 2009;48:6494-8.
Capaccioli et al., Cationic lipids improve antisense oligonucleotide uptake and prevent degradation in cultured cells and inhuman serum. Biochem. Biophys. Res. Commun. 1993;197(2): 818-25.
Castoldi et al., A sensitive array for micro RNA expression profiling (miChip) based on locked nucleic acids (LNA). RNA. 2006;12: 913-20.
Charreyre et al., Fluorescence energy transfer study of the conformation of oligonucleotides covalently bound to polystyrene latex particles. Langmuir. 1997; 13: 3103-10.
Chavany et al., Polyalkylcyanoacrylate nanoparticles as polymeric carriers for antisense oligonucleotides. Pharma. Res. 1992;9(4): 441-9.
Chavany, et al., Adsorption of oligonucleotides onto polyisohexylcyanoacrylate nanoparticles protects them against nucleases and increases their cellular uptake. Pharma. Res. 1994;11(9): 1370-8.
Chen et al., Ionic strength-dependent persistence lengths of single-stranded RNA and DNA. Proc Natl Acad Sci USA. 2012;109:799-804.
Chen et al., Kinetics and thermodynamics of DNA hybridization on gold nanoparticles. Nucleic Acids Res. Jun. 2009;37(11):3756-65. Doi: 10.1093/nar/gkp230. Epub Apr. 20, 2009.
Chen et al., Nanoparticle-aptamer: an effective growth inhibitor for human cancer cells. IMECE 2009-11966. Jul. 8, 2010;271 -2. https://doi.org/10.1115/IMECE2009-11966. 2 pgs.
Cheng et al., Interdigitated phospholipid/alkanethiol bilayers assembled on APTMS-supported gold colloid electrodes. Electroanalysis. 2004;16(1-2):127-31. Doi: 10.1002/elan.200302929.
Cheng et al., Tandem synthesis of core-shell brush copolymers and their transformation to peripherally cross-linked and hollowed nanostructures. J Am Chem Soc. May 31, 2006; 128(21):6808-9. Published on web May 6, 2006.
Chinen et al., Spherical nucleic acid nanoparticle conjugates enhance G-quadruplex formation and increase serum protein interactions. Angew Chem Int Ed Engl. Jan. 7, 2015;54(2):527-31. Doi: 10.1002/anie.201409211. Epub Nov. 13, 2014.
Chinnathambi et al., Binding mode of CpG Oligodeoxynucleotides to nanoparticles regulates bifurcated cytokine induction via Toll-like Receptor 9. Sci Reports. 2012;2(534):1-9.
Chirila et al., The use of synthetic polymers for delivery of therapeutic antisense oligodeoxynucleotides. Biomaterials. 2002;23: 321-42.
Chithrani et al., Determining the size and shape dependence of gold nanoparticle uptake into mammalian cells. Nano Lett. 2006;6(4):662-8.
Cho et al., Immunostimulatory DNA-based vaccines induce cytotoxic lymphocyte activity by a T-helper cell-independent mechanism. Nature Biotechnol. May 2000;18:509-14.
Cho et al., Targeted delivery of siRNA-generating DNA nanocassettes using multifunctional nanoparticles. Small. Jun. 10, 2013;9(11):1964-73. Doi: 10.1002/smll.201201973. Epub Jan. 6, 2013.
Cho et al., Therapeutic nanoparticles for drug delivery in cancer. Clin Cancer Res. Mar. 1, 2008;14(5):1310-6. Doi: 10.1158/1078-0432.CCR-07-1441.
Choi et al., DNA aptamer-passivated nanocrystal synthesis: a facile approach for nanoparticle-based cancer cell growth inhibition. Small. Mar. 2009;5(6):672-5. Doi: 10.1002/smll.200801821.
Chrisey et al., Covalent attachment of synthetic DNA to self-assembled monolayer films. Nucl. Acids Res. 1996;24: 3031-9.
Cload et al., Polyether tethered oligonucleotide probes. J. Am. Chem. Soc. 1991;113(16): 6324-6.
Concise Encyclopedia of Polymer Science and Engineering, "Polynucleotides," J. I. Kroschwitz Ed., John Wiley & Sons, pp. 858-859 (1990).
Cook, Medicinal chemistry of antisense oligonucleotides-future opportunities, Anti-Cancer Drug Design, 6:585-607 (1991).
Coyle et al., DNA-Mediated Assembly of Protein Heterodimers on Membrane Surfaces. J Am Chem Soc 135(13):5012-5016 (2013).
Crooke et al., Progress in antisense technology. Ann. Rev. Med. 2004;55: 61-95.
Crooke, S. T. and Lebleu, B., Ed., CRC Press "Antisense Research and Applications" Table of Contents. 1993.
Cui et al., Topical immunization using nanoengineered genetic vaccines. J Control Release. May 17, 2002;81(1-2):173-84.
Cutler et al., Polyvalent nucleic acid nanostructures. J Am Chem Soc. Jun. 22, 2011;133(24):9254-7. Doi:10.1021/ja203375n. Epub Jun. 1, 2011.
Dave et al., Programmable assembly of DNA-functionalized liposomes by DNA. ACS Nano. Feb. 22, 2011;5(2):1304-12. Doi: 10.1021/nn1030093. Epub Jan. 4, 2011.
De Mesmaeker et al., Antisense oligonucleotides. Acc. Chem. Res. 1995;28(9): 366-74.
De Mesmaeker et al., Backbone modifications in oligonucleotides and peptide nucleic acid systems, Curr. Opin. In Struct. Biol., 5: 343-55 (1995).
Deering et al., Nucleic acid vaccines: prospects for non-viral delivery of mRNA vaccines. Expert Opin Drug Deliv. Jun. 2014;11(6):885-99. Doi: 10.1517/17425247.2014.901308. Epub Mar. 26, 2014. Review.

(56) References Cited

OTHER PUBLICATIONS

Demers et al., Thermal Desorption Behavior and Binding Properties of DNA Bases and Nucleosides on Gold. J. Am. Chem. Soc. 2002;124:11248-11249.

Dhar et al., Polyvalent oligonucleotide gold nanoparticle conjugates as delivery vehicles for platinum (IV) warheads. J Am Chem Soc. Oct. 21, 2009;131(41):14652-3. Doi: 10.1021/ja907182.

Diebold et al., Nucleic acid agonists for Toll-like receptor 7 are defined by the presence of uridine ribonucleotides. Eur J Immunol. Dec. 2006;36(12):3256-67.

Dreyfus et al., Simple quantitative model for the reversible associate of DNA coated colloids. Phys. Rev. Lett. 2009;102: 048301.

Durand et al., Circular dichroism studies of an oligodeoxyribonucleotide containing a hairpin loop made of a hexaethylene glycol chain: conformation and stability. Nucl. Acids Res. 1990;18(21): 6353-9.

Dykxhoorn et al., Killing the messenger: short RNAs that silence gene expression. Nat. Rev. Mol. Cell Biol. 2003;4(6):457-67.

Eckstein, Oligonucleotides and Analogues, 1st Ed. (Oxford University Press, New York) (1991).

Elaissari et al., Effect of charge nature on the adsorption of single-stranded DNA fragments onto latex particles. J. Colloid Interface Sci. 1998;202: 251-60.

Elbakry, A. et al., "Layer-by-Layer Assembled Gold Nanoparticles for siRNA Delivery," Nano Lett., 2009, 9 (5), 2059-2064.

Elghanian et al., Selective colorimetric detection of polynucleotides based on the distance-dependent optical properties of gold nanoparticles. Science. 1997;277(5329):1078-81.

Eltekova et al., Adsorption of aromatic compounds from solutions in titanium dioxide and silica. Langmuir. 1687;3:951-7.

Eltoukhy et al., Nucleic acid-mediated intracellular protein delivery by lipid-like nanoparticles. Biomaterials. Aug. 2014;35(24):6454-61. Doi: 10.1016/j.biomaterials.2014.04.014. Epub May 13, 2014.

Fahy et al., Design and synthesis of polyacrylamide-based oligonucleotide supports for use in nucleic acid diagnostics. Nucl. Acids Res. 1993;21: 1819-26.

Fan, H. et al., "Self-Assembly of Ordered, Robust, Three-Dimensional Gold Nanocrystal/Silica Arrays," Science, 2004, 403, 567-571.

Farokhzad et al., Nanomedicine: developing smarter therapeutic and diagnostic modalities, Drug Delivery Rev., 58:1456 (2006).

Fattal et al., Biodegradable polyalkylcyanoacrylate nanoparticles for the delivery of oligonucleotides. J. Controlled Release. 1998;53:137-143.

Ferentz et al., Disulfide-crosslinked oligonucleotides. J. Am. Chem. Soc. 1991;113(10): 4000-2.

Forsbach et al., Identification of RNA sequence motifs stimulating sequence-specific TLR8-dependent immune responses. J Immunol. Mar. 15, 2008;180(6):3729-38.

Frens, Particle size and sol stability in metal colloids. Kolloid-Zeitschrift und Zeitschrift fur Polymere. 1972;250(7):736-41.

Fukuda et al., Effective transformation of unactivated alkynes into ketones or acetals by means of Au(III) catalyst. J. Org. Chem. 1991;56(11):3729-31.

Fukuda et al., Efficient transformation of methyl propargyl ethers into alpha, beta-unsaturated ketones. Bull. Chem. Soc. Jpn. 1991;64:2013-5.

Furstner et al., Catalytic carbophilic activation: catalysis by platinum and gold pi acids. Angew Chem Int Ed Engl.. 2007;46(19):3410-49.

Gao et al., Secondary structure effects on DNA hybridization kinetics: a solution versus surface comparison. Nucl. Acids Res. 2006;34: 3370-7.

Gehring et al., A tetrameric DNA structure with protonated cytosine-cytosine base pairs. Nature. 1993;363:561-565.

Ghosh et al., Gold nanoparticles in delivery applications. Adv. Drug Deliv. Rev. 2008;60(11):1307-15.

Gibson et al., Paclitaxel-functionalized gold nanoparticles. J. Am. Chem. Soc. 2007; 129(37):11653-61.

Gidwani et al., Hybridization kinetics of double-stranded DNA probes for rapid molecular analysis. Analyst. 2009;134: 1675-81.

Cigler et al., "DNA-controlled assembly of a NaTl lattice structure from gold and protein nanoparticles," Nat Mater 9(11): 918-922 (2010).

Giljohann et al., Gene regulation with polyvalent siRNA-nanoparticle conjugates. J Am Chem Soc. Feb. 18, 2009;131(6):2072-3.

Giljohann et al., Gold nanoparticles for biology and medicine. Angew Chem Int Ed Engl. Apr. 26, 2010;49(19):3280-94. Doi: 10.1002/anie.200904359.

Giljohann et al., Oligonucleotide loading determines cellular uptake of DNA-modified gold nanoparticles. Nano Lett. Dec. 2007;7(12):3818-21. Epub Nov. 13, 2007.

Gissot et al., Nucleoside, nucleotide and oligonucleotide based amphiphiles: a successful marriage of nucleic acids with lipids. Org. Biomol. Chem. 2008;6:1324-33.

Godard, G. et al., "Antisense Effects of Cholesterol-Oligodeoxynucleotide Conjugates Associated with Poly(alkylcyanoacrylate) Nanoparticles," Eur. J. Biochem., 1995, 232 (2), 404-410.

Grabar et al., Preparation and characterization of Au colloid monolayers. Anal. Chem. 1995;67:735-43.

Gramzinski et al., Interleukin-12 and gamma interferon-dependent protection against malaria conferred by CpG oligodeoxynucleotide in mice. Infection and Immunity. Mar. 2001:1643-9.

Grijalvo et al., Oligonucleotide delivery: a patent review (2010-2013). Expert Opin Ther Pat. Jul. 2014;24(7):801-19. Doi:10.1517/13543776.2014.915944. Epub May 5, 2014.

Gryaznov, Oligonucleotide n3'→p5' phosphoramidates and thiophosphoramidates as potential therapeutic agents. Chem Biodivers. Mar. 2010;7(3):477-93. Doi: 10.1002/cbdv.200900187. Review.

Guiducci et al., Properties regulating the nature of the plasmacytoid dendritic cell response to Toll-like receptor 9 activation. J Exp Med. Aug. 7, 2006;203(8):1999-2008. Epub Jul. 24, 2006.

Hames et al., Gene Probes 1 A Practical Approach, IRL Press, New York (1995).

Hamilton et al., A species of small antisense RNA in post-transcriptional gene silencing in plants. Science. 1999;286: 950-2.

Hammond et al., An RNA-directed nuclease mediates post-transcriptional gene silencing in Drosophilia cells. Nature. 2000;404: 293-6.

Han et al., A gold nanoparticle based approach for screening triplex DNA binders. J. Am. Chem. Soc. 2006;128(15):4954-5.

Han et al., Drug and gene delivery using gold nanoparticles. NanoBiotechnology. Mar. 2007;3(1):40-5.

Hartmann et al., Delineation of a CpG phosphorothioate oligodeoxynucleotide for activating primate immune responses in vitro and in vivo. J Immunol. Feb. 1, 2000 ;164(3): 1617-24.

Hashmi et al., Gold catalysis. Angew Chem Int Ed Engl. 2006;45(47):7896-936.

Hashmi et al., Gold-catalyzed organic reactions. Chem. Rev. 2007;107:3180-211.

Hayashi, Ultrafine particles. J. Vac. Sci. Technol. 1987;5(4):1375-1384.

Hayat, (Ed.) Colloidal Gold: Principles, Methods, and Applications, vol. 1, Table of Contents, pp. v-xvii; vol. 2, Table of Contents pp. v-xix; vol. 3, Table of Contents, ppv-xiv, Academic Press, San Diego (1989-1991).

He et al., Colloidal Au-enhanced surface plasmon resonance for ultrasensitive detection of DNA hybridization. J. Am. Chem. Soc. 2000;122(38): 9071-7.

He et al., Phospholipid-stabilized Au-nanoparticles. Biomacromolecules. May 2005-Jun.;6(3):1224-5.

Hegner et al., Modified DNA immobilized on bioreactive self-assembled monolayer on gold for dynamic force microscopy imaging in aqueous buffer solution. J. Vac. Sci. Technol. B, 1996;14(2):1418-21.

Heil et al., Species-specific recognition of single-stranded RNA via toll-like receptor 7 and 8. Science. Mar. 5, 2004;303(5663):1526-9. Epub Feb. 19, 2004.

Hellstrom et al., Epitaxial growth of DNA-assembled nanoparticle superlattices on patterned substrates. Nano Lett. 2013;13(12):6084-90. Doi: 10.1021/nl4033654. Epub Nov. 20, 2013.

(56) References Cited

OTHER PUBLICATIONS

Henglein, "Small-Particle Research: Physicochemical Properties of Extremely Small Colloidal Metal and Semiconductor Particles," Chem. Rev., 89:1861-1873 (1989).
Henglein, Mechanism of Reactions on Colloidal Microelectrodes and Size Quantization Effects. Top. Curr. Chem. 1988;143:113-180.
Hill et al., "Controlling the Lattice Parameters of Gold Nanoparticle FCC Crystals with Duplex DNA Linkers," Nano Lett 8(8): 2341-2344 (2008).
Holen et al., Positional effects of short interfering RNAs targeting the human coagulation trigger tissue factor. Nucl. Acids Res. 2002;30: 1757-66.
Hotz et al., VEGF antisense therapy inhibits tumor growth and improves survival in experimental pancreatic cancer. Surgery. Feb. 2005;137(2):192-9.
Houot et al., T-cell modulation combined with intratumoral CpG cures lymphoma in a mouse model without the need for chemotherapy. Blood. Apr. 9, 2009; 113(15):3546-52. Doi: 10.1182/blood-2008-07-170274. Epub Oct. 21, 2008.
Hussain et al., A novel anionic dendrimer for improved cellular delivery of antisense oligonucleotides. J. Controlled Rel. 2004;99: 139-55.
Huxley et al., Preferential Staining of Nucleic Acid-Containing Structures for Electron Microscopy. J Biophys Biochem Cytol 1961;11:273-296 (1961).
Hwu et al., Targeted Paclitaxel by conjugation to iron oxide and gold nanoparticles. J. Am. Chem. Soc.. 2009;131(1):66-8.
Iler, The surface chemistry of silica (chapter 6), IN: ILER, Chemistry of Silica, New York: John Wiley & Sons (1979).
Jackson et al., How do microRNAs regulate gene expression? Sci STKE. 2007(367):re1.
Jaschke et al., Automated incorporation of polyethylene glycol in synthetic oligonucleotides. Tetrahedron Lett. 1993;34: 301-4.
Jason et al., Toxicology of antisense therapeutics. Toxicol. Appl. Pharmacol. 2004;201(1): 66-83.
Jen et al., A nonviral transfection approach in vitro: the design of a gold nanoparticle vector joint with microelectromechanical systems. Langmuir, 2004;20(4): 1369-74.
Jensen et al., Spherical nucleic acid nanoparticle conjugates as an RNAi-based therapy for glioblastoma, Sci. Trans. Med., 5:209ra152 (2013).
Jeong et al., Novel intracellular delivery system of antisense oligonucleotide by self-assembled hybrid micelles composed of DNA/PEG conjugate and cationic fusogenic peptide. Bioconjugate Chem. 2003; 14: 473-9.
Jin et al., What controls the melting properties of DNA-linked gold nanoparticle assemblies? J. Am. Chem. Soc. 2003;125: 1643.
Kachura et al., A CpG-Ficoll Nanoparticle Adjuvant for Anthrax Protective Antigen Enhances Immunogenicity and Provides Single-Immunization Protection against Inhaled Anthrax in Monkeys. J Immunol. Jan. 1, 2016; 196(1):284-97. Doi: 10.4049/jimmunol. 1501903. Epub Nov. 25, 2015.
Kandimalla et al., Conjugation of Ligands at the 5'-End of CpG DNA Affects Immunostimulatory Activity. Bioconjugate Chemistry 2002 13 (5), 966-974. DOI: 10.1021/bc0200374.
Kandimalla et al., Secondary structures in CpG oligonucleotides affect immunostimulatory activity. Biochem Biophys Res Commun. Jul. 11, 2003;306(4):948-53.
Kanzler et al., Therapeutic targeting of innate immunity with Toll-like receptor agonists and antagonists. Nat Med. May 2007;13(5):552-9.
Katz et al., Integrated nanoparticle-biomolecule hybrid systems: synthesis, properties, and applications. Angew. Chem. Int. Ed. 2004;43: 6042-108.
Kawasaki et al., Toll-like receptor signaling pathways. Front Immunol. Sep. 25, 2014;5:461. Doi: 10.3389/fimmu.2014.00461. eCollection 2014. Review.
Khmelinskaia et al., Effect of anchor positioning on binding and diffusion of elongated 3D DNA nanostructures on lipid membranes. J. Phys. D: Appl. Phys. Apr. 13, 2016;49(19): 194001.

Kim et al., Cationic solid lipid nanoparticles reconstituted from low density lipoprotein components for delivery of siRNA. Mol Pharm. Jul. 2008-Aug.;5(4):622-31. Doi: 10.1021/mp8000233. Epub May 8, 2008.
Kim et al., Direct synthesis of polymer nanocapsules with a noncovalently tailorable surface. Angew. Chem. Int. Ed. Engl. 2007;46(19):3471-4.
Kim et al., Direct synthesis of polymer nanocapsules: self-assembly of polymer hollow spheres through irreversible covalent bond formation. J. Am. Chem. Soc. 2010;132(28):9908-19.
Kim et al., Effect of bovine serum albumin on the stability of methotrexate-encapsulated liposomes, Arch. Pharmacal Res. 1991;14:336.
Kim et al., Facile, template-free synthesis of stimuli-responsive polymer nanocapsules for targeted drug delivery. Angew. Chem. Int. Ed. Engl. 2010;49(26):4405-8.
Kim, S. et al., "Systemic and Specific Delivery of Small Interfering RNAs to the Liver Mediated by Apolipoprotein A-I," Mol. Ther., 2007, 15 (6), 1145-1152.
Kimura-Suda et al., Base-Dependent Competive Adsorption of Single-Stranded DNA on Gold. Journal of the American Chemical Society. 2003; 125: 9014-9015.
Kloosterman et al., In situ detection of miRNAs in animal embryos using LNA-modified oligonucleotide probes. Nat. Methods. 2006;3: 27-9.
Kolarova et al., Preparation of magnetic oligo (dT) particles. Biotechniques. 1996;20: 196-8.
Kondo et al., Nano tube formation through the continuous one-dimensional fusion of hollow nanocapsules composed of layer-by-layer poly(lactic acid) stereocomplex films. J. Am. Chem. Soc. 2010;132(24):8236-7.
Kong et al., Cationic lipid-coated gold nanoparticles as efficient and non-cytotoxic intracellular siRNA delivery vehicles. Pharm Res. Feb. 2012;29(2):362-74. Doi: 10.1007/s11095-011-0554-y. Epub Aug. 13, 2011.
Krieg, Toll-like receptor 9 (TLR9) agonists in the treatment of cancer.; Oncogene. Jan. 7, 2008;27(2): 161-7. Doi: 10.1038/sj.onc. 1210911.
Krieg. Antiinfective applications of toll-like receptor 9 agonists. Proc Am Thorac Soc. Jul. 2007;4(3):289-94.
Krug et al. Identification of CpG oligonucleotide sequences with high induction of IFN-alpha/beta in plasmacytoid dendritic cells. Eur J Immunol. Jul. 2001;31(7):2154-63.
Krutzfeldt et al., Silencing of microRNAs in vivo with 'antagomirs'. Nature. 2005;438(7068):685-9.
Kukowska-Latallo et al., "Efficient transfer of genetic material into mammalian cells using Starburst polyamidoamine dendrimers," Proc. Natl. Acad. Sci. USA 93:4897-4902 (1996).
Kwoh et al., Stabilization of poly-L-lysine/DNA polyplexes for in vivo gene delivery to the liver. Biochim Biophys Acta. Feb. 16, 1999;1444(2):171-90.
Landfester et al., From polymeric particles to multifunctional nanocapsules for biomedical applications using the miniemulsion process. J. Polymer Sci. Part A.2010; 48(3)493-515.
Langer, New methods of drug delivery. Science. Sep. 28, 1990;249(4976):1527-33.
Leander, D., "Mixed-Monolayer Gold Nanoparticles for Cancer Therapeutics," Nanoscape, 2010, 7(1), 11-14.
Lebedeva et al., Antisense oligonucleotides: Promise and reality. Annu. Rev. Pharmacol. Toxicol. 2001;41:403-19.
Lee et al., A DNA-Gold Nanoparticle-Based Colorimetric Competition Assay for the Detection of Cysteine. Nano Letter. 2008;8(2):529-533.
Lee et al., All-in-one target-cell-specific magnetic nanoparticles for simultaneous molecular imaging and siRNA delivery. Angew Chem Int Ed Engl. 2009;48(23):4174-9. Doi: 10.1002/anie.200805998.
Lee et al., Chip-based scanometric detection of mercuric ion using DNA-functionalized gold nanoparticles. Anal. Chem. 2008;80(17):6805-8.
Lee et al., Colorimetric detection of mercuric ion (Hg2+) in aqueous media using DNA-functionalized gold nanoparticles. Angew Chem Int Ed Engl. 2007;46(22):4093-6.

(56) References Cited

OTHER PUBLICATIONS

Lee et al., Silver nanoparticle-oligonucleotide conjugates based on DNA with triple cyclic disulfide moieties, Nano Lett., 7: 2112 (2007).

Leleux et al., Biophysical Attributes of CpG Presentation Control TLR9 Signaling to Differentially Polarize Systemic Immune Responses. Cell Rep. Jan. 17, 2017;18(3):700-710. Doi: 10.1016/j.celrep.2016.12.073.

Lemaigre et al., Transcriptional control of genes that regulate glycolysis and gluconeogenesis in adult liver. Biochem. J. 1994;303:1-14.

Lennox et al., Characterization of modified antisense oligonucleotides in Xenopus laevis embryos. Oligonucleotides. 2006 Spring;16(1):26-42.

Leslie et al., A new tool for oligonucleotides import into cells. Clin. Chem. 009;55: 609-10.

Leunissen et al., Switchable self-protected attractions in DNA-functionalized colloids. Nat. Mater. 2009;8: 590-95.

Lewandowski et al., Topically delivered spherical nucleic acid nanoconjugates targeting TNF improve the psoriatic phenotype. J Invest Dermatol. 2015 135:S71. Abstract 413.

Lewis, Controlled release of bioactive agents from lactide/glycolide polymer. pp. 1-41, in Chasin et al. (eds.), Biodegradable Polymers as Drug Delivery Systems, Marcel Dekker (1990).

Li et al., Combination delivery of antigens and CpG by lanthanides-based core-shell nanoparticles for enhanced immune response and dual-mode imaging. Adv Healthc Mater. Oct. 2013;2(10):1309-13. Doi:10.1002/adhm.201200364. Epub Mar. 25, 2013.

Li et al., Dual-reactive surfactant used for synthesis of functional nanocapsules in miniemulsion. J. Am. Chem. Soc. 2010;132(23):7823-5.

Li et al., Gold-catalyzed organic transformations. Chem. Rev. 2008;108(8):3239-65.

Li et al., Nanofabrication by DNA self-assembly. Materials Today. Elsevier Science. May 1, 2009; 12(5)24-32.

Li et al., Nucleolin-targeting liposomes guided by aptamer AS1411 for the delivery of siRNA for the treatment of malignant melanomas. Biomaterials. Apr. 2014;35(12):3840-50. Doi: 10.1016/j.biomaterials.2014.01.019. Epub Jan. 31, 2014.

Li et al., Reversible and chemically programmable micelle assembly with DNA block-copolymer amiphiphiles. Nano Lett.. 2004;4(6):1055-8.

Li et al., Thermal stability of DNA functionalized gold nanoparticles, Bioconjugate Chem., 24:1790-7 (2013).

Lin et al., Gold nanoparticle delivery of modified CpG stimulates macrophages and inhibits tumor growth for enhanced immunotherapy. PloS One. May 15, 2013;8(5):e63550. Doi: 10.1371/journal.pone.0063550. Print 2013.

Lipshutz et al., High density synthetic oligonucleotide arrays. Nanotechnology. 2003; 14: R15-27.

Liu et al., DNA-based micelles: synthesis, micellar properties and size-dependent cell permeability, Chemistry. 2010;16:3791-7.

Liu et al., Membrane anchored immunostimulatory oligonucleotides for in vivo cell modification and localized immunotherapy. Angew Chem Int Ed Engl. Jul. 25, 2011;50(31):7052-5. Doi: 10.1002/anie.201101266. Epub Jun. 17, 2011.

Liu et al., New poly(d-glucaramidoamine)s induce DNA nanoparticle formation and efficient gene delivery into mammalian cells. J. Am. Chem. Soc. 2004; 126: 7422-3.

Liu et al., Structure-based programming of lymph-node targeting in molecular vaccines. Nature. Mar. 27, 2014;507(7493):519-22. Doi: 10.1038/nature12978.

Liu, J. et al., Silica Nanoparticle Supported Lipid Bilayers for Gene Delivery, Chem. Commun., 2009, 5100-5102.

Ljubimova et al., Nanoconjugate based on polymalic acid for tumor targeting. Chem Biol Interact. Jan. 30, 2008;171(2):195-203. Epub Feb. 8, 2007.

Love et al., Self-assembled monolayers of thiolates on metals as a form of nanotechnology. Chem. Rev. 2005;105: 1103-69.

Luo et al., Synthetic DNA delivery systems. Nat Biotechnol. Jan. 2000;18(1):33-7.

Lytton-Jean et al., A thermodynamic investigation into the binding properties of DNA functionalized gold nanoparticle probes and molecular fluorophore probes. J Am Chem Soc. Sep. 21, 2005; 127(37):12754-5.

Lytton-Jean et al., Highly Cooperative Behavior of Peptide Nucleic Acid-Linked DNA-Modified Gold-Nanoparticle and Comb-Polymer Aggregates, Advanced Materials, 21: 706 (2009).

Ma et al., Design and synthesis of RNA miniduplexes via a synthetic linker approach. 2. Generation of covalently closed, double-stranded cyclic HIV-1 TAR RNA analogs with high Tat- binding affinity. Nucl. Acids Res. 1993;21: 2585-9.

Ma et al., Design and synthesis of RNA miniduplexes via a synthetic linker approach. Biochemistry. 1993;32(7): 1751-8.

Macfarlane et al., "Establishing the Design Rules for DNA-Mediated Programmable Colloidal Crystallization," Angew Chem Int Ed Engl 49(27): 4589-4592 (2010).

Macfarlane et al., "Nanoparticle Superlattice Engineering with DNA," Science 334:204-208 (2011).

Macfarlane et al., Nucleic Acid-Modified Nanostructures as Programmable Atom Equivalents: Forainq a New "Table of Elements," Anaew Chem Int Ed 52(22): 5688-5698 (2013).

Madan-Lala et al., Combinatorial Delivery of Dual and Triple TLR Agonists via Polymeric Pathogen-like Particles Synergistically Enhances Innate and Adaptive Immune Responses. Sci Rep. May 31, 2017;7(1):2530. Doi:10.1038/s41598-017-02804-y.

Mangsbo et al., Enhanced tumor eradication by combining CTLA-4 or PD-1 blockade with CpG therapy. J Immunother. Apr. 2010;33(3):225-35. Doi: 10.1097/CJI.0b013e3181c01fcb.

Maoz et al., Penetration-controlled reactions in organized monolayer assemblies. 1. Aqueous permanganate interaction with monolayer and multilayer films of long-chain surfactants. Langmuir. 1987;3:1034-44.

Maoz et al., Penetration-controlled reactions in organized monolayer assemblies. 2. Aqueous permanganate interaction with self-assembling monolayers of long-chain surfactants. Langmuir. 1987;3:1045-51.

Marabelle et al. Depleting tumor-specific Tregs at a single site eradicates disseminated tumors, J Clin Invest. 2013; 123(6):2447-2463.

Marinakos et al., Gold Nanoparticles as Templates for the Synthesis of Hollow Nanometer-Sized Conductive Polymer Capsules. Adv. Mater. 1999; 11: 34-37.

Marshall et al., Novel chimeric immunomodulatory compounds containing short CpG oligodeoxyribonucleotides have differential activities in human cells. Nucleic Acids Res. Sep. 1, 2003;31(17):5122-33.

Martinez et al., Locked nucleic acid based beacons for surface interaction studies and biosensor development. Anal. Chem. 2009;81: 3448-54.

Martinson et al., Impact of Class A, B and C CpG-oligodeoxynucleotides on in vitro activation of innate immune cells in human immunodeficiency virus-1 infected individuals. Immunology. 2007;120(4):526-35.

Maruyama, et al., Nanoparticle DNA carrier with poly(L-lysine) grafted polysaccharide copolymer and poly(D,L-lactic acid). Bioconjugate Chem.. 1997;8: 735-742.

Massich et al., Regulating immune response using polyvalent nucleic acid-gold nanoparticle conjugates. Mol Pharm. Nov. 2009-Dec.;6(6):1934-40.

Matijevic et al., Fine Particles Part II: Formation Mechanisms and Applications. MRS Bulletin pp. 16-47 (1990).

Matteucci et al., Synthesis of deoxyoligonucleotides on a polymer support. J. Am. Chem. Soc. 1981;103:3185-3191.

Mattson et al., A practical approach to crosslinking. Malec. Biol. Rep. 1993; 17: 167-83.

Maxwell et al., Self-assembled nanoparticle probes for recognition and detection of biomolecules. J. Am. Chem. Soc. 2002;124: 9606-12.

Maye et al., A simple method for kinetic control of DNA-induced nanoparticle assembly. J. Am. Chem. Soc. 2006; 128: 14020-1.

(56) References Cited

OTHER PUBLICATIONS

McAllister et al., Polymeric nanogels produced via inverse microemulsion polymerization as potential gene and antisense delivery agents, J. Am. Chem. Soc., 124:15198 (2002).

McBain, S. et al., "Polyethyleneimine Functionalized Iron Oxide Nanoparticles as Agents for DNA Deliver and Transfection," J. Mater. Chem., 2007, 17, 2561-2565.

McGehee et al., Differentiation-specific element: a cis-acting developmental switch required for the sustained transcriptional expression of the angiotensinogen gene during hormonal-induced differentiation of 3T3-L 1 fibroblasts to adipocvtes. Mol. Endocrinol. 1993;7: 551-60.

McKay et al., Characterization of a potent and specific class of antisense oligonucleotide inhibitor of human protein kinase C-alpha expression. J Biol Chem. Jan. 15, 1999;274(3): 1715-22.

McKenzie et al., Sequence-specific DNA detection using high-affinity LNA-functionalized gold nanoparticles. Small. Nov. 2007;3(11):1866-8.

McManus et al., Gene silencing in mammals by small interfering RNAs. Nat. Rev. Genet. 2002;3(10): 737-47.

Medintz et al., A reactive peptidic linker for self-assembling hybrid quantum dot-DNA bioconjugates. Nano Lett. Jun. 2007;7(6):1741-8. Epub May 26, 2007.

Mendell, MicroRNAs: critical regulators of development, cellular physiology and malignancy. Cell Cycle. 2005;4(9):1179-84.

Miller et al., Antisense oligonucleotides: Strategies for delivery. PSTT. 1998; 1(9): 377-86.

Ming et al., Albumin-based nanoconjugates for targeted delivery of; therapeutic oligonucleotides. Biomaterials. Oct. 2013;34(32):7939-49. Doi:; 10.1016/j.biomaterials.2013.06.066. Epub Jul. 19, 2013.

Mohamed et al., TLR9 mediates S. aureus killing inside osteoblasts via induction of oxidative stress. BMC Microbiol. Oct. 3, 2016;16(1):230.

Monia et al., Nuclease resistance and antisense activity of modified oligonucleotides targeted to Ha-ras. J Biol Chem. Jun. 14, 1996;271(24):14533-40.

Moughton et al., Hollow nanostructures from self-assembled supramolecular metallo-triblock copolymers. Soft Matter. 2009;5(12):2361-70.

Mucic et al., Synthesis and characterization of DNA with ferrocenyl groups attached to their 5'-termini: electrochemical characterization of a redox-active nucleotide monolayer. Chem. Comm. 1996;555-7.

Mui et al., Immune stimulation by a CpG-containing oligodeoxynucleotide is enhanced when encapsulated and delivered in lipid particles. J Pharmacol Exp Ther. Sep. 2001;298(3): 1185-92.

Niemeyer, C. et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.

Nykypanchuk et al., "DNA-guided crystallization of colloidal nanoparticles," Nature 451 :549-552 (2008).

O'Meara et al., Capture of single-stranded DNA assisted by oligonucleotide modules. Anal. Biochem. 1998;255: 195-203.

O'Reilly et al., Identification of an activating transcription factor (ATF) binding site in the human transforming growth factor-beta 2 promoter. J. Biol. Chem. 1992;267: 19938-43.

Ono et al., DNA triplex formation of oligonucleotide analogues consisting of linker groups and octamer segments that have opposite sugar-phosphate backbone polarities. Biochemistry. 1991;30(41): 9914-2.

Opalinska et al., Nucleic-acid therapeutics: basic principles and recent applications. Nat Rev Drug Discov. Jul. 2002;1(7):503-14.

Opdahl et al., Independent control of grafting density and conformation of single-stranded DNA brushes. Proc Natl Acad Sci U.S.A. 2007;104: 9-14.

Ow Sullivan et al., Development of a novel gene delivery scaffold utilizing colloidal gold-polvethylenimine coniuqates for DNA condensation. Gene Ther. 2003; 10(22): 1882-90.

Ozpolat et al., Nanomedicine based approaches for the delivery of siRNA in cancer. J. Intern. Med. 2010;267(1):44-53.

Paciotti et al., Colloidal gold: a novel nanoparticle vector for tumor directed drug delivery. Drug Deliv. 2004;11(3):169-83.

Pan et al., Dendrimer-Modified Magnetic Nanoparticles Enhance Efficiency of Gene Delivery System. Cancer Res. 2007;67:8156-8163.

Parak et al., Biological applications of colloidal nanocrystals. Nanotechnol. 2003; 14: R15-27.

Park et al., DNA-programmable nanoparticle cystrallization. Nature. 2008;451: 553-6.

Parrish et al., Functional anatomy of a dsRNA trigger: Differential requirement for the two trigger strands in RNA interference. Mol. Cell. 2000;6: 1077-87.

Parrish et al., Soluble Camptothecin Derivatives Prepared by Click Cycloaddition Chemistry on Functional Aliphatic Polyesters. Bioconjugate Chem. 2006;18: 263-267.

Patel et al., Peptide antisense nanoparticles. Proc Natl Acad Sci U S A. Nov. 11, 2008;105(45):17222-6. Doi: 10.1073/pnas.0801609105.

Patel et al., Scavenger receptors mediate cellular uptake of polyvalent oligonucleotide-functionalized gold nanoparticles, Bioconj. Chem., 21:2250 (2010).

Patil et al., DNA-based therapeutics and DNA delivery systems: a comprehensive review. AAPS J., 2005;7(1): E61-77.

Patwa et al., Hybrid lipid oligonucleotide conjugates: synthesis, self-assemblies and biomedical applications. Chem Soc Rev. 2011;40:5844-54.

Paunesku et al., Gadolinium-conjugated Ti02-DNA oligonucleotide nanoconjugates show prolonged intracellular retention period and T1 -weighted contrast enhancement in magnetic resonance images. Nanomedicine, 2008;4(3):201-7.

Peng et al., Real-time detection of gene expression in cancer cells using molecular beacon imaging: New strategies for cancer research. Cancer Res., 2005;65: 1909-17.

Penn et al., Nanoparticles for bioanalysis. Curr. Opin. Chem. Biol., 2003;7: 609-15.

Pfeiffer et al., Bivalent Cholesterol-Based Coupling of Oligonucleotides to Lipid Membrane Assemblies. J. Am. Chem. Soc. 2004;126:10224-10225.

Pfeiffer et al., Quantification of oligonucleotide modifications of small unilamellar lipid vesicles. Anal. Chem. 2006;78:7493-8.

Phan, Human telomeric G-quadruplex: structures of DNA and RNA sequences. Febs J. Mar. 2010;277(5):1107-17. Doi: 10.1111/j.1742-4658.2009.07464.x. Epub 2009; Nov. 27.

Pokholenko et al., Lipid oligonucleotide conjugates as responsive nanomaterials for drug delivery. J of Materials Chemistry B. 2013;5329-34.

Pon, Solid-phase supports for oligonucleotide synthesis. Meth. Malec. Biol., 1993;20: 465-96.

Prasad et al., Oligonucleotides tethered to a short polyguanylic acid stretch are targeted to macrophages: enhanced antiviral activity of a vesicular stomatitis virus-specific antisense oligonucleotide. Antimicrob Agents Chemother. Nov. 1999;43(11):2689-96.

Raetz J Lipid Res 2009 50:s103-s108.

Ramos-Casals et al., Autoimmune diseases induced by TNF-targeted therapies: analysis of 233 cases. Medicine (Baltimore). Jul. 2007;86(4):242-51.

Rethore et al., Preparation of chitosan/polyglutamic acid spheres based on the use of polystyrene template as nonviral gene carrier. Tissue Engineering, 2009;15(4): 605-13.

Rethore et al., Use of templates to fabricate nanoscale spherical structures for defined architectural control. Small, 2010;6(4):488-98.

Riccelli et al., Hybridization of single-stranded DNA targets to immobilized complementary DNA probes: comparison of hairpin versus linear capture probes. Nucl. Acids Res., 2001 ;29: 996-1004.

Richardson et al., Tethered oligonucleotide probes. A strategy for the recognition of structured RNA. J. Am. Chem. Soc. 1991;113(13): 5109-11.

Rosi et al., Nanostructures in biodiagnostics, Chem. Rev., 105:1547 (2005).

Rosi et al., Oligonucleotide-modified gold nanoparticles for intracellular gene regulation. Science. May 19, 2006;312(5776):1027-30.

(56) References Cited

OTHER PUBLICATIONS

Rush et al., Intracellular mRNA regulation with self-assembled locked nucleic acid polymer nanoparticles. J Am Chem Soc. May 28, 2014;136(21):7615-8. Doi: 10.1021/ja503598z. Epub May 14, 2014.
Rusling et al., "Functionalizing Designer DNA Crystals with a Triple-Helical Veneer," Angew Chem Int Ed 53(15): 3979-3982 (2014).
Santangelo et al., Nanostructured probes for RNA detection in living cells. Ann. Biomed. Eng., 2006;34:39-50.
Schifferlers et al., Cancer siRNA therapy by tumor selective delivery with ligand-targeted sterically stabilized nanoparticle. Nucl. Acid Res., 2004;32(19): e149.
Schwab et al., An approach for new anticancer drugs: Oncogene-targered antisense DNA. Ann Oncol. 1994;5(Supp14):S55-8.
Seela et al., Oligodeoxyribonucleotides containing 1,3-propanediol as nucleoside substitute. Nucl. Acids Res., 1987;15(7): 3113-29.
Seelig et al., Catalyzed relaxation of a metastable DNA fuel. J. Am. Chem. Soc., 2006;128: 12211-20.
Seeman, "An Overview of Structural DNA Nanotechnology," Mol Biotechnol 37(3): 246-257 (2007).
Seferos et al., Locked nucleic acid-nanoparticle conjugates, Chem. Bio. Chem., 8:1230 (2007).
Seferos et al., Polyvalent DNA nanoparticle conjugates stabilize nucleic acids. Nano Lett. Jan. 2009;9(1):308-11.
Sen et al., Formation of parallel four-stranded complexes by guanine-rich motifs in DNA and its implications; for meiosis. Nature, 1988, 334:364-366.
Shahzad et al., Targeted delivery of small interfering RNA using reconstituted high-density lipoprotein nanoparticles. Neoplasia. Apr. 2011;13(4):309-19.
Sharma et al., Targeting mitogen-activated protein kinase/extracellular signal-regulated kinase kinase in the mutant (V600E) B-Raf signaling cascade effectively inhibits melanoma lung metastases. Cancer Res., 2006;66: 8200-9.
Sharp et al., RNA interference—2001. Genes Dev., 2001; 15: 485-90.
Shukla et al., Development of streptavidin-based ; nanocomplex for siRNA delivery. Mol Pharm. Dec. 2, 2013;10(12):4534-45. Doi:; 10.1021/mp400355q. Epub Oct. 25, 2013.
Shukoor et al., CpG-DNA loaded multifunctional MnO nanoshuttles for TLR9-specific cellular cargo delivery, selective immune-activation and Mri. J. Mater. Chem., 2012,22, 8826-8834.
Simmel et al., DNA nanodevices. Small, 2005;1: 284-99.
Sita et al., Dual bioluminescence and near-infrared fluorescence monitoring to evaluate spherical nucleic acid nanoconjugate activity in vivo. Proc Natl Acad Sci U S A. Apr. 18, 2017;114(16):4129-4134. Doi: 10.1073/pnas.1702736114. Epub Apr. 3, 2017.
Sohlenkamp et al., FEMS Microbiol Rev. Jan. 2016;40(1):133-59. Doi: 10.1093/femsre/fuv008. Epub Apr. 9, 2015.
Sokolova et al., The use of calcium phosphate nanoparticles encapsulating Toll-like receptor ligands and the antigen hemagglutinin to induce dendritic cell maturation and T cell activation. Biomaterials. Jul. 2010;31(21):5627-33. Doi: 10.1016/j.biomaterials.2010.03.067. Epub Apr. 24, 2010.
Song et al., Backbone-modified oligonucleotides for tuning the cellular uptake 35ehavior of spherical nucleic acids. Biomater Sci. Feb. 28, 2017;5(3):412-416. Doi: 10.1039/c6bm00792a.
Stahl et al., Deregulated Akt3 activity promotes development of malignant melanoma. Cancer Res., 2004;64: 7002-10.
Stengel et al., Determinants for Membrane Fusion Induced by Cholesterol-Modified DNA Zippers, J. Phys. Chem. B., 112:8264-74 (2008).
Stengel et al., DNA-Induced Programmable Fusion of Phospholipid Vesicles, J. Am. Chem. Soc., 129:9584-5 (2007).
Stephenson et al., Inhibition of Rous sarcoma viral RNA translation by a specific oligodeoxyribonucleotide. Proc. Natl. Acad. Sci. USA, 1978;75(1): 285-8.
Stoermer et al., Distance-dependent emission from dye-labeled oligonucleotides on striped Au/Ag nanowires: effect of secondary structure and hybridization efficiency. J. Am. Chem. Soc., 2006;128: 13243-54.
Storhoff et al., One-pot colorimetric differentiation of polynucleotides with single base imperfections using gold nanoparticle probes. J. Am. Chem. Soc., 1998;120:1959-64.
Storhoff et al., Sequence-Dependent Stability of DNA-Modified Gold Nanoparticles. Langmuir. 2002;18: 6666-6670.
Storhoff et al., What controls the optical properties of DNA-linked gold nanoparticle assemblies? J. Am. Chem. Soc., 2000;122: 4640-50.
Storz et al., An abundance of RNA regulators. Annu. Rev. Biochem., 2005;74:199-217.
Strable et al., "Natural Nanochemical Building Blocks: Icosahedral Virus Particles Organized by Attached Oligonucleotides," Nano Lett 4(8): 1385-1389 (2004).
Sugihara et al., One-pot synthesis of biomimetic shell cross-linked micelles and nanocages by ATRP in alcohol/water mixtures. Angew. Chem. Int. Ed. Engl., 2010;48(20):3500-3.
Sundaram et al., Particle-mediated delivery of recombinant expression vectors to rabbit skin induces high-titered polyclonal antisera (and circumvents purification of a protein immunogen). Nucl. Acids Res., 1996;24(7): 1375-7.
Switaj et al., CpG immunostimulatory oligodeoxynucleotide 1826 enhances antitumor effect of interleukin 12 gene-modified tumor vaccine in a melanoma model in mice. Clin Cancer Res. Jun. 15, 2004;10(12 Pt l):4165-75.
Taton et al., Scanometric DNA array detection with nanoparticle probes. Science, 2000;289(5485):1757-60.
Thomas, "The Interaction of HgC12 with Sodium Thymonucleate," J. Am. Chem. Soc., 76:6032-6034 (1954).
Thompson et al., Smart lipids for programmable nanomaterials. Nano Lett. Jul. 14, 2010;10(7):2690-3. doi: 10.1021/n1101640k.
Thurn et al., Labeling TiO2 nanoparticles with dyes for optical fluorescence microscopy and determination of TiO2-DNA nanoconjuqate stability. Small, 2009;5(11):1318-25.
Timmons et al., Investigation of fatty acid monolayers on metals by contact potential measurements. J. Phys. Chem., 1965;69:984-90.
Tincer et al., Immunostimulatory activity of polysaccharide-poly(I:C) nanoparticles. Biomaterials. Jun. 2011;32(18):4275-82. doi: 10.1016/j.biomaterials.2011.01.028.Epub Apr. 2, 2011.
Tiwari et al., Functionalized gold nanoparticles and their biomedical applications. Nanomaterials. 2011;1:31-63. doi: 10.3390/nano1010031.
Tkachenko et al., Multifunctional gold nanoparticle-peptide complexes for nuclear targeting. J. Am. Chem. Soc., 2003;125: 4700-1.
Tondelli, et al., Highly efficient cellular uptake of c-myb antisense oligonucleotides through specifically designed polymeric nanospheres. Nucl. Acids Res. 1998;26:5425-5431.
Tuerk et al., Systematic Evolution of Ligands by Exponential Enrichment: RNA Ligands to Bacteriophage T4 DNA Polymerase. Science. 1990;249:505-510.
Turberfield et al., DNA fuel for free-running nanomachines. Phys. Rev. Lett., 2003;90: 118102.
Turner et al., Nanoscale Cage-like Structures Derived from Polyisoprene-Containing Shell Cross- linked Nanoparticle Templates. Nano Lett., 2004;4(4):683-8.
Vorobjev et al., Nuclease resistance and RNase H sensitivity of oligonucleotides bridged by oligomethylenediol and oligoethylene glycol linkers. Antisense Nucleic Acid Drug Dev. Apr. 2001;11(2):77-85.
Wagner et al., Gene inhibition using antisense oligodeoxynucleotides. Nature, 1994;372: 333-5.
Wang, Synthetic CPG ODNs activate immune cells through the Toll-like receptor (TLR) pathway. Integrated DNA Technologies. Apr. 11, 2017. 3 pages.
Wang et al., "Hierarchical Assembly of Plasmonic Nanosctuctures Using Virus Capsid Scaffolds on DNA Oriqami Templates," ACS Nano 8(8):7896-7904 (2014).
Wang et al., Speeding up a single-molecule DNA device with a simple catalyst. Phys. Rev. E Stat. Nonlin. Soft Matter. Phys., 2005;72: 051918.

(56) References Cited

OTHER PUBLICATIONS

Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie.201105187. Epub Dec. 21, 2011.
West et al., Recognition and signaling by toll-like receptors. Annu Rev Cell Dev Biol. 2006;22:409-37.
Whitehead et al., Knocking down barriers: advances in siRNA delivery, Nat. Rev. Drug. Discov., 8:129 (2009).
Willis et al., Liposome-Anchored Vascular Endothelial Growth Factor Aptamers, Biocon. Chem., 9:573-82 (1998).
Wilson et al., pH-Responsive nanoparticle vaccines for dual-delivery of antigens and immunostimulatory oligonucleotides. ACS Nano. May 28, 2013;7(5):3912-25. doi: 10.1021/nn305466z. Epub Apr. 30, 2013.
Wilton et al. Antisense oligonucleotide-induced exon skipping across the human dystrophin gene transcript. Mol Ther. Jul. 2007;15(7):1288-96. Epub Feb. 6, 2007.
Winfree et al., "Design and self-assembly of two-dimensional DNA crystals," Nature 394(6693): 539-544 (1998).
Wolf et al., Rapid hybridization kinetics of DNA attached to submicron latex particles. Nucl. Acids Res., 1987;15: 2911-26.
Wolfe et al., Modulation of Tetraplex Formation by Chemical Modifications of a G4-Containing Phosphorothioate Oligonucleotide. J. Am. Chem. Soc. 1996, 118, 6301-6302 (Year: 1996).
Wolfrum et al., Mechanisms and optimization of in vivo delivery of lipophilic siRNAs. Nat Biotechnol. Oct. 2007;25(10):1149-57. Epub Sep. 16, 2007.
Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
Wu et al., Intracellular fate of spherical nucleic acid nanoparticle conjugates. J Am Chem Soc. May 28, 2014;136(21):7726-33. doi: 10.1021/ja503010a. Epub May 19, 2014.
Xiao et al., Mannosylated bioreducible nanoparticle-mediated macrophage-specific TNF-? RNA interference for IBD therapy. Biomaterials. Oct. 2013;34(30):7471-82. doi: 10.1016/j.biomaterials.2013.06.008. Epub Jun. 29, 2013.
Xiong et al., "Phase Behavior of Nanoparticles Assembled by DNA Linkers," Phys Rev Lett 102(1): 015504 (2009).
Xu et al., A gold-nanoparticle-based real-time colorimetric screening method for endonuclease activity and inhibition. Angew. Chem. Int. Ed. Engl., 2007;46(19):3468-70.
Xu et al., Homogeneous detection of nucleic acids based upon the light scattering properties of silver-coated nanoparticle probes. Anal. Chem., 2007;79(17):6650-4.
Xu et al., Thermodynamics of DNA hybridization on gold nanoparticles. J. Am. Chem. Soc., 2005;127(38): 13227-31.
Yan et al., "Aptamers and aptamer targeted delivery," RNA Biol. 6(3) 316-320 (2009).
Yan et al., "DNA-Templated Self-Assembly of Protein Arrays and Highly Conductive Nanowires," Science 301 (5641): 1882-1884 (2003).
Yang et al., Evidence that processed small dsRNAs may mediate sequence-specific mRNA degradation during RNAi in Drosophila embryos. Curr. Biol., 2000;10: 1191-200.
Yin et al., Supramolecular self-assembled nanoparticles mediate oral delivery of therapeutic TNF-? siRNA against systemic inflammation. Angew Chem Int Ed Engl. May 27, 2013;52(22):5757-61. doi: 10.1002/anie.201200991. Epub Apr. 22, 2013.
Yin Win et al., Effects of particle size and surface coating on cellular uptake of polymeric nonparticles for oral delivery of anticancer drugs. Biomaterials, 2005;26: 2713-22.
You et al., Engineering the nanoparticle-biomacromolecule interface. Soft Matter, 2006;2: 190-204.
Young et al., Hollow spherical nucleic acids for intracellular gene regulation based upon biocompatible silica shells, Nano Lett., 12:3867 (2012).

Yu et al., Exoplasmic cysteine Cys384 of the HDL receptor SR-BI is critical for its sensitivity to a small-molecule inhibitor and normal lipid transport activity. Proc Natl Acad Sci U S A. Jul. 26, 2011;108(30):12243-8. Epub Jul. 11, 2011.
Zabner et al., Cellular and molecular barriers to gene transfer by a cationic lipid. J. Biol. Chem., 1995;270: 18997-9007.
Zamai et al., Camptothecin Poly[N-(2-Hydroxypropyl) Methacrylamide] Copolymers in Antitopoisomerase-1 Tumor Therapy: Intratumor Release and Antitumor Efficacy. Mol Cancer Ther 2003;2: 29-40.
Zamecnik et al., Inhibition of Rous sarcoma virus replication and cell transformation by a specific oligodeoxynucleotide. Proc. Natl. Acad. Sci. USA, 1978;75(1): 280-4.
Zamore et al., RNAi: Double-Stranded RNA Directs the ATP-Dependent Cleavage of mRNA at 21 to 23 Nucleotide Intervals. Cell. 2000;101:25-33.
Zhang et al., "A general strategy for the DNA-mediated self-assembly of functional nanoparticles into heterogeneous systems," Nat Nanotechnol 8(11): 865-872 (2013).
Zhang et al., "DNA-Directed Three-Dimensional Protein Organization," Angew Chem Int Ed 51(14): 3382-3385 (2012).
Zhang et al., A general approach to DNA-programmable atom equivalents. Nat Mater. Aug. 2013;12(8):741-6. doi: 10.1038/nmat3647. Epub May 19, 2013.
Zhang et al., An extremely stable and orthogonal DNA base pair with a simplified three-carbon backbone. J. Am. Chem. Soc., 2005;127:74-75.
Zhang et al., Antibody-linked spherical nucleic acids for cellular targeting, J. Am. Chem. Soc., 134:16488-91 (2012).
Zhang et al., Cationic shell-crosslinked knedel-like nanoparticles for highly efficient gene and oligonucleotide transfection of mammalian cells. Biomaterials, 2009;30(5):968-77.
Zhang et al., Control of DNA strand displacement kinetics using toehold exchange. J. Am. Chem. Soc., 2009;131: 17303-14.
Zhang et al., Informational liposomes: Complexes derived from cholesteryl-conjugated oligonucleotides and liposomes. Tetrahedron Letters. 1996. 37(35):6243-6.
Zhang et al., Nanopod formation through gold nanoparticle templated and catalyzed crosslinking of polymers bearing pendant propargyl ethers. J Am Chem Soc. Nov. 3, 2010;132(43):15151-3.
Zhang et al., Structure-activity relationships of cationic shell-crosslinked knedel-like nanoparticles: shell composition and transfection efficiency/cytotoxicity, Biomaterials, 31:1805 (2010).
Zhang et al., TLR9-mediated siRNA delivery for targeting of normal and malignant human hematopoietic cells in vivo. Blood. Feb. 21, 2013;121(8):1304-15. doi: 10.1182/blood-2012-07-442590. Epub Jan. 3, 2013.
Zhao et al., A rapid bioassay for single bacterial cell quantitation using bioconjugated nanoparticles. Proc. Natl. Acad. Sci. USA, 2004;101(42):15027-32.
Zheng et al., "From Molecular to Macroscopic via the Rational Design of a Self-Assembled 3D DNA Crystal," Nature 461 (7260): 74-77 (2009).
Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.lll8425109. Epub Jul. 6, 2012.
Zimmer, Antisense oligonucleotide delivery with polyhexylcyanoacrylate nanoparticles as carriers. Methods, 1999; 18: 286-95.
Aissaoui et al., Efficient topical delivery of plasmid DNA to lung in vivo mediated by putative triggered, PEGylated pDNA nanoparticles, J .Control Release. 154:275-84 (2011).
Alkilany et al., Toxicity and cellular uptake of gold nanoparticles: what we have learned so far?, N. Nanopart Res. 12:2313-33 (2010).
Altschul et al., Basic local alignment search tool, J. Mol. Biol. 215:403-10 (1990).
Arnida et al., Cellular uptake and toxicity of gold nanoparticles in prostate cancer cells: a comparative study of rods and spheres., J. Appl. Toxicol. 30:212-7 (2010).

(56) References Cited

OTHER PUBLICATIONS

Bae et al., Oil-encapsulating PEO-PPO-PEO/PEG shell cross-linked nanocapsules fortarget-specific delivery of paclitaxel, *Biomacromolecules*. 8:650-6 (2007).
Banchelli et al., Phospholipid membranes decorated by cholesterol-based oligonucleotides as soft hybrid nanostructures, *J. Phys. Chern B*. 112:10942-52 (2008).
Banerjee et al., Poly(ethylene glycol)-Prodrug Conjugates: Concept, Design, and Applications, *J. Drug Deliv*. 2012:103973 (2012).
Banga et al., Cross-linked miceller spherical nucleic acids from thermoresponsive templates, *J. Am. Chem. Soc*. 139:4278-81 (2017).
Banga et al., Liposomal spherical nucleic acids, *J. Am. Chem. Soc*.136:9866-9 (2014).
Batrakova et al., Pluronic block copolymers: evolution of drug delivery concept from inert nanocarriers to biological response modifiers, *J. Control. Release*. 130:98-106 (2008).
Brodin et al., DNA-mediated engineering of multicomponent enzyme crystals, *Proc. Natl. Acad. Sci. USA*. 112:4564-9 (2015).
Carson et al., Hydroxymethyluracil modifications enhance the flexibility and hydrophilicity of double-stranded DNA, *Nucleic Acids Res*. 44:2085-92 (2016).
Calabrese et al., Biocompatible infinite-coordination-polymer nanoparticle-nucleic-acid conjugates for antisense gene regulation, *Agnew Chem. Int. Ed. Engl.* 54:476-80 (2015).
Choi et al., Mechanism for the endocytosis of spherical nucleic acid nanoparticle conjugates, *Proc. Natl. Acad. Sci. USA*. 110:7625-30 (2013).
Chung et al., Nuclease-resistant DNA aptamer on gold nanoparticles for the simultaneous detection of Pb2+ and Hg2+ in human serum, *Biosens. Bioelectron*. 41:827-32 (2013).
Cutler et al., Polyvalent oligonucleotide iron oxide nanoparticle "click" conjugates, *Nano. Lett*.10:1477-80 (2010).
Cutler et al., Spherical nucleic acids, *J. Am. Chem. Soc*. 134:1376-91 (2012).
De Mesmaeker et al., Backbone modifications in oligonucleotides and peptide nucleic acid systems, *Curr. Opin. Struct. Biol*. 5:343-55 (1995).
Diniz et al., Pluronic F-127 hydrogel as a promising scaffold for encapsulation of dental-derived mesenchymal stem cells, *J. Mater. Sci. Mater. Med*. 26:153 (2015).
Englisch et al., Chemically Modified Oligonucleotides as Probes and Inhibitors, *Angew. Chem. Int. Ed. Engl*. 30: 613-629 (1991).
Freier et al., The ups and downs of nucleic acid duplex stability: structure-stability studies on chemically-modified DNA:RNA duplexes, *Nucleic Acids Res*. 25:4429-43 (1997).
Greish, Enhanced permeability and retention (EPR) effect for anti-cancer nanomedicine drug targeting, *Methods Mol. Biol*. 624:25-37 (2010).
Hong et al., Directed Assembly of Nucleic Acid-Based Polymeric Nanoparticles from Molecular Tetravalent Cores, *J. Am. Chem. Soc*. 137:8184-91 (2015).
International Preliminary Report on Patentability, PCT/US2017/048726 (dated Mar. 26, 2019).
International Search Report and Written Opinion, PCTUS17/48726 (dated Feb. 2, 2018).
Kroschwitz, The Concise Encyclopedia of Polymer Science and Engineering, pp. 858-859, John Wiley & Sons, (1990).
Lee et al., Silver nanoparticle-oligonucleotide conjugates based on DNA with triple cyclic disulfide moieties., *Nano. Lett*. 7:2112-5 (2007).
Lin, et al., Temperature-dependent adsorption of pluronic F127 block copolymers onto carbon black particles distersed in aqueous media, *J Phys Chem B*. 106:10834-10844 (2002).
Linse et al., Temperature-dependent micellization in aqueous block copolymer solutions, *Macromolecules*. 25:5434-5439 (1992).
Liu et al., Bioconjugated pluronic triblock-copolymer micelle-encapsulated quantum dots for targeted imaging of cancer: in vitro and in vivo studies, *Theranostics*. 2:705-13 (2012).
Macfarlane et al., Nanoparticle superlattice engineering with DNA, *Science*. 334:204-8 (2011).

Martin, Ein neuer A New Access to 2'-O-Alkylated ribonucleosides and properties of of 2'O-Alkylated Oligoribonucleotides, *Helv. Chim. Acta*. 78:486-504 (1995).
Massich et al., Cellular response of polyvalent oligonucleotide-gold nanoparticle conjugates, *ACS Nano*. 4:5641-6 (2010).
Mirkin et al., A DNA-based method for rationally assembling nanoparticles into macroscopic materials, *Nature*. 382:607-9 (1996).
Nielsen et al., Sequence-selective recognition of DNA by strand displacement with a thymine-substituted polyamide, *Science*. 254:1497-1500 (1991).
Radovic-Moreno et al., Immunomodulatory spherical nucleic acids, *Proc. Natl. Acad. Sci. USA*. 112:3892-7 (2015).
Rosi et al., Oligonucleotide-modified gold nanoparticles for intracellular gene regulation, *Science*. 312:1027-30 (2006).
Sanghvi, Antisense Research and Applications, Chapter 15, CRC Press (1993).
Seferos et al., Nano-flares: probes for transfection and mRNA detection in living cells, *J. Am. Chem. Soc*. 129:15477-9 (2007).
Sun et al., Multidimensional sensor for pattern recognition of proteins based on DNA-gold nanoparticles conjugates, *Anal. Chem*. 87:3354-9.
Trong et al., Mechanisms of micellization and rheology of PEO-PPO-PEO triblock copolymers with various architectures, *J. Colloid Interface Sci*. 328:278-87 (2008).
Watson et al., DNA-block copolymer conjugates, *J. Am. Chem. Soc*. 123:5592-3 (2001).
Zhang et al., Non-invasive multimodal functional imaging of the intestine with frozen micellar naphthalocyanines, *Nat. Nanotechnol*. 9:631-8 (2014).
Zhang et al., PowerBLAST: a new network BLAST application for interactive or automated sequence analysis and annotation, *Genome Res*. 7:649-56 (1997).
D'ydewalle et al., The Antisense Transcript SMN-AS1 Regulates SMN Expression and Is a Novel Therapeutic Target for Spinal Muscular Atrophy. Neuron. 2017;93(1):66-79.
Li et al., Targeted delivery of antisense oligodeoxynucleotide and small interference RNA into lung cancer cells. Mol Pharm. Sep. 2006-Oct.;3(5):579-88. doi: 10.1021/mp060039w. Publication Date:Jul. 12, 2006.
Manoharan et al., Lipidic nucleic acids. Tetrahedron Letters. May 22, 1995;36(21):3651-4.
Osman et al., Morpholino antisense oligonucleotides targeting intronic repressor Element1 improve phenotype in SMA mouse models. Human Molecular Genetics. 2014;23(18):4832-45.
Pao et al., Dual Masking of Specific Negative Splicing Regulatory Elements Resulted in Maximal Exon 7 Inclusion of SMN2 Gene. Molecular Therapy. 2014;22(4):854-61.
Rubenstein et al., Antisense oligonucleotide intralesional therapy for human PC-3 prostate tumors carried in athymic nude mice. J Surg Oncol. Jul. 1996;62(3):194-200. doi: 10.1002/(SICI)1096-9098(199607)62:3<194::AID-JS09>3.0.CO;2-2.
U.S. Appl. No. 16/772,551. filed Jun. 12, 2020, Mirkin et al.
Banga et al., Drug-Loaded Polymeric Spherical Nucleic Acids: Enhancing Colloidal Stability and Cellular Uptake of Polymeric Nanoparticles through DNA Surface-Functionalization. Biomacromolecules. Feb. 13, 2017;18(2):483-489. doi: 10.1021/acs.biomac.6b01563. Epub Jan. 18, 2017.
[No Author Listed] Modern Pharmaceutical Design. 2006. Chapter 5. p. 273. English language summary. 2 pages.
Dokka et al., Dermal delivery of topically applied oligonucleotides via follicular transport in mouse skin. J Invest Dermatol. 2005;124(5):971-975. doi: 10.1111/j.0022-202X.2005.23672.x.
Leachman et al., Therapeutic siRNAs for dominant genetic skin disorders including pachyonychia congenita. J Dermatol Sci. 2008;51(3): 151-157. doi: 10.1016/j .jdermsci.2008.04.003.
Lewandowski et al., Topically Delivered Tumor Necrosis Factor-?-Targeted Gene Regulation for Psoriasis. J Invest Dermatol. 2017;137(9):2027-2030. doi:10.1016/j.jid.2017.04.027.
Tran et al., Targeting V600EB-Raf and Akt3 using nanoliposomal-small interfering RNA inhibits cutaneous melanocytic lesion development. Cancer Res. Sep. 15, 2008;68(18):7638-49. doi: 10.1158/0008-5472. CAN-07-6614.

(56) References Cited

OTHER PUBLICATIONS

Wang et al., Co-delivery of drugs and DNA from cationic core-shell nanoparticles selfassembled from a biodegradable copolymer. Nat Mater. Oct. 2006;5(10):791-6. doi: 10.1038/nmat1737. Epub Sep. 24, 2006. PMID: 16998471.
U.S. Appl. No. 15/502,955, filed Feb. 9, 2017, Mirkin et al.
U.S. Appl. No. 15/527,840, filed May 18, 2017, Mirkin et al.
U.S. Appl. No. 16/611,502, filed Nov. 7, 2019, Mirkin et al.
U.S. Appl. No. 16/611,548, filed Nov. 7, 2019, Mirkin et al.
U.S. Appl. No. 16/160,196, filed Oct. 15, 2018, Mirkin et al.
U.S. Appl. No. 17/011,658, filed Sep. 3, 2020, Mirkin et al.

* cited by examiner

CROSSLINKED MICELLAR SPHERICAL NUCLEIC ACIDS

CROSS-REFERENCE TO RELATED APPLICATIONS

This Application is a national stage filing under 35 U.S.C. § 371 of International Patent Application Serial No. PCT/US2017/048726, filed Aug. 25, 2017, entitled "MICELLAR SPHERICAL NUCLEIC ACIDS FROM THERMO-RESPONSIVE, TRACELESS TEMPLATES," which claims the benefit of the filing date of U.S. Provisional Application Serial No. 62/379,352, filed Aug. 25, 2016, entitled "MICELLAR SPHERICAL NUCLEIC ACIDS FROM THERMORESPONSIVE, TRACELESS TEMPLATES", the entire contents of which are herein incorporated by reference in their entireties.

STATEMENT OF GOVERNMENT SUPPORT

This invention was made with government support under U54 CA199091 and U54 CA151880 awarded by the National Institutes of Health. The government has certain rights in the invention.

FIELD OF THE DISCLOSURE

The disclosure relates generally to spherical nucleic acids. More particularly, the disclosure related to crosslinked micellar spherical nucleic acids that can be prepared under moderate conditions.

BACKGROUND

Spherical nucleic acids (SNAs) have become an important platform for programmable assembly,[1] bio-detection[2], and nucleic acid-based therapeutics.[3] Historically, SNAs have been synthesized by covalently immobilizing a dense layer of highly oriented nucleic acids onto a spherical gold nanoparticle core.[4] The resulting three-dimensional polyvalent architecture of the SNA makes it a higher affinity binder than the same linear sequence from which it is comprised.[5] The dense oligonucleotide shell also increases the resistance of SNAs to enzymatic degradation,[6] increasing intact oligonucleotide lifetimes. In addition, by engaging cell-surface receptors, SNAs can actively traverse cell membranes without the need for transfection agents.[7] As a result, SNAs have emerged as "single-entity" intracellular diagnostic tools,[2a] gene-regulating structures,[3] and immunomodulatory agents[8] that exhibit minimal cytotoxicity and non-specific immunogenic responses.[9]

Since the aforementioned physical and biological properties of SNAs are independent of the nature of the core,[5] a broad range of materials (Au,[4] Ag,[10] $\gamma$-Fe$_2$O$_3$,[11] CdSe, Pt, Pd) have been used as templates for their syntheses. However, concerns about the potential long-term toxicity and metabolic fate of metallic nanoparticle cores[12,13] have inspired a shift to the use of organic templates such as lipisomes,[14] proteins,[15] and block copolymer nanostructures[16] as template materials.

An ideal SNA is one that can be rapidly made under moderate conditions from biocompatible reagents in monodisperse and size tunable form. Thus, a need exists for such methods to prepare SNAs.

SUMMARY

One aspect of the disclosure provides a method of making a crosslinked micellar spherical nucleic acid (SNA) comprising (a) admixing a polyethyleneoxide-polypropyleneoxide-polyethyleneoxide (PEO-PPO-PEO) block copolymer and a plurality of amphiphilic oligonucleotides in a buffer to form an SNA, wherein the amphiphilic oligonucleotide comprises (i) a lipid moiety and (ii) at least one reactive group, (b) admixing the resulting SNA with a PEGylated crosslinking agent to form the crosslinked micellar SNA, wherein the PEGylated crosslinking agent comprises at least two reactive sites, each reactive site reacting with the reactive group of the amphiphilic oligonucleotide to form a covalent bond and thereby crosslink the amphiphilic oligonucleotides, and (c) optionally washing the crosslinked micellar SNA to remove uncrosslinked amphiphilic oligonucleotides.

Another aspect of the disclosure provides a crosslinked micellar spherical nucleic acid prepared according to the method of the disclosure.

Another aspect of the disclosure provides a method of inhibiting expression of a gene comprising the step of hybridizing a polynucleotide encoding said gene product with one or more oligonucleotides complementary to all or a portion of said polynucleotide, said oligonucleotide being attached to the crosslinked micellar SNA of the disclosure, wherein hybridizing between said polynucleotide and said oligonucleotide occurs over a length of said polynucleotide with a degree of complementarity sufficient to inhibit expression of said gene product.

Another aspect of the disclosure provides a method for up-regulating activity of a toll-like receptor (TLR), comprising contacting a cell having the toll-like receptor with a crosslinked micellar SNA of the disclosure.

Another aspect of the disclosure provides a method for down-regulating toll-like receptor (TLR), comprising contacting a cell having the toll-like receptor with a crosslinked micellar SNA of the disclosure.

Further aspects and advantages will be apparent to those of ordinary skill in the art from a review of the following detailed descriptions. While the compositions and methods are susceptible of embodiments in various forms, the description hereafter includes specific embodiments with the understanding that the disclosure is illustrative and is not intended to limit the invention to the specific embodiments described herein.

BRIEF DESCRIPTION OF THE FIGURES

For a more complete understanding of the disclosure, reference should be made to the following detailed description and accompanying drawings wherein.

DETAILED DESCRIPTION

Figure 1:
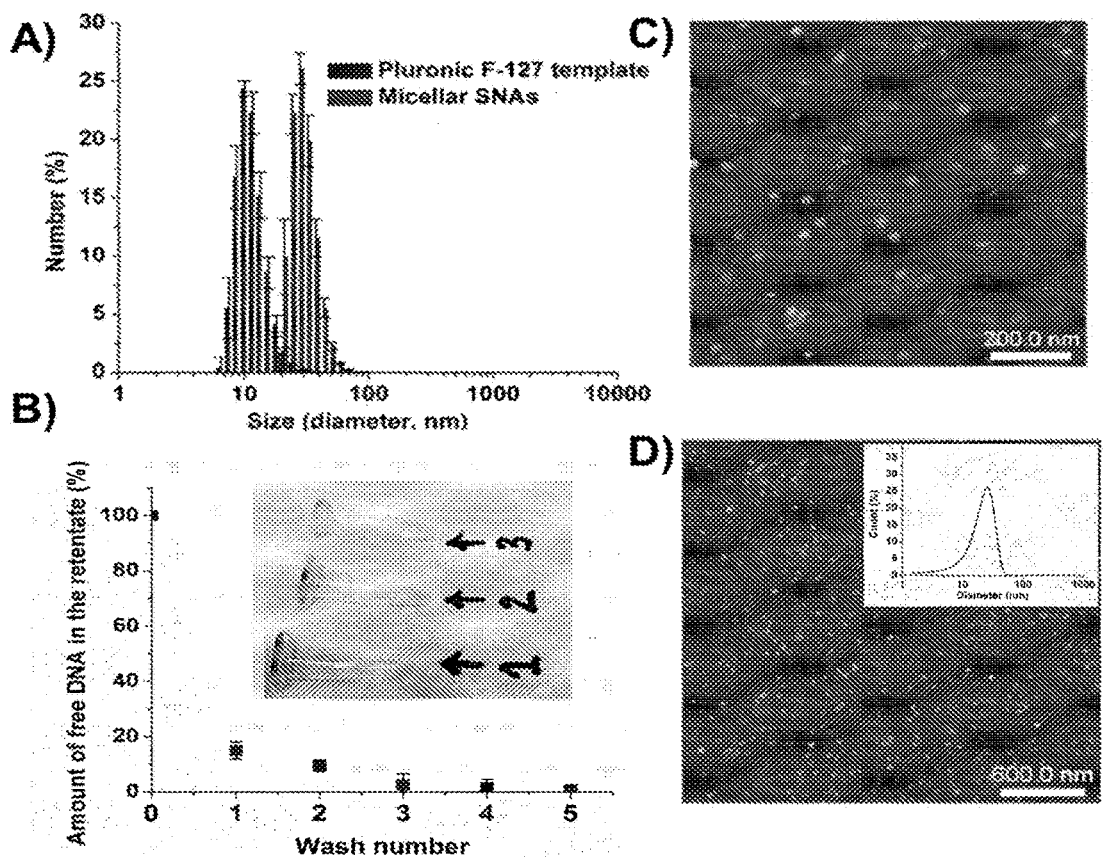
FIG. 1. (A) shows DLS histograms of the Pluronic F-127 templates before DNA insertion and the crosslinked micellar SNAs. (B) shows a plot of the amount of free, unincorporated DNA in the solution. The inset is a photographic image of the filtrates, showing the blue color of Cy-5 labeled DNA visually disappears in the 3$^{rd}$ wash. (C) is an AFM image of the crosslinked micellar SNAs after drop-cast and dried on mica. (D) is an AFM image of the crosslinked micellar SNAs after drop-casting and dried on mica. The inset shows a distribution centering at 30±8 nm, slightly smaller than the DLS data as expected for dried materials.

Provided herein are methods of making crosslinked micellar spherical nucleic acids (SNAs) under moderate conditions from biocompatible materials. The spherical nucleic acids of the disclosure comprise polyethyleneoxide-polypropyleneoxide-polyethyleneoxide, a plurality of oligonucleotides, wherein each oligonucleotide comprises a lipid moiety and a nucleobase portion, and the oligonucleotides are crosslinked with a PEGylated crosslinking agent. The methods disclosed herein allow for the facile assembly of nucleic acids with hydrophobic tails and stretches of functionalized T-bases biocompatible SNA constructs.

PEO-PPO-PEO Micelles

Polyoxyethylene-polyoxypropylene-polyoxyethylene (PEO-PPO-PEO) is an amphiphilic block copolymer that can be assembled into spherical micelles at room temperature at low critical micelle concentrations (CMC). In addition, PEO-PPO-PEO has a thermo-responsive CMC, and therefore micelles made from PEO-PPO-PEO can be easily assembled and disassembled based upon a change in temperature. The thermo-responsive CMC can be used for purifying the targeted SNA architectures.[18a, 19]

Above their CMC, PEO-PPO-PEO block copolymers can assemble into small, monodispersed micelles that consist of a hydrophobic PPO as the core surrounded by a hydrophilic PEO shell.[20] The micelles can have a diameter of about 2 nm to about 100 nm in mean diameter, about 2 nm to about 90 nm in mean diameter, about 2 nm to about 80 nm in mean diameter, about 2 nm to about 70 nm in mean diameter, about 2 nm to about 60 nm in mean diameter, about 2 nm to about 50 nm in mean diameter, about 2 nm to about 40 nm in mean diameter, about 2 nm to about 30 nm in mean diameter, or about 2 nm to about 20 nm in mean diameter, about 2 nm to about 10 nm in mean diameter, about 5 nm to about 80 nm in mean diameter, about 5 nm to about 70 nm in mean diameter, about 5 nm to about 60 nm in mean diameter, about 5 nm to about 50 nm in mean diameter, about 5 nm to about 40 nm in mean diameter, about 5 nm to about 30 nm in mean diameter, about 6 nm to about 25 nm in mean diameter, about 7 nm to about 20 nm in mean diameter, about 8 nm to about 15 nm in mean diameter, about 8 nm to about 12 nm in mean diameter, about 10 nm to about 14 nm in mean diameter. At these size ranges, PEO-PPO-PEO-derived micelles advantageously demonstrate long in vivo circulation time and can deliver encapsulated chemotherapeutics into a tumor tissue via the enhanced permeation and retention (EPR) effect.[21]

The PEO-PPO-PEO block copolymers can have a molecular weight in a range of about 500 Da to about 20000 Da, about 500 Da to about 14000, about 800 Da to about 13800 Da, about 1000 Da to about 12000 Da, about 1500 Da to about 11800 Da, about 2000 Da to about 11000 Da, about 2200 Da to about 10000 Da, about 2500 Da to about 9000 Da, about 3000 Da to about 8000 Da, about 3300 Da to about 7000 Da, about 3500 Da to about 6500 Da, about 3500 Da, about 6000 Da, about 1200 Da, and/or up to about 20000 Da. The block copolymer can be represented by the formula $(PEO)_x(PEO)_y(PEO)_z$ wherein x can be in a range of 2 to 130, y can be in a range of 6 to 67, and z can be in a range of 2 to 130. In some embodiments, x and z have different values. In some embodiments, x and z have the same value. PEO-PPO-PEO block copolymers, also known as poloxamers, are available commercially, for example, under the Pluronic® tradename from BASF Chemicals, under the Synperonics® tradename from Croda International Chemicals Company, and under the Kolliphor® tradename from BASF Chemicals. Suitable block copolymers are pharmaceutical-grade. An exemplary pharmaceutical grade PEO-PPO-PEO block copolymer is Pluronic® F127, a solid block copolymer having a molecular weight of about 12500 Da and a 70% polyoxyethylene content and can be represented by the formula $(PEO)_{98}(PPO)_{67}(PEO)_{98}$.

Methods of forming PEO-PPO-PEO micelles are known in the art. PEO-PPO-PEO micelles readily assemble when the block copolymer is provided in solution in a concentration in an amount greater than its critical micelle concentration at a given solution temperature.

Spherical Nucleic Acids

The SNA can have a diameter of about 2 nm to about 250 nm in mean diameter, about 2 nm to about 240 nm in mean diameter, about 2 nm to about 230 nm in mean diameter, about 2 nm to about 220 nm in mean diameter, about 2 nm to about 210 nm in mean diameter, about 2 nm to about 200 nm in mean diameter, about 2 nm to about 190 nm in mean diameter, about 2 nm to about 180 nm in mean diameter, about 2 nm to about 170 nm in mean diameter, about 2 nm to about 160 nm in mean diameter, about 2 nm to about 150 nm in mean diameter, about 2 nm to about 140 nm in mean diameter, about 2 nm to about 130 nm in mean diameter, about 2 nm to about 120 nm in mean diameter, about 2 nm to about 110 nm in mean diameter, about 2 nm to about 100 nm in mean diameter, about 2 nm to about 90 nm in mean diameter, about 2 nm to about 80 nm in mean diameter, about 2 nm to about 70 nm in mean diameter, about 2 nm to about 60 nm in mean diameter, about 2 nm to about 50 nm in mean diameter, about 2 nm to about 40 nm in mean diameter, about 2 nm to about 30 nm in mean diameter, or about 2 nm to about 20 nm in mean diameter, about 2 nm to about 10 nm in mean diameter. The size of the SNA is from about 5 nm to about 150 nm (mean diameter), from about 5 to about 50 nm, from about 10 to about 30 nm, from about 10 to 150 nm, from about 10 to about 100 nm, from about 20 nm to about 150 nm, from about 10 to about 50 nm, from about 20 nm to about 50 nm, from about 25 to about 45 nm, or from about 30 nm to about 40 nm. The size of the SNA is from about 5 nm to about 150 nm (mean diameter), from about 30 to about 100 nm, from about 40 to about 80 nm. The size of the SNA used in a method varies as required by their particular use or application. The variation of size is advantageously used to optimize certain physical characteristics of the SNA, for example, optical properties or the amount of surface area that can be functionalized as described herein.

The SNA provided herein comprise amphiphilic oligonucleotides including (i) a lipid portion and (ii) a nucleobase portion. The SNA can include at least about 10 strands of amphiphilic oligonucleotides, at least about 50 strands of amphiphilic oligonucleotides, at least about 100 strands of amphiphilic oligonucleotides, at least about 150 strands of amphiphilic oligonucleotides, at least about 200 strands of amphiphilic oligonucleotides, at least about 250 strands of oligonucleotides, at least 300 strands of oligonucleotides, or at least 350 strands of oligonucleotides and/or up to about 400 strands of oligonucleotides, up to about 350 strands of oligonucleotides, or up to about 300 strands of oligonucleotides.

The oligonucleotide can comprise either RNA or DNA. In embodiments, the oligonucleotide comprises RNA. The RNA can be an inhibitory RNA (RNAi) that performs a regulatory function, and is chosen from the group consisting of a small RNAi that is selected from the group consisting of a small inhibitory RNA (siRNA), an RNA that forms a triplex with double stranded DNA, and a ribozyme. Alternatively, the RNA is microRNA that performs a regulatory function. In still further embodiments, the RNA is a piwi-interacting RNA (piRNA). In embodiments, the oligonucleotide comprises DNA. The DNA can be, in some embodiments, an antisense-DNA.

Oligonucleotides contemplated for use according to the disclosure are from about 5 to about 100 nucleotides in length. Methods and compositions are also contemplated wherein the oligonucleotide is about 10 to about 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed, for example about 15 to about 35 nucleotides, to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides in length are contemplated. Throughout, the term nucleotide is interchangeably referred to as a nucleobase. In embodiments, the oligonucleotide comprises a section of at least two nucleobases each having an amine functional group, at least three nucleobases each having an amine functional group, or at least four nucleobases each having an amine functional group and/or up to six nucleobases each having an amine functional group, up to five nucleobases each having an amine functional group, or up to four nucleobases each having an amine functional group.

The oligonucleotide can include a section having a therapeutic sequence. The therapeutic sequence can encode a single gene, multiple genes, chimeric proteins, DNA sequences or regulator RNA, or precursor of such regulatory RNA molecules. Encoded proteins can include signal peptides to aid in the excretion of gene products and/or other specific sequences to aid in the delivery, stability and activity of the gene product, depending on the therapeutic application. In embodiments, the therapeutic sequence comprises an immunomodulatory sequence. In embodiments, the therapeutic sequence can be complementary to a target polynucleotide.

Modified Oligonucleotides

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide."

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which can be a basic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still other embodiments, oligonucleotide mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., 1991, *Science*, 254: 1497-1500, the disclosures of which are herein incorporated by reference.

In still other embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligonucleotide consists of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, PO(BH$_3$)—, —P(O,S)—, —P(S)$_2$—, —PO(R")—, —PO(OCH$_3$)—, and —PO(NHR$^H$)—, where R$^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH=, —$CH_2$—$CH_2$—O—, —$NR^H$—$CH_2$—$CH_2$—, —$CH_2$—$CH_2$—$NR^H$, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—O—CO—O—, O—CO—$CH_2$—O—, —O—$CH_2$—CO—O—, —$CH_2$—CO—$NR^H$—, —O—CO—$NR^H$—, —$NR^H$CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N=, —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH=, —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —OS(O)$_2$—$NR^H$, —$NR^H$—S(O)$_2$—$CH_2$—; —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(O CH$_2$CH$_2$S—R)—O—, —O—PO(BH$_3$)—O—, —O—PO(NHR$^N$)—O—, —O—P(O)$_2$—NR$^H$H—, —NR$^H$—P(O)$_2$—O—, —O—P(O,NR$^H$)—O—, —$CH_2$—P(O)$_2$—O—, —O—P(O)$_2$—$CH_2$—, and —O—Si(R")$_2$—O—; among which —$CH_2$—CO—NR$^H$—, —$CH_2$—NR$^H$—O—, —S—$CH_2$—O—, —O—P(O)$_2$—O—P(—O,S)—O—, —O—P(S)$_2$—O—, —NR$^H$P(O)$_2$—O—, —O—P(O,NR$^H$)—O—, —O—PO(R")—O—, —O—PO(CH$_3$)—O—, and —O—PO(NHR$^N$)—O—, where R$^H$ is selected form hydrogen and $C_{1-4}$-alkyl, and R" is selected from $C_{1-6}$-alkyl and phenyl, are contemplated. Further illustrative examples are given in Mesmaeker et. al., 1995, *Current Opinion in Structural Biology*, 5: 343-355 and Susan M. Freier and Karl-Heinz Altmann, 1997, *Nucleic Acids Research*, vol 25: pp 4429-4443.

Still other modified forms of oligonucleotides are described in detail in U.S. Patent Application No. 20040219565, the disclosure of which is incorporated by reference herein in its entirety.

Modified oligonucleotides can also contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Other embodiments include O[($CH_2$)$_n$O]$_m$CH$_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$]$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, *Helv. Chin. Acta*, 78: 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$N(CH$_3$)$_2$, also described in examples herein below.

Still other modifications include 2'-methoxy (2'-O—CH$_3$), 2'-aminopropoxy (2'-OCH$_2$CH$_2$CH$_2$NH$_2$), 2'-allyl (2'-CH$_2$CH=CH$_2$), 2'-O-allyl(2'-O—CH$_2$CH=CH$_2$) and 2'-fluoro (2'-F). The 2'-modification can be in the arabino (up) position or ribo (down) position. In one aspect, a 2'-arabino modification is 2'-F. Similar modifications can also be made at other positions on the oligonucleotide, for example, at the 3' position of the sugar on the 3' terminal nucleotide or in 2'-5' linked oligonucleotides and the 5' position of 5' terminal nucleotide. Oligonucleotides can also have sugar mimetics such as cyclobutyl moieties in place of the pentofuranosyl sugar. See, for example, U.S. Pat. Nos. 4,981,957; 5,118,800; 5,319,080; 5,359,044; 5,393,878;

5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated herein by reference in their entireties.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene $(CH_2)_n$ group bridging the 2' oxygen atom and the 4' carbon atom wherein n is 1 or 2. LNAs and preparation thereof are described in WO 98/39352 and WO 99/14226.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5mC), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (particularly 5-bromo, 5-trifluoromethyl) and other 5-substituted uracils and cytosines; 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5, 4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases can also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia of Polymer Science and Engineering, pages 858-859, Kroschwitz, J. I., ed. John Wiley & Sons, 1990, those disclosed by Englisch et al., 1991, *Angewandte Chemie, International Edition*, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O—6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyl-adenine, 7-deazaxanthine, 7-deazaguanine, $N^4,N^4$-ethanocytosin, N',N'-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-triiazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, *Nucleic Acids Research, vol.* 25: pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, *Angewandte Chemie, International Edition*, 30: 613-722 (see especially pages 622 and 623, and in the Concise Encyclopedia of Polymer Science and Engineering, J. I. Kroschwitz Ed., John Wiley & Sons, 1990, pages 858-859; Cook, *Anti-cancer Drug Design* 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Spacers

In certain aspects, the oligonucleotide further comprises a spacer between the nucleotide portion and the lipid portion. "Spacer" as used herein means a moiety that does not participate in modulating gene expression per se but which serves to increase distance, for example, between the nucleobases and the lipid moiety. The spacer can be a polymer, including but not limited to a water-soluble polymer, a nucleic acid, a polypeptide, an oligosaccharide, a carbohydrate, a lipid, an ethylglycol, or combinations thereof.

Reactive Group

The amphiphilic oligonucleotide further comprises a reactive group. The amphiphilic oligonucleotide can be covalently bound to the crosslinking agent through the reactive group. In embodiments, the reactive group can include a nucleophile that can react with a succinimidyl group on a PEGylated crosslinking agent. The nucleophile can be any nucleophile that reacts with a succinimidyl group, for example an amine. In embodiments, the reactive group of the amphiphilic oligonucleotide comprises an amine, a hydroxyl, a succinimidyl, an alkyne, or an azide. In embodiments, the reactive group comprises an amine. In embodiments wherein the reactive group is an alkyne, the oligonucleotide can bind to a PEGylated crosslinking agent with an azide at each terminus (or vice versa) to allow crosslinking via a click chemistry type reaction.

Lipids

The lipid moiety of the amphiphilic oligonucleotide can be chosen from the phosphocholine family of lipids or the phosphoethanolamine family of lipids. Examples include 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), and 1,2-dihexadecanoyl-sn-glycero-3-phosphoethanolamine (DPPE).

The lipid moiety and the oligonucleotide can be connected via Cu-free click chemistry using click-chemistry reactive pairs. Click-chemistry reactive pairs include a first click chemistry reagent (e.g., an azide) and a second click chemistry reagent (e.g., an alkyne). It will be appreciated that either entity of the click chemistry reactive pair can be incorporated into the lipid while the other entity of the reactive pair can be incorporated into the oligonucleotide. Additional suitable reactive pairs are well known in the art and include, but are not limited to, reactive pairs that couple amines to carboxylic acids, maleimides to sulfhydryls, vinyl sulfones to sulfhydryls, and acrylates to sulfhydryls. In embodiments, the lipid moiety and the oligonucleotide are connect via a triazolyl. The triazolyl can be formed by reacting an oligonucleotide having an alkyne moiety and a lipid having an azide moiety under conditions to form the triazolyl.

The amphiphilic oligonucleotide can be prepared by reacting a lipid moiety comprising a first click chemistry reagent with an oligonucleotide comprising a second click chemistry reagent, under conditions suitable for click chemistry. Suitable conditions are well known to one of ordinary skill in the art. For example, the lipid can be dissolved or suspended in a solvent, optionally activated, and admixed with an excess of a first click chemistry reagent, at ambient conditions. The reagent can be added in an amount to provide a reagent to lipid ratio of about 1:1 to about 1000:1, for example, about 1:1 to about 750:1, about 1:1 to about 500:1, about 1:1 to about 250:1, about 1:1 to about 100:1, about 1:1 to about 50:1, or about 1:1 to about 25:1. Similarly, the oligonucleotide can be dissolved in a solvent, optionally activated, and admixed with an excess of a second click chemistry reagent, at ambient conditions. The second reagent can be added in an amount to provide a reagent to oligonucleotide ratio of about 1:1 to about 1000:1, for example, about 1:1 to about 750:1, about 1:1 to about 500:1, about 1:1 to about 250:1, about 1:1 to about 100:1, about 1:1 to about 50:1, or about 1:1 to about 25:1. The lipid moiety comprising a first click chemistry reagent and oligonucleotide comprising a second click chemistry reagent can be admixed under ambient conditions to form the amphiphilic oligonucleotide. As used herein, and unless specified otherwise, "ambient conditions" refers to room temperature and atmospheric pressure.

PEGylated Crosslinking Agents

The amphiphilic oligonucleotides can be covalently bound to a PEGylated crosslinking agent to form the cross-linked micellar SNA. The PEGylated cross-linking agent includes at least two reactive sites, each of which can form a covalent bond with the reactive group of two amphiphilic oligonucleotide and thereby crosslink the amphiphilic oligonucleotides. The PEGylated crosslinking agent advantageously increases the stability of the SNA. PEGylated crosslinking agents can include PEGylated bis(sulfosuccinimidyl)suberate to increase the stability of the SNA. As can be readily appreciated, the oligonucleotides can be cross-linked with a PEGylated crosslinking agent using other compatible reactive groups. For example, the oligonucleotide can be modified to include a succinimidyl moiety and the PEGylated crosslinking agent can have each terminus modified with an amine or other nucleophile that reacts with the succinimidyl group. Or the oligonucleotide can be modified with an alkyne and the PEGylated crosslinking agent with an azide at each terminus (or vice versa) to allow crosslinking via a click chemistry type reaction. Thus other appropriate functional groups on the oligonucleotide and the PEGylated crosslinking agent are also contemplated in this disclosure. In embodiments, the reactive sites of the PEGylated crosslinking agent comprise an amine, a hydroxyl, a succinimidyl, an alkyne, or an azide. In embodiments, at least one of the reactive sites of the PEGylated crosslinking agent comprises a succinimidyl moiety. In embodiments, each reactive site of the PEGylated crosslinking agent comprises a succinimidyl moiety.

The crosslinked micellar SNA can be cooperatively bound to a complementary SNA.

Methods of Preparing SNA

The methods disclosed herein comprise (a) admixing a polyethyleneoxide-polypropyleneoxide-polyethyleneoxide (PEO-PPO-PEO) block copolymer and a plurality of amphiphilic oligonucleotides in a buffer to form a SNA, wherein the amphiphilic oligonucleotide comprises (i) a lipid moiety and (ii) at least one reactive group, (b) admixing the resulting SNA with a PEGylated crosslinking agent to form the crosslinked SNA, wherein the PEGylated crosslinking agent comprises at least two reactive sites, each reactive site reacting with the reactive group of the amphiphilic oligonucleotide to form a covalent bond and thereby crosslink the amphiphilic oligonucleotides, and (c) optionally washing the crosslinked SNA to remove uncrosslinked amphiphilic oligonucleotides.

Admixing the PEO-PPO-PEO block copolymer and plurality of amphiphilic oligonucleotides can be performed at any suitable temperature for forming and/or maintaining PEO-PPO-PEO micelles. It is understood in the art that as the temperature of a system increases, the critical micelle concentration decreases. In embodiments, the admixing of step (a) is performed at room temperature. The PEO-PPO-PEO and amphiphilic oligonucleotides can be admixed in any suitable solvent. Suitable solvents include physiologically acceptable solvents, media, and buffers including, but not limited to HEPES buffered saline (HBS) and phosphate buffered saline (PBS). In embodiments, the PEO-PPO-PEO and amphiphilic oligonucleotides are admixed in a buffer.

The PEO-PPO-PEO can be provided as already-formed micelles or as individual polymers. The concentration of PEO-PPO-PEO, whether in the form of micelles or individual polymers, is at least equal to or greater than the critical micelle concentration of the PEO-PPO-PEO such that the individual PEO-PPO-PEO polymers will assemble into micelles and any formed PEO-PPO-PEO micelles will not disassemble. In embodiments, the PEO-PPO-PEO can be provided in a concentration in a range of about 0.5 wt. % to about 15 wt. % based on the total weight of the solution/dispersion, for example, about 0.5 wt. %, about 0.75 wt. %, about 1 wt. %, about 1.5 wt. %, about 2 wt. %, about 2.5 wt. %, about 3 wt. %, about 3.5 wt. %, about 4 wt. %, about 4.5 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, or about 15 wt. %, based on the total weight of the solution/dispersion. It is understood in the art that once the PEO-PPO-PEO is provided at the critical micelle concentration, any additional PEO-PPO-PEO or other surfactants added to the system will form micelles.

Surface functionalization of the PEO-PPO-PEO micelles with the amphiphilic oligonucleotides to form the SNA can be readily achieved. The amphiphilic oligonucleotide can be added in a suitable concentration to achieve the desired number of strands of amphiphilic oligonucleotide per PEO-PPO-PEO micelle. Suitable concentrations include at least about 0.5 µM, at least about 1 µM, at least about 5 µM, at least about 10 µM, at least about 15 µM, at least about 20 µM, at least about 25 µM, at least about 30 µM, at least about 35 µM, at least about 40 µM, at least about 45 µM, or at least about 50 µM, and up to about 100 µM, up to about 90 µM, up to about 80 µM, up to about 70 µM, up to about 60 µM, or up to about 50 µM. After admixing the PEO-PPO-PEO and the amphiphilic oligonucleotide, the mixture can be allowed to equilibrate prior to crosslinking. Without intending to be bound by theory it is believed that the lipid tail of the amphiphilic oligonucleotide intercalates into the hydrophobic core of the micelles, thereby allowing facile incorporation of the oligonucleotide into the micelles to form the SNA, without compromising the polydispersity of the micelles. The duration of equilibration of the mixture can be varied for any suitable time period for intercalating the lipid tail of the oligonucleotide into the PEO-PPO-PEO micelle. The rate of the intercalation of the lipid tail of the amphiphilic oligonucleotide into the hydrophobic core of the micelle can depend, in part, on the concentration of the amphiphilic oligonucleotide, the micelle surface to solution volume ratio, and the temperature. When the duration of equilibrium increases above 24 hours (and one of the foregoing exemplary concentrations of amphiphilic oligonucleotide is used), little difference in the amount of amphiphilic oligonucleotide incorporated into the SNA is expected (relative to a 24 hour exposure time). The concentration of oligonucleotide strands in the micellar SNAs can be determined by UV-vis spectroscopy nanoparticle tracking analysis to calculate the number of nanoparticles using dynamic light scattering technique.

The oligonucleotide strands of the resulting SNA can be crosslinked to increase stability of the SNA. Crosslinking of the oligonucleotide strands of the SNA can be achieved by admixing the SNA with a PEGylated crosslinking agent to form the crosslinked micellar SNA. Suitable solvents for crosslinking include physiologically acceptable solvents, media, and buffers, including, but not limited to HEPES buffered saline (HBS) and phosphate buffered saline (PBS). In embodiments, the SNA and PEGylated crosslinking agents are admixed in a buffer.

The PEGylated crosslinking agent can be added in any concentration suitable to achieve substantial crosslinking of the oligonucleotide strands. As used herein, "substantial crosslinking" and "substantially crosslinked" refer to at least 50%, at least 75%, at least 80%, at least 90%, or at least 95% of the reactive groups provided on the oligonucleotide strands are crosslinked. Because the PEGylated crosslinking agents have two reactive sites, the molar ratio of reactive groups to PEGylated crosslinking agent can be in a range of about 2:1 to about 4:1, or about 2:1, about 2.5:1, about 3:1, about 3.5:1, or about 4:1. An excess of PEGylated crosslinking agent (e.g., said ratio of about 2:1.1) can be used to ensure 99% or more crosslinking. Suitable concentrations include at least about 10 µM, at least about 15 µM, at least about 20 µM, at least about 25 µM, at least about 30 µM, at least about 35 µM, at least about 40 µM, at least about 45 µM, or at least about 50 µM, and up to about 100 µM, up to about 90 µM, up to about 80 µM, up to about 70 µM, up to about 60 µM, or up to about 50 µM. Suitable concentrations include at least about 10 µM, at least about 15 µM, at least about 20 µM, at least about 25 µM, at least about 30 µM, at least about 35 µM, at least about 40 µM, at least about 45 µM, or at least about 50 µM, and up to about 100 µM, up to about 90 µM, up to about 80 µM, up to about 70 µM, up to about 60 µM, or up to about 50 µM. In embodiments, the concentration of PEGylated crosslinking agent is provided in an amount that is half of the concentration of reactive groups. Particles not substantially crosslinked can be disassembled using the temperature-dependent property of PEO-PPO-PEO.

After admixing the SNA and the PEGylated crosslinking agent, the mixture can be agitated to facilitate crosslinking of the oligonucleotide strands. Without intending to be bound by theory it is believed that agitation of the mixture facilitates the diffusion of the PEGylated crosslinking agent into the SNA to access the strands of the oligonucleotide. The duration of agitation of the mixture can be varied for any suitable time period. The rate of the diffusion of the crosslinking agent into the SNA can depend, in part, on the concentration of the PEGylated crosslinking agent, the SNA surface to solution volume ratio, and the temperature. When the duration of agitation increases above 24 hours (and one of the foregoing exemplary concentrations of PEGylated crosslinking agent is used), little difference in the amount of crosslinking is expected (relative to a 24 hour exposure time). Suitable agitation times are at least about 30 min, at least about 1 h, at least about 2 h, at least about 4 h, at least about 6 h and/or up to about 24 h, up to about 18 h, up to about 16 h, up to about 14 h, up to about 12 h, up to about 10 h, or up to about 8 h.

Isolation of the crosslinked micellar SNAs from any excess PEO-PPO-PEO and any non-crosslinked, unbound amphiphilic oligonucleotides can be easily accomplished by low-temperature centrifugal filtration. Lowering the temperature of the crosslinked micellar SNA dispersion to a temperature below the critical micelle temperature of the PEO-PPO-PEO allows for the disassembly of any non-functionalized micelles (or those with low levels of functionalization) into individual polymer chains after crosslinking. These left-over block copolymer-based components, together with unincorporated oligonucleotides, can be removed via low-temperature cycles of membrane-filter-centrifugation/resuspension, where the temperature of the crosslinked micellar SNA dispersion is maintained below the temperature at which non-crosslinked polymer chains no longer remain a micelle. As used herein "micelle disassembly temperature" refers to the temperature at which non-crosslinked polymer chains no longer remain a micelle. The temperature of the crosslinked micellar SNA dispersion can be lowered to about 10° C. or less, about 8° C. or less, about 6° C. or less, or about 4° C. or less, for example, about 10° C., about 9° C., about 8° C., about 7° C., about 6° C., about 5° C., about 4° C., about 3° C., or about 2° C. In embodiments, the crosslinked micellar SNA is cooled to a temperature of less than 10° C. to remove free PEO-PPO-PEO. In embodiments, the crosslinked micellar SNA is cooled to a temperature of less than 4° C. to remove any free Pluronic F127. The low-temperature cycle of membrane-filter-centrifugation/resuspension can be performed at least 3 times, at least 4 times, or at least 5 times and/or up to about 8 times, up to about 7 times, up to about 6 times, or up to about 5 times. In embodiments, isolating the crosslinked SNA comprises filtering. In embodiments, the method comprises three low-temperature cycles of membrane-filter-centrifugation/resuspension. As shown in FIG. 1B, three low-temperature cycles was sufficient to remove substantially all of the unincorporated oligonucleotides from the SNA of the Examples, which was verified with a standard colorimetric assay. As used herein, "substantially all" of the unincorporated oligonucleotides are removed if the amount of residual, unincorporated oligonucleotides is less than about 5%, less than about 3%, or less than about 1% of the oligonucleotides in the suspension.

The isolated crosslinked micellar SNAs can retain their as-synthesized particle characteristics (e.g., polydispersity index, mean particle diameter, and/or surface charge), suggesting that the crosslinking was effective and the purification process did not cause a significant loss in the template-assembled oligonucleotide component. Imaging of the crosslinked micellar SNAs deposited on a mica surface by atomic force microscopy (AFM, as shown in FIG. 1C-D) showed the presence of nanostructures that are consistent with the estimate of a single oligonucleotide shell (in FIG. 1C-D, DNA, wherein a DNA strand 8 nm in length).

Figure 2:
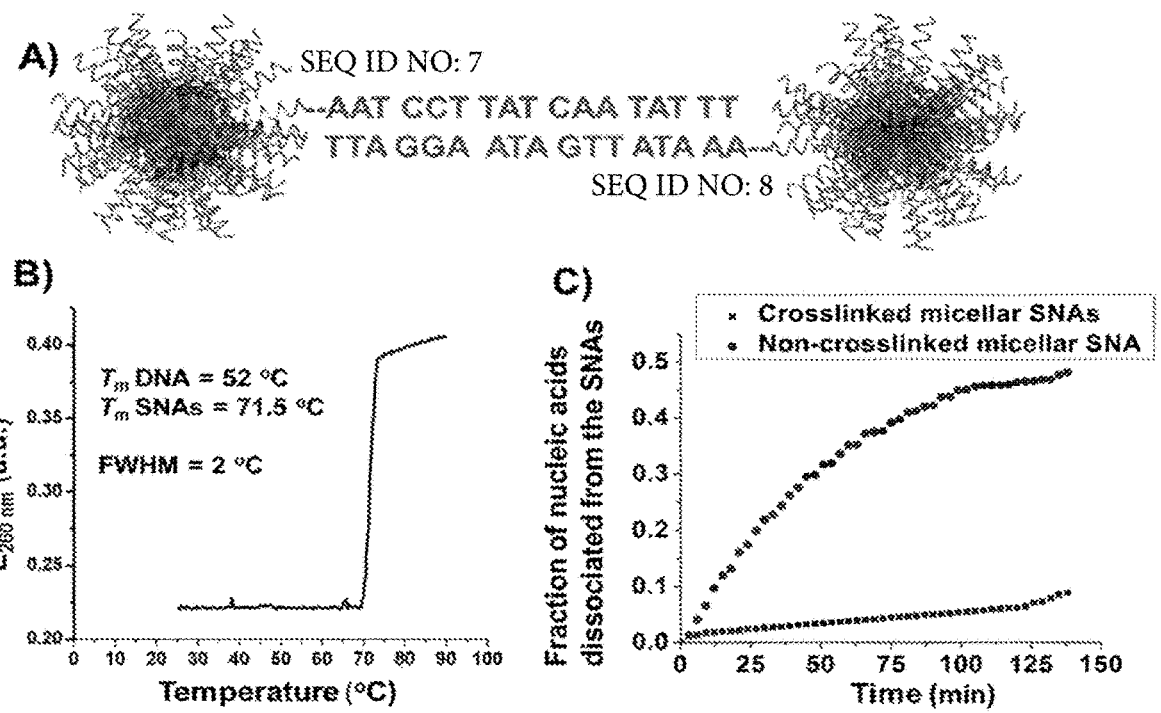
FIG. 2. (A) shows a schematic representation of the hybridization of crosslinked micellar SNAs with complementary SNAs. (B) shows the melting profile of the crosslinked micellar SNA conjugates that have been hybridized to complementary nanoconstructs. (C) shows the fractions of nucleic acids dissociated from the crosslinked SNAs and non-crosslinked micellar SNAs over time after being incubated at 37° C. in 10% serum-containing med.

SNAs can cooperatively bind to a complementary SNA partner, resulting in sharp and enhanced melting transition compared to the typical broad melting transitions observed for free DNA duplexes (FIG. 2A). This cooperative binding is a direct effect of the dense, uniform arrangement of nucleic acids on the surfaces which allows SNAs to hybridize in a polyvalent fashion. Indeed, when two samples of crosslinked micellar SNAs with complementary nucleic acids were combined at room temperature, visually observable aggregates were formed that exhibited a substantial increase in melting temperature (e.g., 72° C. vs 55° C. for the free DNA duplex, as shown in FIG. 2B) along with a narrow melting transition (full width at half maximum ~2° C.; FIG. 2B).[4]

The crosslinked micellar SNAs presented herein exhibit remarkable stability in biological media at physiological conditions. The crosslinked micellar SNAs can be stored at 37° C. for at least 3 days, at least 5 days, or at least 7 days without demonstrating oligonucleotide leakage or interparticle fusion, as analyzed by direct gel electrophoresis of the nanoconstruct. Without intending to be bound by theory, it is believed that the thermal stability of the SNAs can be attributed to the electrostatic repulsive forces of the negatively charged oligonucleotide strands on the particle surface. It is further believed that the oligonucleotide corona is accompanied by a dense counter-ion cloud that decreases the propensity of SNAs interaction with nucleases and the crosslinking of the nucleic acids extends its serum stability. Thus, the SNAs disclosed herein can be used for delivery of a therapeutic agent encapsulated in the SNA and released upon cellular uptake. For example, a chemotherapeutic agent can be included in the SNA and can then be released after cellular uptake.

The ease of synthesis and scalability from readily available, non-toxic starting materials makes crosslinked micellar SNAs an advantageous route for effective intracellular delivery of therapeutically active nucleic acids with attractive properties. Furthermore, crosslinked micellar SNAs are advantageously in a size range which allows for enhanced circulation and tumor penetration, thereby allowing for effective delivery of therapeutically active nucleic acids that exhibit immunomodulation in diseased cells.

Uses of SNAs in Gene Regulation/Therapy

Methods for inhibiting gene product expression provided herein include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of an SNA. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell-culture assay, generally as a predictable measure of a degree of inhibition that can be expected in vivo resulting from use of a specific type of SNA and a specific oligonucleotide.

In some aspects of the disclosure, it is contemplated that a SNA performs both a gene inhibitory function as well as a therapeutic agent delivery function. In such aspects, a therapeutic agent is encapsulated in a SNA of the disclosure and the particle is additionally functionalized with one or more oligonucleotides designed to effect inhibition of target gene expression. In further embodiments, a therapeutic agent is attached to the SNA of the disclosure.

In various aspects, the methods include use of an oligonucleotide which is 100% complementary to the target polynucleotide, i.e., a perfect match, while in other aspects, the oligonucleotide is at least (meaning greater than or equal to) about 95% complementary to the polynucleotide over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the oligonucleotide to the extent that the oligonucleotide is able to achieve the desired degree of inhibition of a target gene product.

It is understood in the art that the sequence of an antisense compound need not be 100% complementary to that of its target nucleic acid to be specifically hybridizable. Moreover, an oligonucleotide can hybridize over one or more segments such that intervening or adjacent segments are not involved in the hybridization event (e.g., a loop structure or hairpin structure). The percent complementarity is determined over the length of the oligonucleotide. For example, given an antisense compound in which 18 of 20 nucleotides of the antisense compound are complementary to a 20 nucleotide region in a target polynucleotide of 100 nucleotides total length, the oligonucleotide would be 90 percent complementary. In this example, the remaining noncomplementary nucleotides can be clustered or interspersed with complementary nucleobases and need not be contiguous to each other or to complementary nucleotides. Percent complementarity of an antisense compound with a region of a target nucleic acid can be determined routinely using BLAST programs (basic local alignment search tools) and Power-BLAST programs known in the art (Altschul et al., *J. Mol. Biol.*, 1990, 215, 403-410; Zhang and Madden, *Genome Res.*, 1997, 7, 649-656).

Accordingly, methods of utilizing SNAs in gene regulation therapy are provided. This method comprises the step of hybridizing a polynucleotide encoding said gene product with one or more oligonucleotides complementary to all or a portion of said polynucleotide, said oligonucleotide being attached to a SNA, wherein hybridizing between said polynucleotide and said oligonucleotide occurs over a length of said polynucleotide with a degree of complementarity sufficient to inhibit expression of said gene product. The inhibition of gene expression can occur in vivo or in vitro. In embodiments, the expression of the gene product is inhibited in vivo. In embodiments, the expression of the gene product is inhibited in vitro.

The oligonucleotide utilized in this method is either RNA or DNA. In embodiments, the oligonucleotide comprises RNA. The RNA can be a non-coding RNA. The non-coding RNA can be an inhibitory RNA (RNAi). The RNA can be an inhibitory RNA (RNAi) that performs a regulatory function, and in various embodiments is selected from the group consisting of a small inhibitory RNA (siRNA), an RNA that forms a triplex with double stranded DNA, and a ribozyme. Alternatively, the RNA is microRNA that performs a regulatory function. The oligonucleotide can be DNA. The DNA is, in some embodiments, an antisense-DNA.

In another aspect of the disclosure, a SNA is used in a method for treating a traumatic brain injury (TBI). In the United States, there have been over 244,000 cases of TBI in the military since 2000, and it is the leading cause of death and disability in people under the age of 45. Further, it is currently difficult to predict the neurological outcome of "mild severity" incidents, and the secondary phase of the injury (e.g., inflammation, ischemia, and apoptosis) is very difficult to treat.

Thus, in some embodiments, methods of the disclosure are directed to the use of a SNA designed to target and regulate the expression of a gene product implicated in TBI. For example and without limitation, the target gene product is selected from the group consisting of histone deacetylase (HDAC), BCL2-associated X (BAX), a matrix metallopeptidase/metalloproteinase (MMP; including, without limitation, matrix metallopeptidase 9 (MMP-9)), a hypoxia-inducible factor (HIF; including, without limitation, hypoxia inducible factor 1 alpha (HIF1-α)), and calpain.

Use of SNA in Immune Regulation

Toll-like receptors (TLRs) are a class of proteins, expressed in sentinel cells, that plays a key role in regulation of innate immune system. The mammalian immune system uses two general strategies to combat infectious diseases. Pathogen exposure rapidly triggers an innate immune response that is characterized by the production of immunostimulatory cytokines, chemokines, and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 4, TLR 8, and TLR 9, that response to specific oligonucleotide are located inside special intracellular compartments, called endosomes. The mechanism of modulation of TLR 4, TLR 8, and TLR9 receptors is based on DNA-protein interactions.

Synthetic immunostimulatory oligonucleotides that contain CpG motifs that are similar to those found in bacterial DNA stimulate a similar response of the TLR receptors. Therefore immunomodulatory oligonucleotides have various potential therapeutic uses, including treatment of immune deficiency and cancer. Employment of liposomal nanoparticles functionalized with immunomodulatory oligonucleotides will allow for increased preferential uptake and therefore increased therapeutic efficacy. Notably, smaller particles (25 to 40 nm) such as those provided herein penetrate tissue barriers more efficiently, therefore providing more effective activation of innate immune responses. Thus, SNAs of 30 nm in size, functionalized with stabilized with functional CpG motif-containing DNA, would provide enhanced therapeutic effect.

Down regulation of the immune system would involve knocking down the gene responsible for the expression of the Toll-like receptor. This antisense approach involves use of SNAs functionalized with specific antisense oligonucleotide sequences to knock out the expression of any toll-like protein.

Accordingly, methods of utilizing SNAs for modulating toll-like receptors are disclosed. The method either up-regulates or down-regulates the Toll-like-receptor through the use of a TLR agonist or a TLR antagonist, respectively. The method comprises contacting a cell having a toll-like receptor with an SNA. The toll-like receptors modulated include toll-like receptor 1 (TLR1), toll-like receptor 2 (TLR2), toll-like receptor 3 (TLR3), toll-like receptor 4 (TLR4), toll-like receptor 5 (TLR5), toll-like receptor 6 (TLR6), toll-like receptor 7 (TLR7), toll-like receptor 8 (TLR8), toll-like receptor 9 (TLR9), toll-like receptor 10 (TLR10), toll-like receptor 11 (TLR11), toll-like receptor 12 (TLR12), and toll-like receptor 13 (TLR13). In embodiments, modulating toll-like receptors can be performed in vitro. In embodiments, modulating toll-like receptors can be performed in vivo.

Use of SNA in Nanoflare Technology

In additional aspects of the disclosure, an SNA is used to detect an intracellular target. Such methods are disclosed in U.S. Pat. No. 8,507,200, which is incorporated by reference herein in its entirety.

Briefly, an oligonucleotide containing a recognition sequence that is specific for a target molecule is attached to an SNA as described herein. Thus, "recognition sequence" as used herein is understood to mean a sequence that is partially or completely complementary to a target molecule of interest.

The SNA with attached oligonucleotide containing a recognition sequence is initially associated with a reporter sequence. As used herein, a "reporter sequence" is understood to mean a sequence that is partially or completely complementary and therefore able to hybridize to the recognition sequence. The reporter sequence is labeled with a detectable label (such as, without limitation, a fluorophore), and is also referred to as a nanoflare. The reporter sequence is in various aspects comprised of fewer, the same or more bases than the recognition sequence, such that binding of the recognition sequence to its target molecule causes release of the hybridized reporter sequence, thereby resulting in a detectable and measurable change in the label attached to the reporter sequence.

Instrumentation.

UV-vis absorbance spectra and thermal denaturation curves were collected on an Varian Cary 5000 UV-vis spectrometer (Varian, Inc., Palo Alto, Calif.), or equivalent, using quartz cuvettes with a 1 cm path length.

Matrix-assisted laser desorption/ionization time-of-flight (MALDI-ToF) data was obtained on a Bruker AutoFlex III MALDI-ToF mass spectrometer (Bruker Daltonics Inc., MA, USA), or equivalent. For MALDI-ToF analysis, the matrix was prepared by mixing an aqueous solution of ammonium hydrogen citrate (0.6 µL of a 35 wt % solution (15 mg in 30 µL of $H_2O$)) and 2-hydroxypicolinic acid (Fluka #56297, 2 mg in $H_2O$:MeCN (30 pt of a 1:1 v/v mixture). An aliquot of the DNA (~0.5 pt of a 150 µM solution) was then mixed with the matrix (1:1) and the resulting solution was added to a steel MALDI-ToF plate and dried at 25 C for 1 h before analysis. Samples were detected as negative ions using the linear mode. The laser was typically operated at 10-20% power with a sampling speed of 10 Hz. Each measurement averaged for five hundred scans with the following parameters: ion source voltage 1=20 kV, ion source voltage 2=18.5 kV, lens voltage=8.5 kV, linear detector voltage=0.6 kV, deflection mass=3000 Da.

Centrifugation was carried out in a temperature-controlled Eppendorf centrifuge 5430R (Eppendorf, Hauppauge, N.Y.), or equivalent.

Transmission electron microscopy (TEM) was performed on a Hitachi H2300 transmission electron microscope (Hitachi High-Technologies Corp., Tokyo, Japan), or equivalent, operating at an accelerating voltage of 200 kV.

Dynamic light scattering (DLS) and zeta potential measurements were collected on a Zetasizer Nano ZS (Malvern Instruments, UK), or equivalent, equipped with a He—Ne laser (633 nm).

EXAMPLES

Materials.

Unless otherwise noted, all reagents were purchased from commercial sources and used as received. For oligonucleotide synthesis, all phosphoramidites and reagents were purchased from Glen Research (Sterling, Va.). The $BS(PEG)_5$ (PEGylated bis(sulfosuccinimidyl)suberate) crosslinker and buffer solutions were purchased from Thermo Fisher Scientific Inc. (Richardson, Tex.). Gold nanoparticles were purchased from Ted Pella (Redding, Calif.). Amicon® Ultra centrifugal filter units were purchased from EMD Millipore (Billerica, Mass.). All other reagents were purchased from Sigma-Aldrich (St. Louis, Mo.). Ultrapure deionized (DI) $H_2O$ (18.2 MΩ·cm resistivity) was obtained from a Millipore system (Milli-Q Biocel).

Example 1: Oligonucleotide Synthesis

The oligonucleotides described in Table 1 were synthesized on CPG support using an automated Expedite Nucleotide system (MM48 Synthesizer, Bioautomation, Plano, Tex.), or equivalent. Whenever a modified (i.e., non-nucleoside-bearing) phosphoramidites was used, the coupling time was extended to 20 min compared to the usual 90 seconds for a typical phosphoramidite coupling. After synthesis, the completed DNA was cleaved off the CPG support through an overnight exposure to aqueous 8 M ammonium hydroxide (28-30 wt %). Excess ammonium hydroxide was removed from the cleaved DNA solution by passing a stream of dry nitrogen gas over the content of the vial until the characteristic ammonia smell disappears. The remaining solution was then passed through a 0.2 µm cellulose acetate membrane filter to remove the solid support and then purified on a Varian ProStar 210 (Agilent Technologies, CA, USA) equipped with reverse-phase semi-preparative Varian column ((Agilent Technologies, 250 mm×10 mm, Microsorb 300 Å/10 µm/C4), gradient=100:0 v/v 0.1 M TEAA (aq): MeCN (TEAA (aq)=triethylammonium acetate, aqueous solution), and increased to pure acetonitrile in 30 min, flow rate=3 mL/min for each 1 µmol DNA). The product fractions collected were concentrated using lyophilization. The lyophilized oligonucleotides were then re-suspended in ultrapure deionized water and their concentrations were measured using UV-vis spectroscopy. The purity of synthesized oligonucleotides was assessed using MALDI-ToF.

TABLE 1

| Particle Type | Application | Sequence | SEQ ID NO |
|---|---|---|---|
| $T_{20}$ | Characterization of SNAs | 5'-$T_{20}$-$(NH_2)_5$-$(Spacer18^a)_2$-$DBCO^b$-3' | 1 |
| Cy5-$T_{20}$ | Characterization and cellular uptake | 5'-Cy5-$T_{20}$-$(NH_2)_5$-$(Spacer18)_2$-DBCO-3' | 2 |
| Melt A | Melt analysis | 5'-DBCO-$(NH_2)_5$-$T_4$-AATCCTTATCAATATTT-3' | 3 |
| Melt B | Melt analysis | 5'-DBCO-$(NH_2)_5$-$T_4$-AAATATTGATAAGGATT-3' | 4 |
| IS-1826 | Immunostimulation | 5'-TCCATGACGTTCCTGACGTT-$T^5$-$(Spacer18)_2$-DBCO-3' | 5 |
| Scrambled | Immunostimulation | 5'-$T_{20}$-$(NH_2)_5$-$(Spacer18)_2$-DBCO-3' | 1 |
| IS-7909 | Immunostimulation | 5'-TCGTCGTTTTGTCGTTTTGTCGTT-$T_5$-$(NH_2)_5$-$(Spacer18)_2$-DBCO-3' | 6 |

TABLE 1-continued

| Particle Type | Application | Sequence | SEQ ID NO |
|---|---|---|---|
| Scrambled | Immunostimulation | 5'-T$_{20}$-(NH$_2$)$_5$-(Spacer18)$_2$-DBCO-3' | 1 |

[a]Spacer18 = 18-O-Dimethoxytritylhexaethyleneglycol,1-[(2-cyanoethyl)-(N,N-diisopropyl)]-phosphoramidite
[b]DBCO = 5'-Dimethoxytrityl-5-[(6-oxo-6-(dibenzo[b,f]azacyclooct-4-yn-1-yl)-capramido-N-hex-6-yl)-3-acrylimido]-2'-deoxyuridine,3'-[(2-cyanoethyl)-(N,N-diisopropyl)]-phosphoramidite Thus, Example 1 demonstrates the preparation of an oligonucleotide in accordance with the disclosure.

Example 2: Synthesis of Lipid-Conjugated Oligonucleotides

For the synthesis of lipid-conjugated oligonucleotides, the purified DBCO-terminated oligonucleotides prepared according to Example 1 (1 mol, see Table 1) were re-suspended in an aliquot of water (250 µL). In a separate Eppendorf tube, 10 µmol of DPPE (1,2-dipalmitoyl-sn-glycero-3-phosphoethanolamine-N-(6-azidohexanoyl) (ammonium salt), Avanti Polar Lipids, AL, USA) was suspended in ethanol (250 µL). The lipid solution was then added to the oligonucleotide solution and the resulting mixture was allowed to shake overnight at room temperature on a benchtop Thermomixer R 5355 (Eppendorf AG North America, NY) instrument, or equivalent, at 850 rpm. The following day, the content was dried on a Labconco centrivap (Labconco, Kansas City, Miss. USA). The obtained dried pellet was re-suspended in ultrapure deionized water (300 µL) and the resulting mixture was extracted with chloroform (3×300 µL) to remove excess lipid. The lipid-conjugated DNA was purified from the unconjugated DNA via size exclusion chromatography on Sepharose CL6B (Sigma).

Thus, Example 2 demonstrates the preparation of an amphiphilic oligonucleotide in accordance with the disclosure.

Example 3: Synthesis of Crosslinked Micellar SNAs

For the preparation of micellar SNAs, free lipid-conjugated DNA strands (10 nmol for T$_3$_sequence) was added to an aliquot of aqueous PEO-PPO-PEO block copolymer, Pluronic F127 (1 mL of a 2 wt % solution in 1×HBS (20 mM of HEPES buffer, 150 mM aqueous NaCl)). The resulting solution was allowed to shake at room temperature overnight on a benchtop Thermomixer R 5355 (Eppendorf AG North America, Hauppauge, N.Y.) instrument, or equivalent. To crosslink the DNA strands, a BS(PEG)$_5$ linker (2.5 equiv of DNA concentration, or 50% of the amino group concentration for achieving a theoretical 100% crosslink density) was next added and the resulting solution allowed to shake for 6 h more. In situ analysis of the reaction mixture shows particles with an increased size and a more negative surface charge, demonstrating successful functionalization of the micelle core with the nucleic acid strands. To remove the unincorporated Pluronic F127, the reaction mixture was cooled to 4° C. and then centrifuged in an Amicon® Ultra centrifugal filter units (100,000 MWCO, 7500 g) at 4° C. until ~100 µL of solution was retained. This solution of the desired micellar SNA products were subjected to three washes with 1×HBS and passed through a 0.1 µm syringe filter before use.

To quantify the incorporated Pluronic F127, the collected filtrates were collected separately and the Pluronic F127 concentration in each filtrate fraction was determined by a previously reported colorimetric assay method with minor modifications. In brief, cobalt nitrate hexahydrate (0.3 g) and ammonium thiocyanate (1.2 g) were dissolved in water (3 mL) to make a cobalt thiocyanate reagent. Into an Eppendorf tube were combined an aliquot (100 µL) of the cobalt thiocyanate solution, an aliquot (40 µL) of the filtrate solution, ethyl acetate (200 µL), and ethanol (80 µL). The resulting semi-cloudy mixture was vortexed gently and centrifuged at 14000 g for 1 min. The blue supernatant was removed and the left-over blue pellet was washed with diethyl ether several (~5) times until the supernatant became colorless. The resulting pellet was then dissolved in acetone (1 mL) and subjected to UV-vis measurement. The absorbance value at 623 nm was compared to a calibration curve prepared from the colorimetric assay of standard Pluronic F127 solutions over a 0-2.5 wt % concentration range. The DNA:Pluronic F127 molar ratio in the purified solution is 0.55 (assuming a rounded-up molecular weight of Pluronic F127 to be 10,000 and the DNA sequence to be CyT-T$_{30}$ (Table 1)).

The concentration of DNA strands in the crosslinked micellar SNAs is estimated against the UV-vis extinction coefficient for DNA at 260 nm (ϵ=243600 L/mol cm for a T$_{30}$ sequence) after disassembly (by sonicating with 0.1 M HCl and 0.01 wt % SDS solution for 30 sec and left in a 37° C. water bath for 10 min). As the initial Pluronic F127 template at a high 2 wt % concentration does not show a significant absorption at 260 nm, the small amount that may be retained in the dissembled crosslinked micellar SNAs does not interfere with calculations of the DNA concentrations.

The purified micellar SNAs retain many of the as-synthesized (in situ) particle characteristics (particle size, poly dispersity, surface charge), demonstrating that the crosslinking was effective and the purification process did not cause a significant loss in the template-assembled DNA component.

Thus, Example 3 demonstrates the preparation of a crosslinked micellar SNA according to the disclosure.

Example 4: Characterization of Crosslinked Micellar SNAs

Dynamic Light Scattering (DLS)

The particle size distribution, and charge characterization of micellar SNAs was carried out via dynamic light scattering. To measure the size of nanoparticles, non-invasive backscatter method (detection at 173° scattering angle) was used. The collected data were fitted, using the method of cumulants, to the logarithm of the correlation function, yielding the diffusion coefficient D. The calculated diffusion coefficient was applied to the Stokes-Einstein equation ($D_H=k_B T/3\pi\eta D$, where $k_B$ is the Boltzmann constant, T is the absolute temperature, and $\eta$ is the solvent viscosity ($\eta$=0.8872 cP for water at 25° C.)), to obtain the hydrodynamic diameters ($D_H$) of the nanoparticles (NPs). The reported DLS size for each sample was based on six measurements, each of which was subjected to non-negative least squares analysis.

Scanning and Transmission Electron Microscopy (STEM) Imaging.

In a typical experiment, the micellar SNAs sample was first "stirred up" gently using a micropipetting technique to ensure complete homogeneity (even though there was no visual evidence of precipitation). An aliquot (1.5 µL) of this solution was then placed on a TEM carbon sample grid (Ted Pella, Inc. #01820). After 1 min, the excess solution was gently wicked away from the grid with a piece of filter paper. The excess of salt was removed from the grid by touching it briefly with a drop of ultrapure DI water and then gently wicking away the excess solution. The grid was allowed to air-dry for 1 h before being stained with a drop (1.5 µL) of uranyl acetate solution (2 wt % in water). After 20 s, the excess solution was gently wicked away from the grid with a piece of filter paper and the grid was allowed to air-dry prior to analysis.

Atomic Force Microscropy (AFM) Imaging.

Sample for AFM imaging was carried out by drop-casting a small drop (2 µL of 2 µM solution of micellar SNAs) in $H_2O$ and air-drying the droplet on freshly cleaved muscovite mica (Ted Pella, Inc.). The DNA-functionalized particles appeared monodispersed on the substrate under the same conditions.

FIG. 1A shows DLS histograms of the Pluronic F-127 templates before DNA insertion and the crosslinked micellar SNAs. FIG. 1B shows a plot of the amount of free, unincorporated DNA in the dispersion of micellar SNAs, showing complete removal of unincorporated DNA after 3 centrifugal washes at 4° C. The inset is a photographic image of the filtrates, showing the blue color of Cy-5 labeled DNA visually disappears in the $3^{rd}$ wash. FIG. 1C is an AFM image of the crosslinked micellar SNAs after drop-cast and dried on mica, showing crosslinked micellar SNAs. FIG. 1D is an AFM image of the crosslinked micellar SNAs after drop-cast and dried on mica, showing crosslinked micellar SNAs. The inset shows a distribution centering at 30±8 nm, slightly smaller than the DLS data as expected for dried materials.

Gel Electrophoresis.

The gel electrophoresis experiments were performed on a 1% agarose gel made in 1×TBE buffer (Tris/borate/EDTA) buffer. An aqueous solution of glycerol (30% v/v) was used as a loading agent. The gel was allowed to run at 80 V in 1×TBE buffer for 60 min. After the run was complete, the gel was imaged with Flourchem Q (BioRad, Hercules, Calif.) with Cy5 filter.

Thermal Stability

An aliquot (1 mL of a 10 µM stock solution) of the Cy5-labeled micellar SNAs was transferred into an 1.5 mL safe-lock Eppendorf and diluted in 1×PBS (final concentration 1 µM). The resulting solution was incubated at 37° C. and 100 µM aliquots were collected after one week for analysis by gel electrophoresis.

Figure 5:
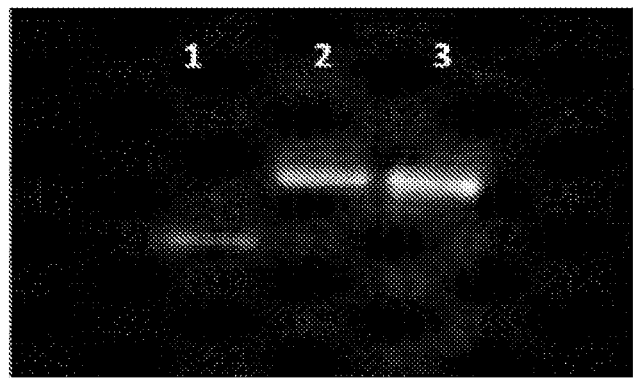
FIG. 5 shows an image of a 1% agarose gel electrophoresis of micellar SNAs.

FIG. 5 shows an image of a 1% agarose gel electrophoresis of micellar SNAs. The negatively charged DNA corona of the micellar SNA surface allows the particles to move through the gel under the influence of the applied voltage. Differences in the size and charge between the free strand (lane 1) and micellar SNAs (freshly prepared, lane 2; after 7 days of incubation, lane 3) are reflected through the distances they traveled on the gel, as visualized using the Cy5 channel. That lanes 2 and 3 each only show a single band at a similar distance from the top of the gel confirms no thermal degradation and no dissociation of the DNA from the construct after 7 days of incubation at physiological temperature.

Example 5: Melt Analysis for Micellar SNAs

The cooperative melting profiles of materials assembled from complementary SNAs are diagnostic indicators of the SNA structure. This cooperative binding is a consequence of the dense, uniform arrangement of nucleic acids on their surfaces, which allows them to hybridize in a polyvalent fashion. A DNA-hybridized nanoparticle aggregate (FIG. 3A) was formed using two different micellar SNAs possessing sequences Melt A and Melt B as described in Table 1 and a 1:1 DNA stoichiometry. Nanoparticle aggregate was formed by mixing aliquots of the solutions of the two particles together and added enough water and conc. aq NaCl to make a mixture suitable for melt analysis (final DNA concentration of one component=0.5 µM, total volume=1 mL, final NaCl concentration=500 mM). The resulting mixture was allowed to hybridize overnight and then subjected to heating (from 25 to 90° C.) inside the UV-vis spectrometer at a rate of 0.5° C./min, while the absorbance at 260 nm was continuously monitored.

FIG. 2A shows a schematic representation of the hybridization of crosslinked micellar SNAs with complementary SNAs. FIG. 2B shows the melting profile of crosslinked micellar SNA conjugates that have been hybridized to complementary nanoconstructs.

Example 6: Co-Localization of Pluronic F127 and Lipid-Conjugated DNA

Into an Eppendorf tube was combined a DMSO aliquot (1 µL of a 25 mM solution) of the hydrophobic dye Dil Stain (1,1'-dioctadecyl-3,3,3',3'-Tetramethylindocarbocyanine perchlorate (aka—'Dil'; $DilC_{18}$(3)) and an aliquot (1 mL) of a Pluronic F127 solution (1% w/v). The resulting solution (final dye concentration=25 µM) was allowed to shake for 4 h on a benchtop shaker to form the Dil-encapsulated Pluronic F127 micelles, which were purified from the free dye by size-exclusion chromatography (NAP 25, GE Healthcare, Arlington Heights, Ill., USA).

The purified Dil-encapsulated micelles were further incubated overnight with lipid-functionalized DBCO-BHQ-2 dT-$(NH_2)_5$-$T_{20}$ sequence to form the Dil-encapsulated, BHQ-2-labeled micellar SNA, which was then isolated following the functionalization and purification protocols discussed above. The quenching of the Dil dye due to the proximity of BHQ-2-labeled DNA with the Pluronic F127 template in this latter sample was confirmed by the decrease of a fluorescence from the Dil dye in the core.

Example 7: Serum Stability Studies

The serum stability of crosslinked micellar SNAs was assessed using purified $DilC_{18}$-encapsulated micelles that were functionalized with BHQ (black hole quencher)-$T_{20}$-lipid material to form a $DilC_{18}$-encapsulated, BHQ-2-labeled micellar SNA sample (10 µM final DNA concentration, volume=3 mL). An aliquote (1.5 mL) of this material was removed and added to a separate Eppendorf tube. The $BS(PEG)_5$ crosslinker was added to the remaining mixture to form crosslinked micellar SNAs. The two samples were purified using size-exclusion chromatography with Sepharose CL-4B (Sigma-Aldrich). The quenching of the $DiIC_{18}$ dye due to the proximity of the BHQ-2-labeled DNA was confirmed by the decrease of its fluorescence. To analyze the serum stability of non-crosslinked and crosslinked micellar SNAs, the $DiIC_{18}$-encapsulated versions of these constructs were suspended in a solution comprising 10 vol % fetal bovine serum (FBS) in HBS at 37° C. The release of the dye at 37° C., as represented by the intensity of the solution fluorescence at 560 nm, was monitored continuously for a period of 200 minutes with sample excitation at 540 nm on a BioTek Synergy H4 Hybrid Reader (BioTek, Inc., Winooski, Vt., USA).

In an Eppendorf tube an aliquot from the stock solution of the Cy5-labeled micellar SNAs (stock solution: 1 mL of a 10 uM) was combined with a solution comprising 10% fetal bovine serum (FBS) in 1×PBS to achieve a final concentration of 2.5 uM of final DNA concentration. The resulting mixture was incubated at 37° C. and 100 uL aliquots were collected after 2, 4 and 8 h for analysis by gel electrophoresis.

Figure 6:
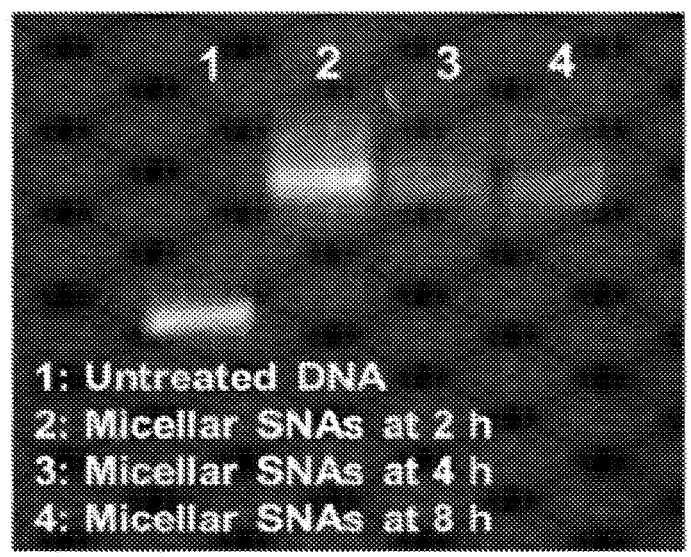
FIG. 6 shows an image of a 1% agarose gel electrophoresis of crosslinked micellar SNAs after being incubated in a 10% FBS solution in HBS for 2, 4, and 8 h (lanes 2-4).

FIG. 6 shows an image of a 1% agarose gel electrophoresis of crosslinked micellar SNAs after being incubated in a 10% FBS solution in HBS for 2, 4, and 8 h (lanes 2-4). For reference, free DNA (not treated with the media) was also include, in lane 1. Dissociation of the DNA from the construct was not observed after 8 h of incubation.

As described in the previous paragraphs, the stability of the SNAs in serum can be experimentally determined by measuring the increase in fluorescence of $DiIC_{16}$ dye encapsulated in the Pluronic F127 core. $DiIC_{16}$-encapsulated Pluronic F127 core was functionalized with lipid-tailed DNA with a quencher modification. The dissociation of the lipid-tailed DNA from the core allows for an increase in fluorescence. In this experiment, the $DiIC_{16}$-containing micellar SNAs with BHQ modifications were incubated at 37° C. in 10 vol % serum media and the fluorescence was recorded for 2 h. A similar study was performed on the non-crosslinked micellar SNAs of same composition. Minimal increase in fluorescence was observed for crosslinked micellar SNAs suggested that the structures remained stable in serum. However, the non-crosslinked micellar SNAs showed a significant increase in fluorescence due to the dissociation of intercalated DNA strands from the $DiIC_{16}$ containing Pluronic F127 core. FIG. 2C shows the fraction of nucleic acids dissociated from crosslinked SNAs and non-crosslinked micellar SNAs over time after being incubated at 37° C. in 10 vol % serum-containing med. Unlike their non-crosslinked counterparts, the crosslinked micellar SNAs show no dissociation on incubating the particles with serum at 37° C.

Thus, in Example 7, crosslinking the nucleic acids of the SNAs of the disclosure was shown to result in improved stability of the micellar SNA structures against degradation by nucleases, and increased serum stability.

Example 8: Cell Culture Studies

HEK-Blue™-mTLR9 cells (InvivoGen, NY, USA) and Ramos-Blue cells (InvivoGen), derivatives of HEK-293 cells and Ramos cells, respectively, both stably expressing a secreted alkaline phosphatase (SEAP) inducible by NF-κB, were cultured as recommended by the supplier.
Confocal Microscopy.

The HEK-Blue cells were plated on 35 mm FluoroDish™ chambers at 30% confluency. Cy5-labeled micellar SNAs (0.1 µM DNA) were incubated with cells (100,000 cell/well) in OptiMEM serum-free medium (Invitrogen, Grand Island, N.Y.) for 4 h and then washed three times with 1×PBS. After the incubation, the cell media was switched to normal serum-containing DMEM medium (Life Technologies, Grand Island, N.Y.) for 1 h before imaging. The resulting cell suspension was centrifuged and the supernatant was removed. The nuclei of incubated and untreated cells were stained with Hoechst 3342 (Invitrogen, NY, USA) following the manufacturer's protocol. The pellet was re-suspended in mounting medial (ProLong® Gold Antifade Mountant, ThermoFisher Scientific; 50 µL final volume). A 10 µL solution was added on a glass slide and allowed to dry in a dark chamber for 48 h. Confocal microscopy imaging of these live cells were carried out on an a Zeiss LSM 510 inverted laser-scanning confocal microscope (Carl Zeiss, Inc., NY, USA) equipped with a Mai Tai 3308 laser (Spectra-Physics, CA, USA) at 40× magnification. The Hoechst dye was excited at 780 nm and emission data were collected at 390-495 nm; the Cy5 dye was excited at 640 nm and emission data were collected at 650-710 nm.

Figure 3:
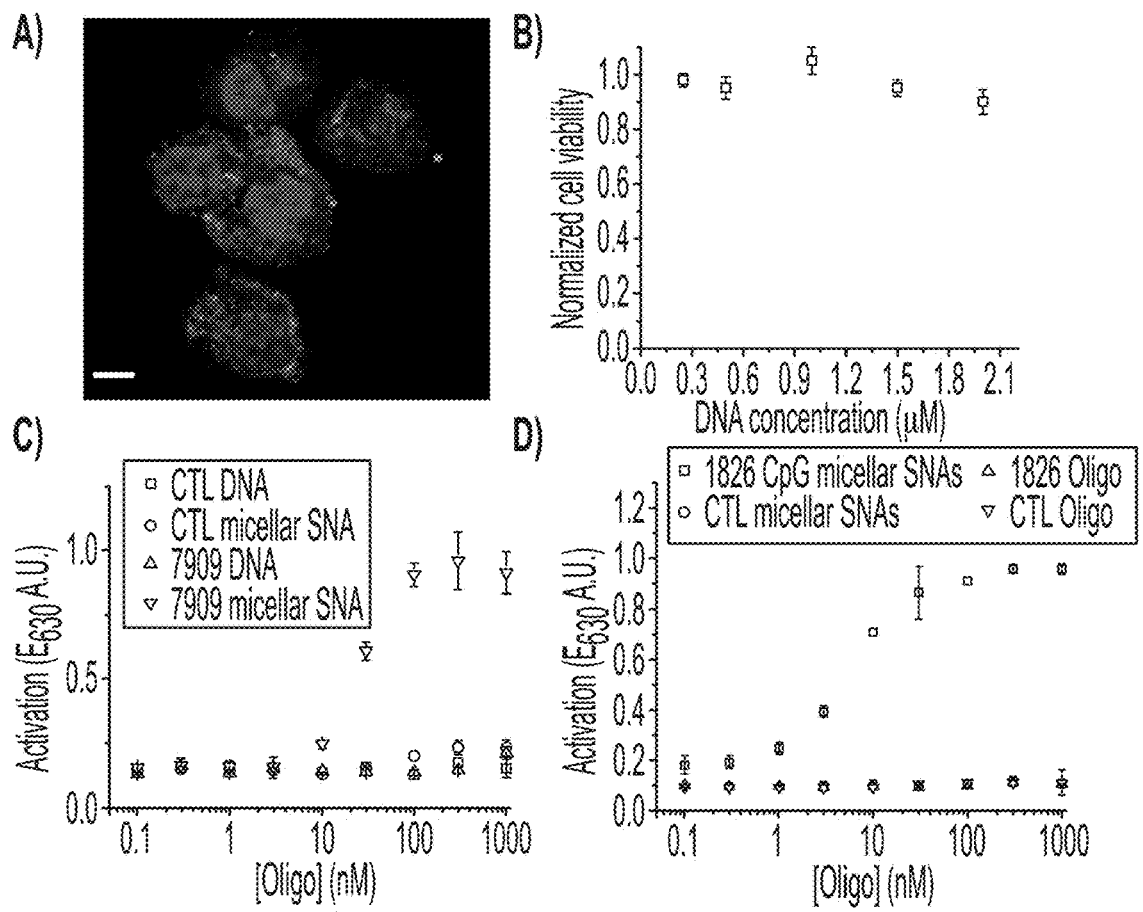
FIG. 3. (A) shows a confocal fluorescent micrograph of HEK-Blue cells that were incubated with 100 nM Cy5-labeled crosslinked micellar SNAs for 4 h. (B) shows a plot of normalized cell viability for HEKBlue mTLR9 cells after treatment with micellar SNAs at different DNA concentrations for 24 h. (C) shows a plot of potency of 7909 CpG-bearing immunostimulatory crosslinked micellar SNAs, control and crosslinked micellar SNAs ($T_{20}$), and the two unmodified linear nucleic acids in HEK-Blue cells. (D) shows a plot of potency of 1826 CpG-bearing immunostimulatory crosslinked micellar SNAs, control and crosslinked micellar SNAs ($T_{20}$), and the two unmodified linear nucleic acids in Ramos Blue cells.

FIG. 3A shows a confocal fluorescent micrograph of HEK-Blue cells that were incubated with 100 nM Cy5-labeled crosslinked micellar SNAs for 4 h (Scale bar 20 µm). FIG. 3B shows a plot of normalized cell viability for HEKBlue mTLR9 cells after treatment with micellar SNAs at different DNA concentrations for 24 h. FIG. 3C shows a plot of potency of 7909 CpG-bearing immunostimulatory crosslinked micellar SNAs, control crosslinked micellar SNAs ($T_{20}$), and the two unmodified linear nucleic acids in HEK-Blue cells. Immunostimulatory micellar SNAs demonstrated an increased potency against control liposomal and micellar SNAs (T20) and unmodified linear nucleic acids in HEK-Blue cells. FIG. 3D shows a plot of potency of 1826 Cp-G-bearing immunostimulatory crosslinked micellar SNAs, control crosslinked micellar SNAs ($T_{20}$), and the two unmodified linear nucleic acids in Ramos Blue cells.) Micellar SNAs again show higher potency.
Flow Cytometry Experiments.

A comparative cell-uptake study between the micellar SNAs and free DNA was carried out using HEK-BLUE cells. Cells were plated on a 96 well plate in DMEM medium (supplemented with fetal bovine serum (10 vol %), penicillin (0.2 units/mL), and streptomycin (0.1 µg/mL), Normocin™ (100 µg/mL) 2 mM L-glutamine); 100 µL of media/well) and incubated with either free-DNA or micellar SNAs (final DNA concentration 0.1 µM) for 16 h. The fluorescence was normalized using untreated cells as a negative control for these time-points. At the end of incubation period, the cells were washed 3 times with 1×PBS. The resulting cell suspension was subjected to flow cytometry using the Cy5 intensity channel on a Guava easyCyte 8HT instrument (Millipore, Billerica, Mass., USA). The error-values were calculated using the standard error of the mean of median signal from different wells representing one type of sample.

As expected, the nucleic acid shell on the surface of micellar SNAs of the disclosure also facilitated their rapid cellular uptake into macrophages such as HEK-Blue cells. Indeed, incubating HEK-Blue cells with micellar SNAs comprising Cy5-labeled DNA for 4 h resulted in excellent cellular uptake in comparison to free DNA (see FIGS. 3a and 3b) as evaluated by confocal microscopy and flow cytometry. Consistent with the complete biocompatibility of its design, the micellar SNAs did not exhibit any cytotoxicity in HEK cells, even at higher concentrations where traditional cationic transfection agents such as Dharmafect can cause detrimental changes in cellular morphology.

Figure 4:
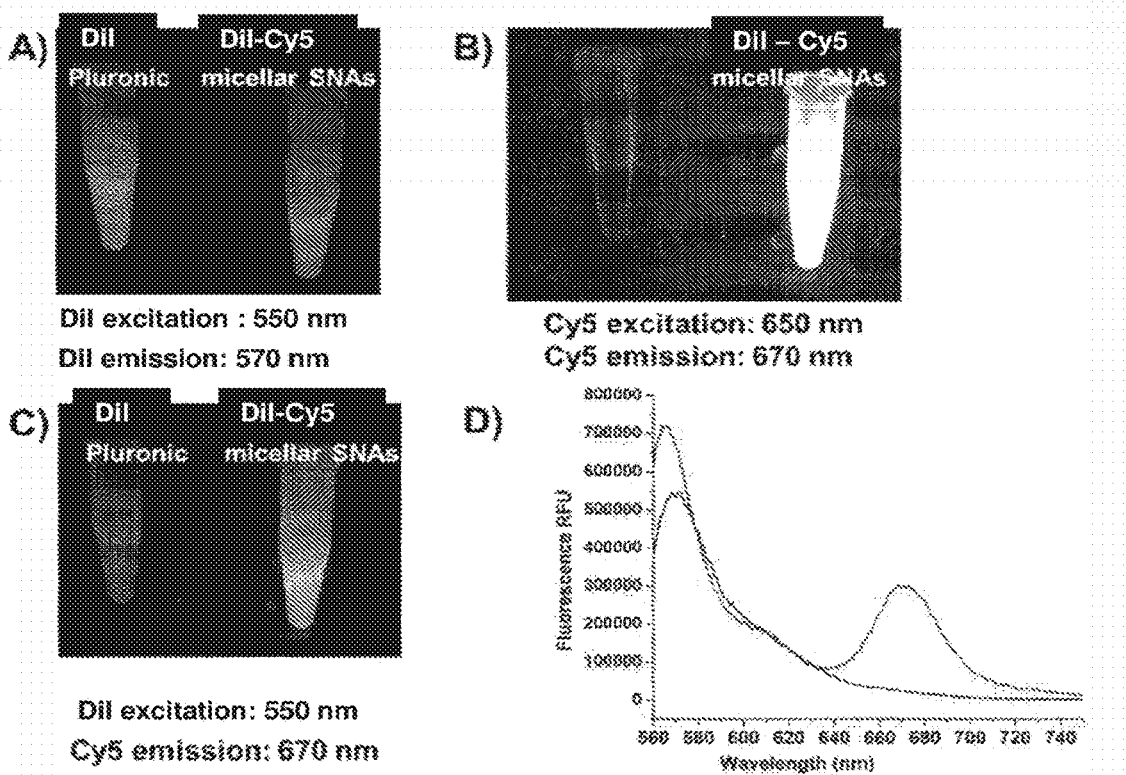
FIG. 4. (A) shows photographic images of DiI-encapsulated Pluronic F127 and Cy5-labeled DNA functionalized crosslinked micellar SNAs. (B) shows photographic images of DiI-encapsulated Pluronic F127 and Cy5-labeled DNA functionalized crosslinked micellar SNAs. (C) shows photographic images of DiI-encapsulated Pluronic F127 and Cy5-labeled DNA functionalized crosslinked micellar SNAs. (D) shows emission spectra of the DiI-encapsulated Pluronic F127 and DiI-encapsulated crosslinked micellar SNA.

FIG. 4A shows photographic images of DiI-encapsulated Pluronic F127 and Cy5-labeled DNA functionalized crosslinked micellar SNAs. FIG. 4B shows photographic images of DiI-encapsulated Pluronic F127 and Cy5-labeled DNA functionalized crosslinked micellar SNAs. FIG. 4C shows photographic images of DiI-encapsulated Pluronic F127 and Cy5-labeled DNA functionalized crosslinked micellar SNAs. FIG. 4D shows emission spectra of the DiI-encapsulated Pluronic F127 and DiI-encapsulated crosslinked micellar SNA, showing the presence of FRET at 670 nm for the latter. The presence of fluorescence resonance energy transfer (FRET) between the DiI and Cy5 dyes is due to the intercalation of the lipid-conjugated DNA into the Pluronic F127 template.

Example 9: Cytotoxicity Studies

The HEK-Blue cells were plated onto a 96 well plate, as described in the flow cytometry experiments above, 24 h before the experiment. The cells were then incubated with micellar SNAs at different concentrations for 24 h, washed three times with 1×PBS, and incubated in alamarBlue® solution (Thermo Fisher Scientific, Inc., Waltham, Mass., USA) for 4 h at 37° C. under a humidified atmosphere with 5 vol % $CO_2$. The fluorescence emission at 590 nm was recorded using a BioTek Synergy H4 Hybrid Reader (BioTek, Winooski, Vt.) and normalized to the signals for untreated cells.

In Vitro Cell Stimulation Studies.

HEK-Blue or Ramos-Blue cells were plated in 96 well plates at a density of 60,000 cells per well for HEK-Blue cells; Ramos-Blue cells were plated at 400,000 cells per well in their respective medium (supplemented with fetal bovine serum (10 vol %), penicillin (0.2 units/mL), and streptomycin (0.1 µg/mL), Normocin™ (100 µg/mL) 2 mM L-glutamine); 200 µL of media/well). Immediately after the plating, the cells were treated with test reagent and incubated at 37° C. in 5% $CO_2$ for 16 h.

For analysis, in a separate plate, 180 µL of QUANTI-Blue™ solution (Invivogen, prepared as per the manufacturer's protocol) was added to each well. To this plate, a 20 µL aliquot of the supernatant of treated HEK-cells was added (20 µl supernatant of untreated HEK-cells was used as a negative control). After 4 h incubation, the change in color due to SEAP activity was quantified by reading the OD at 620-655 nm using a BioTek Synergy H4 Hybrid Reader.

Figure 7:
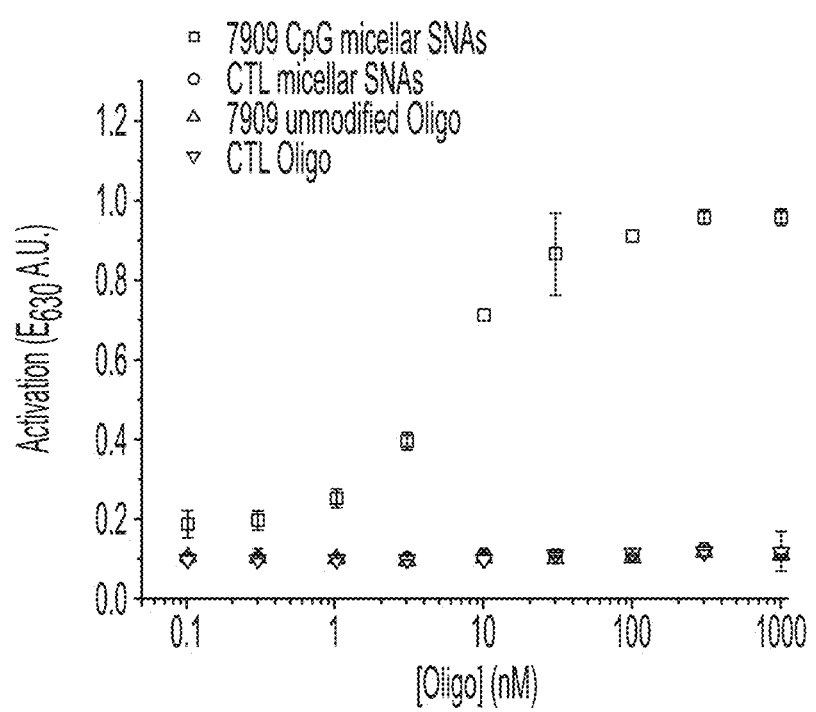
FIG. 7 shows a plot of the amounts of secreted alkaline phosphatase (SEAP) by Ramos-Blue cells, as visualized by a colorimetric assay, showing enhanced immunostimulatory activity by micellar SNAs in comparison to control micellar SNAs bearing a $T_{20}$ sequence and unmodified linear nucleic acids.

FIG. 7 shows a plot of the amounts of secreted alkaline phosphatase (SEAP) by Ramos-Blue cells, as visualized by a colorimetric assay, showing enhanced immunostimulatory activity by micellar SNAs in comparison to control micellar SNAs bearing a $T_{20}$ sequence and unmodified linear nucleic acids.

Micellar SNAs were investigated for their ability for immunomodulatory activity, by incubating Ramos and Raw-Blue cells for 16 h with micellar SNAs synthesized using IS (TLR9 agonist) sequences. A dose-dependent immunostimulatory response was observed when compared to the untreated and negative controls. Convincingly, the micellar SNAs constructed with sequence-specific and therapeutically relevant immunostimulatory nucleic acids can perform better than linear unmodified strands but similar to previously synthesized IS-liposomal SNAs to their rapid cellular uptake, nuclease resistance and accumulation in endosomes. However, nucleic acids with hydrophobic modification form small micellar structures ensuing in similar IS activity as compared to SNAs.

REFERENCES

1. Macfarlane, et al. Science 2011, 334 (6053), 204-8.
2. (a) Seferos, et al. J Am Chem Soc 2007, 129 (50), 15477-9; (b) Sun, et al. Anal Chem 2015, 87 (6), 3354-9.
3. Rosi, et al. Science 2006, 312 (5776), 1027-30.
4. Mirkin, et al. Nature 1996, 382 (6592), 607-609.
5. Cutler, J et al. J Am Chem Soc 2012, 134 (3), 1376-1391.
6. Chung, et al. Biosens Bioelectron 2013, 41, 827-32.
7. Choi, et al. Proc Natl Acad Sci USA 2013, 110 (19), 7625-30.
8. Radovic-Moreno, et al. Proc Natl Acad Sci USA 2015, 112 (13), 3892-7.
9. Massich, et al. ACS Nano 2010, 4 (10), 5641-6.
10. Lee, et al. Nano Lett 2007, 7 (7), 2112-5.
11. Cutler, et al. Nano Lett 2010, 10 (4), 1477-80.
12. Alkilany, et al. J Nanopart Res 2010, 12 (7), 2313-2333.
13. Arnida, et al. J Appl Toxicol 2010, 30 (3), 212-7.
14. Banga, et al. J Am Chem Soc 2014, 136 (28), 9866-9.
15. Brodin, et al. Proc Natl Acad Sci USA 2015, 112 (15), 4564-9.
16. Watson, et al. J Am Chem Soc 2001, 123 (23), 5592-3.
17. Diniz, et al. J Mater Sci-Mater M 2015, 26 (3).
18. (a) Zhang, et al. Nat Nanotechnol 2014, 9 (8), 631-8; (b) Batrakova, et al. J Control Release 2008, 130 (2), 98-106.
19. Linse, et al. Macromolecules 1992, 25 (20), 5434-5439.
20. Lin, et al. J Phys Chem B 2002, 106 (42), 10834-10844.
21. (a) Liu, et al. Theranostics 2012, 2 (7), 705-713; (b) Greish. Methods Mol Biol 2010, 624, 25-37.
22. Hong, et al. J Am. Chem. Soc. 2015, 137 (25), 8184-91.
23. Banchelli, et al. J Phys Chem. B 2008, 112 (35), 10942-52.
24. Banga, et al. J Am. Chem. Soc. 2014, 136 (28), 9866-9.
25. Calabrese, et al. Angew. Chemie 2015, 54 (2), 476-80.

What is claimed:

1. A crosslinked micellar spherical nucleic acid (SNA) comprising a plurality of amphiphilic oligonucleotides, and polyethyleneoxide-polypropyleneoxide-polyethyleneoxide (PEO-PPO-PEO), wherein each amphiphilic oligonucleotide comprises (i) a lipid portion and (ii) a nucleobase portion, wherein the nucleobase portion includes at least one reactive group, wherein the lipid portion is conjugated to a termini of the nucleobase portion, wherein the lipid portion of the amphiphilic oligonucleotide intercalates with the PEO-PPO-PEO, and wherein the plurality of amphiphilic oligonucleotides are crosslinked with a PEGylated crosslinking agent that comprises at least two reactive sites, each of which is capable of forming a covalent bond with the reactive groups of the amphiphilic oligonucleotides and thereby crosslinking the amphiphilic oligonucleotides.

2. The crosslinked micellar SNA of claim 1, having a diameter of 150 nm or less.

3. The crosslinked micellar SNA of claim 1, having at least 200 strands of amphiphilic oligonucleotides.

4. The crosslinked micellar SNA of claim 1, wherein each amphiphilic oligonucleotide comprises an oligonucleotide sequence of 10 to 100 nucleobases.

5. The crosslinked micellar SNA of claim 1, wherein the nucleobase portion of each amphiphilic oligonucleotide comprises a section having a therapeutic sequence.

6. The crosslinked micellar SNA of claim 1, wherein the lipid portion of each amphiphilic oligonucleotide comprises 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), or 1,2-dihexadecanoyl-sn-glycero-3-phosphoethanolamine (DPPE).

7. The crosslinked micellar SNA of claim 1, wherein the lipid portion and the nucleobase portion of the amphiphilic oligonucleotide are connected via a triazolyl.

8. The crosslinked micellar SNA of claim 1, wherein each amphiphilic oligonucleotide comprises RNA and the RNA is a non-coding RNA.

9. The crosslinked micellar SNA of claim 1, wherein each amphiphilic oligonucleotide is DNA and the DNA is antisense-DNA.

10. The crosslinked micellar SNA of claim 8, wherein the non-coding RNA is a microRNA.

11. The crosslinked micellar SNA of claim 1, wherein the reactive group is at the 3' end of the nucleobase portion.

12. The crosslinked micellar SNA of claim 1, wherein the reactive group is at the 5' end of the nucleobase portion.

13. The crosslinked micellar SNA of claim 1, wherein the reactive group in an amine group.

14. The crosslinked micellar SNA of claim 1, wherein the nucleobase portion comprises at least two nucleotides each having the amine reactive group.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_binding
<222> LOCATION: (20)..(20)
<223> OTHER INFORMATION: NH2-NH2-NH2-NH2-NH2
<220> FEATURE:
<221> NAME/KEY: misc_feature
<222> LOCATION: (20)..(20)
<223> OTHER INFORMATION: 18-O-Dimethoxytritylhexaethyleneglycol,1-[(2-

```
       cyanoethyl)-(N,N-diisopropyl)]-phosphoramidite
<220>  FEATURE:
<221>  NAME/KEY: misc_feature
<222>  LOCATION: (20)..(20)
<223>  OTHER INFORMATION: 18-O-Dimethoxytritylhexaethyleneglycol,1-[(2-
       cyanoethyl)-(N,N-diisopropyl)]-phosphoramidite
<220>  FEATURE:
<221>  NAME/KEY: misc_feature
<222>  LOCATION: (20)..(20)
<223>  OTHER INFORMATION: 5'-Dimethoxytrityl-5-[(6-oxo-6-
       (dibenzo[b,f]azacyclooct-4-yn-1-yl)-capramido-N-hex-6-yl)-3-
       acrylimido]-2'-deoxyuridine,3'-[(2-cyanoethyl)-(N,N-diisopropyl)]-
       phosphoramidite

<400>  SEQUENCE: 1 tttttttttt tttttttttt                                                  20

<210>  SEQ ID NO 2
<211>  LENGTH: 20
<212>  TYPE: DNA
<213>  ORGANISM: Artificial Sequence
<220>  FEATURE:
<223>  OTHER INFORMATION: Synthetic oligonucleotide
<220>  FEATURE:
<221>  NAME/KEY: misc_feature
<222>  LOCATION: (1)..(1)
<223>  OTHER INFORMATION: Cy5
<220>  FEATURE:
<221>  NAME/KEY: misc_binding
<222>  LOCATION: (20)..(20)
<223>  OTHER INFORMATION: NH2-NH2-NH2-NH2-NH2
<220>  FEATURE:
<221>  NAME/KEY: misc_feature
<222>  LOCATION: (20)..(20)
<223>  OTHER INFORMATION: 18-O-Dimethoxytritylhexaethyleneglycol,1-[(2-
       cyanoethyl)-(N,N-diisopropyl)]-phosphoramidite
<220>  FEATURE:
<221>  NAME/KEY: misc_feature
<222>  LOCATION: (20)..(20)
<223>  OTHER INFORMATION: 18-O-Dimethoxytritylhexaethyleneglycol,1-[(2-
       cyanoethyl)-(N,N-diisopropyl)]-phosphoramidite
<220>  FEATURE:
<221>  NAME/KEY: misc_feature
<222>  LOCATION: (20)..(20)
<223>  OTHER INFORMATION: 5'-Dimethoxytrityl-5-[(6-oxo-6-
       (dibenzo[b,f]azacyclooct-4-yn-1-yl)-capramido-N-hex-6-yl)-3-
       acrylimido]-2'-deoxyuridine,3'-[(2-cyanoethyl)-(N,N-diisopropyl)]-
       phosphoramidite

<400>  SEQUENCE: 2 tttttttttt tttttttttt                                                  20

<210>  SEQ ID NO 3
<211>  LENGTH: 21
<212>  TYPE: DNA
<213>  ORGANISM: Artificial Sequence
<220>  FEATURE:
<223>  OTHER INFORMATION: Synthetic oligonucleotide
<220>  FEATURE:
<221>  NAME/KEY: misc_feature
<222>  LOCATION: (1)..(1)
<223>  OTHER INFORMATION: 5'-Dimethoxytrityl-5-[(6-oxo-6-
       (dibenzo[b,f]azacyclooct-4-yn-1-yl)-capramido-N-hex-6-yl)-3-
       acrylimido]-2'-deoxyuridine,3'-[(2-cyanoethyl)-(N,N-diisopropyl)]-
       phosphoramidite
<220>  FEATURE:
<221>  NAME/KEY: misc_binding
<222>  LOCATION: (1)..(1)
<223>  OTHER INFORMATION: NH2-NH2-NH2-NH2-NH2

<400>  SEQUENCE: 3 ttttaatcct tatcaatatt t                                                21
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-Dimethoxytrityl-5-[(6-oxo-6-
      (dibenzo[b,f]azacyclooct-4-yn-1-yl)-capramido-N-hex-6-yl)-3-
      acrylimido]-2'-deoxyuridine,3'-[(2-cyanoethyl)-(N,N-diisopropyl)]-
      phosphoramidite
<220> FEATURE:
<221> NAME/KEY: misc_binding
<222> LOCATION: (1)..(1)
<223> OTHER INFORMATION: NH2-NH2-NH2-NH2-NH2

<400> SEQUENCE: 4
ttttaaatat tgataaggat t                                              21

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(25)
<223> OTHER INFORMATION: 18-O-Dimethoxytritylhexaethyleneglycol,1-[(2-
      cyanoethyl)-(N,N-diisopropyl)]-phosphoramidite
<220> FEATURE:
<221> NAME/KEY: misc_feature
<222> LOCATION: (25)..(25)
<223> OTHER INFORMATION: 18-O-Dimethoxytritylhexaethyleneglycol,1-[(2-
      cyanoethyl)-(N,N-diisopropyl)]-phosphoramidite
<220> FEATURE:
<221> NAME/KEY: misc_feature
<222> LOCATION: (25)..(25)
<223> OTHER INFORMATION: 5'-Dimethoxytrityl-5-[(6-oxo-6-
      (dibenzo[b,f]azacyclooct-4-yn-1-yl)-capramido-N-hex-6-yl)-3-
      acrylimido]-2'-deoxyuridine,3'-[(2-cyanoethyl)-(N,N-diisopropyl)]-
      phosphoramidite

<400> SEQUENCE: 5
tccatgacgt tcctgacgtt ttttt                                          25

<210> SEQ ID NO 6
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_binding
<222> LOCATION: (29)..(29)
<223> OTHER INFORMATION: NH2-NH2-NH2-NH2-NH2
<220> FEATURE:
<221> NAME/KEY: misc_feature
<222> LOCATION: (29)..(29)
<223> OTHER INFORMATION: 18-O-Dimethoxytritylhexaethyleneglycol,1-[(2-
      cyanoethyl)-(N,N-diisopropyl)]-phosphoramidite
<220> FEATURE:
<221> NAME/KEY: misc_feature
<222> LOCATION: (29)..(29)
<223> OTHER INFORMATION: 18-O-Dimethoxytritylhexaethyleneglycol,1-[(2-
      cyanoethyl)-(N,N-diisopropyl)]-phosphoramidite
<220> FEATURE:
<221> NAME/KEY: misc_feature
<222> LOCATION: (29)..(29)
<223> OTHER INFORMATION: 5'-Dimethoxytrityl-5-[(6-oxo-6-
      (dibenzo[b,f]azacyclooct-4-yn-1-yl)-capramido-N-hex-6-yl)-3-
      acrylimido]-2'-deoxyuridine,3'-[(2-cyanoethyl)-(N,N-diisopropyl)]-
      phosphoramidite
```

```
<400> SEQUENCE: 6
tcgtcgtttt gtcgttttgt cgttttttt                                  29

<210> SEQ ID NO 7
<211> LENGTH: 17
<212> TYPE: DNA
<213> ORGANISM: Artificial Sequence
<220> FEATURE:
<223> OTHER INFORMATION: Synthetic

<400> SEQUENCE: 7
aatccttatc aatattt                                               17

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
aaatattgat aaggatt                                               17
```